(12) United States Patent
Álvarez Vallina et al.

(10) Patent No.: US 11,306,147 B2
(45) Date of Patent: Apr. 19, 2022

(54) SINGLE CHAIN FUSIONCONSTRUCTS COMPRISING MULTIMERIC ANTIBODY FRAGMENTS FUSED TO COLLAGEN TRIMERIZATION DOMAINS

(71) Applicant: LEADARTIS, S.L., Madrid (ES)

(72) Inventors: Luis Álvarez Vallina, Madrid (ES); Laura Sanz Alcober, Madrid (ES)

(73) Assignee: Leadartis, S.L., Madrid (ES)

( * ) Notice: Subject to any disclaimer, the term of this patent is extended or adjusted under 35 U.S.C. 154(b) by 570 days.

(21) Appl. No.: 16/060,802

(22) PCT Filed: Dec. 9, 2016

(86) PCT No.: PCT/EP2016/080496
§ 371 (c)(1),
(2) Date: Jun. 8, 2018

(87) PCT Pub. No.: WO2017/098005
PCT Pub. Date: Jun. 15, 2017

(65) Prior Publication Data
US 2018/0362653 A1 Dec. 20, 2018

(30) Foreign Application Priority Data

Dec. 11, 2015 (EP) .................................... 15382619
Jan. 5, 2016 (EP) .................................... 16382003

(51) Int. Cl.
| | | |
|---|---|---|
| C07K 16/28 | (2006.01) | |
| C07K 16/30 | (2006.01) | |
| C07K 16/00 | (2006.01) | |
| C07K 16/18 | (2006.01) | |
| C07K 14/47 | (2006.01) | |
| C07K 14/78 | (2006.01) | |
| C12N 15/62 | (2006.01) | |
| C12N 15/85 | (2006.01) | |

(52) U.S. Cl.
CPC .......... *C07K 16/2863* (2013.01); *C07K 14/47* (2013.01); *C07K 14/78* (2013.01); *C07K 16/00* (2013.01); *C07K 16/18* (2013.01); *C07K 16/3007* (2013.01); *C12N 15/62* (2013.01); *C07K 2317/22* (2013.01); *C07K 2317/31* (2013.01); *C07K 2317/35* (2013.01); *C07K 2317/622* (2013.01); *C07K 2317/626* (2013.01); *C07K 2318/20* (2013.01); *C07K 2319/33* (2013.01); *C07K 2319/735* (2013.01); *C07K 2319/74* (2013.01); *C12N 2015/8563* (2013.01)

(58) Field of Classification Search
None
See application file for complete search history.

(56) References Cited

U.S. PATENT DOCUMENTS

2014/0348826 A1* 11/2014 Ivarez Vallina ....... C07K 16/00
424/134.1

FOREIGN PATENT DOCUMENTS

| EP | 2 065 402 A1 | 6/2009 |
|---|---|---|
| JP | 2014-124186 A | 7/2014 |
| TW | 201425335 A | 7/2014 |
| WO | 2012/049328 A1 | 4/2012 |

OTHER PUBLICATIONS

Wirz et al, Matrix Biology 30:9-15, 2011.*
Cuesta et al, mAbs, 4(2):226-232, 2012.*
Alvarez-Cienfuegos et al., "Intramolecular trimerization, a novel strategy for making multispecific antibodies with controlled orientation of the antigen binding domains," *Scientific Reports* 6:28643, 2016, 14 pages.
Blanco-Toribio et al., "Bacterial secretion of soluble and functional trivalent scFv-based N-terminal trimerbodies," *AMB Expr* 5:45, 2015, (8 pages).
Cardoso et al., "Single Domain Camelid Antibodies that Neutralize Negative Strand Viruses," Antiviral Drugs—Aspects of Clinical Use and Recent Advances, 2012, (21 pages). Downloaded from: http://www.intechopen.com/books/antiviral-drugs-aspects-of-clinica-use-and-recent-advances/single-domain-camelid antibodies-that-neutralize-negative-strandviruses.
Cuesta et al., "In Vivo Tumor Targeting and Imaging with Engineered Trivalent Antibody Fragments Containing Collagen-Derived Sequences," *PLoS ONE* 4(4):e5381, 2009, (10 pages).
De Marco, "Recombinant antibody production evolves into multiple options aimed at yielding reagents suitable for application-specific needs," *Microb Cell Fact* 14:125, 2015, (17 pages).
Del Bano et al., "Taking up Cancer Immunotherapy Challenges:Bispecific Antibodies, the Path Forward?" *Antibodies* 5(1), 2016, (24 pages).

(Continued)

*Primary Examiner* — Patricia Duffy
(74) *Attorney, Agent, or Firm* — Seed Intellectual Property Law Group LLP

(57) ABSTRACT

The present invention relates to the field of biomedicine and antibody engineering. Specifically, it relates to mono and multispecific multivalent single chain polypeptide molecules and derivatives thereof, preferably to multispecific single chain (tandem) trimerbodies with defined stoichiometry, to nucleic acid sequences and vectors encoding thereof, and host cells expressing the same. It further relates to methods of producing thereof, pharmaceutical compositions, kits, methods of treatment, use as diagnostics or imaging reagents and combination therapies using thereof.

23 Claims, 14 Drawing Sheets
Specification includes a Sequence Listing.

(56) References Cited

OTHER PUBLICATIONS

Fang et al., "Stable antibody expression at therapeutic levels using the 2A peptide," *Nature Biotechnology* 23(5):584-590, 2005.
Kim et al., "Tribody: Robust Self-Assembled Trimeric Targeting Ligands with High Stability and Significantly Improved Target-Binding Strength," *Biochemistry* 52:7283-7294, 2013.
Li et al., "Targeting and mimicking collagens via triple helical peptide assembly," *Current Opinion in Chemical Biology* 17:968-975, 2013.
Nuñez-Prado et al., "The coming of age of engineered multivalent antibodies," *Drug Discovery Today* 20(5):588-594, 2015.

\* cited by examiner

SEQUENCE LISTING

```
<160> NUMBER OF SEQ ID NOS: 42

<210> SEQ ID NO 1
<211> LENGTH: 64
<212> TYPE: PRT
<213> ORGANISM: Artificial Sequence
<220> FEATURE:
<223> OTHER INFORMATION: Trimerizing structural element of collagen XV
<220> FEATURE:
<221> NAME/KEY: MISC_FEATURE
<222> LOCATION: (1)..(64)

<400> SEQUENCE: 1

Val Thr Ala Phe Ser Asn Met Asp Asp Met Leu Gln Lys Ala His Leu
1               5                   10                  15

Val Ile Glu Gly Thr Phe Ile Tyr Leu Arg Asp Ser Thr Glu Phe Phe
            20                  25                  30

Ile Arg Val Arg Asp Gly Trp Lys Lys Leu Gln Leu Gly Glu Leu Ile
        35                  40                  45

Pro Ile Pro Ala Asp Ser Pro Pro Pro Ala Leu Ser Ser Asn Pro
    50                  55                  60

<210> SEQ ID NO 2
<211> LENGTH: 59
<212> TYPE: PRT
<213> ORGANISM: Artificial Sequence
<220> FEATURE:
<223> OTHER INFORMATION: Trimerizing Structural Element of collagen
      XVIII
<220> FEATURE:
<221> NAME/KEY: MISC_FEATURE
<222> LOCATION: (1)..(59)

<400> SEQUENCE: 2

Ser Gly Val Arg Leu Trp Ala Thr Arg Gln Ala Met Leu Gly Gln Val
1               5                   10                  15

His Glu Val Pro Glu Gly Trp Leu Ile Phe Val Ala Glu Gln Glu Glu
            20                  25                  30

Leu Tyr Val Arg Val Gln Asn Gly Phe Arg Lys Val Gln Leu Glu Ala
        35                  40                  45

Arg Thr Pro Leu Pro Arg Gly Thr Asp Asn Glu
    50                  55
```

```
<210> SEQ ID NO 3
<211> LENGTH: 14
<212> TYPE: PRT
<213> ORGANISM: Artificial Sequence
<220> FEATURE:
<223> OTHER INFORMATION: polyglycine linker
<220> FEATURE:
<221> NAME/KEY: MISC_FEATURE
<222> LOCATION: (1)..(14)

<400> SEQUENCE: 3

Ser Gly Gly Thr Ser Gly Ser Thr Ser Gly Thr Gly Ser Thr
1               5                   10

<210> SEQ ID NO 4
<211> LENGTH: 15
<212> TYPE: PRT
<213> ORGANISM: Artificial Sequence
<220> FEATURE:
<223> OTHER INFORMATION: Polyglycine linker
<220> FEATURE:
<221> NAME/KEY: MISC_FEATURE
<222> LOCATION: (1)..(15)

<400> SEQUENCE: 4

Ala Gly Ser Ser Thr Gly Ser Ser Thr Gly Pro Gly Ser Thr Thr
1               5                   10                  15

<210> SEQ ID NO 5
<211> LENGTH: 7
<212> TYPE: PRT
<213> ORGANISM: Artificial Sequence
<220> FEATURE:
<223> OTHER INFORMATION: polyglycine linker
<220> FEATURE:
<221> NAME/KEY: MISC_FEATURE
<222> LOCATION: (1)..(7)

<400> SEQUENCE: 5

Gly Gly Ser Gly Gly Ala Pro
1               5

<210> SEQ ID NO 6
<211> LENGTH: 8
<212> TYPE: PRT
<213> ORGANISM: Artificial Sequence
<220> FEATURE:
<223> OTHER INFORMATION: polyglycine linker
<220> FEATURE:
<221> NAME/KEY: MISC_FEATURE
<222> LOCATION: (1)..(8)

<400> SEQUENCE: 6

Gly Gly Gly Val Glu Gly Gly Gly
1               5

<210> SEQ ID NO 7
<211> LENGTH: 4
<212> TYPE: PRT
<213> ORGANISM: Artificial Sequence
<220> FEATURE:
<223> OTHER INFORMATION: peptide linker
<220> FEATURE:
<221> NAME/KEY: MISC_FEATURE
<222> LOCATION: (1)..(4)

<400> SEQUENCE: 7

Gly Ser Pro Gly
1
```

```
<210> SEQ ID NO 8
<211> LENGTH: 13
<212> TYPE: PRT
<213> ORGANISM: Artificial Sequence
<220> FEATURE:
<223> OTHER INFORMATION: peptide linker
<220> FEATURE:
<221> NAME/KEY: MISC_FEATURE
<222> LOCATION: (1)..(13)

<400> SEQUENCE: 8

Ala Ala Ala Gly Gly Ser Gly Gly Ser Ser Gly Ser Arg
1               5                   10

<210> SEQ ID NO 9
<211> LENGTH: 8
<212> TYPE: PRT
<213> ORGANISM: Artificial Sequence
<220> FEATURE:
<223> OTHER INFORMATION: peptide linker
<220> FEATURE:
<221> NAME/KEY: MISC_FEATURE
<222> LOCATION: (1)..(8)

<400> SEQUENCE: 9

Gly Ser Gly Ser Gly Ser Gly Ser
1               5

<210> SEQ ID NO 10
<211> LENGTH: 21
<212> TYPE: PRT
<213> ORGANISM: Artificial Sequence
<220> FEATURE:
<223> OTHER INFORMATION: peptide linker
<220> FEATURE:
<221> NAME/KEY: MISC_FEATURE
<222> LOCATION: (1)..(21)

<400> SEQUENCE: 10

Ala Asn Ser Gly Ala Gly Gly Ser Gly Ser Ser Gly Ser Asp Gly
1               5                   10                  15

Ala Ser Gly Ser Arg
            20

<210> SEQ ID NO 11
<211> LENGTH: 10
<212> TYPE: PRT
<213> ORGANISM: Artificial Sequence
<220> FEATURE:
<223> OTHER INFORMATION: peptide linker
<220> FEATURE:
<221> NAME/KEY: MISC_FEATURE
<222> LOCATION: (1)..(10)

<400> SEQUENCE: 11

Pro Lys Pro Ser Thr Pro Pro Gly Ser Ser
1               5                   10

<210> SEQ ID NO 12
<211> LENGTH: 11
<212> TYPE: PRT
<213> ORGANISM: Artificial Sequence
<220> FEATURE:
<223> OTHER INFORMATION: peptide linker
<220> FEATURE:
<221> NAME/KEY: MISC_FEATURE
<222> LOCATION: (1)..(11)

<400> SEQUENCE: 12
```

Ala Pro Ala Glu Thr Lys Ala Glu Pro Met Thr
1               5                   10

<210> SEQ ID NO 13
<211> LENGTH: 5
<212> TYPE: PRT
<213> ORGANISM: Artificial Sequence
<220> FEATURE:
<223> OTHER INFORMATION: peptide linker
<220> FEATURE:
<221> NAME/KEY: MISC_FEATURE
<222> LOCATION: (1)..(5)

<400> SEQUENCE: 13

Ala Ala Ala Leu Glu
1               5

<210> SEQ ID NO 14
<211> LENGTH: 125
<212> TYPE: PRT
<213> ORGANISM: Artificial Sequence
<220> FEATURE:
<223> OTHER INFORMATION: anti-CEA1 VHH
<220> FEATURE:
<221> NAME/KEY: MISC_FEATURE
<222> LOCATION: (1)..(125)

<400> SEQUENCE: 14

Met Ala Gln Val Gln Leu Val Glu Ser Gly Gly Gly Ser Val Gln Ala
1               5                   10                  15

Gly Gly Ser Leu Arg Leu Ser Cys Ala Ala Ser Gly Asp Thr Tyr Gly
            20                  25                  30

Ser Tyr Trp Met Gly Trp Phe Arg Gln Ala Pro Gly Lys Glu Arg Glu
        35                  40                  45

Gly Val Ala Ala Ile Asn Arg Gly Gly Tyr Thr Val Tyr Ala Asp
    50                  55                  60

Ser Val Lys Gly Arg Phe Thr Ile Ser Arg Asp Thr Ala Lys Asn Thr
65                  70                  75                  80

Val Tyr Leu Gln Met Asn Ser Leu Arg Pro Asp Asp Thr Ala Asp Tyr
                85                  90                  95

Tyr Cys Ala Ala Ser Gly Val Leu Gly Gly Leu His Glu Asp Trp Phe
            100                 105                 110

Asn Tyr Trp Gly Gln Gly Thr Gln Val Thr Val Ser Ser
        115                 120                 125

<210> SEQ ID NO 15
<211> LENGTH: 375
<212> TYPE: DNA
<213> ORGANISM: Artificial Sequence
<220> FEATURE:
<223> OTHER INFORMATION: Anti-CEA1 VHH encoding sequence
<220> FEATURE:
<221> NAME/KEY: misc_feature
<222> LOCATION: (1)..(375)

<400> SEQUENCE: 15
atggctcagg tgcagctggt ggagtctggg ggaggctcgg tgcaggctgg agggtctctg     60
agactctcct gtgcggcctc tggagacacc tacggtagct actggatggg ctggttccgc    120
caggctccag ggaaggagcg tgaggggtc gcagctatta ataggggtgg tggctataca    180
gtctacgccg actccgtgaa gggccgattc accatctccc gagacaccgc caagaacacg    240
gtgtatctgc aaatgaacag cctgagacct gacgacacgg ccgactatta ctgtgcggct    300

```
agcggggtac taggtggttt acatgaggac tggtttaact actggggcca ggggacccag    360
gtcaccgtct cctca                                                     375

<210> SEQ ID NO 16
<211> LENGTH: 117
<212> TYPE: PRT
<213> ORGANISM: Artificial Sequence
<220> FEATURE:
<223> OTHER INFORMATION: anti-GFP VHH
<220> FEATURE:
<221> NAME/KEY: MISC_FEATURE
<222> LOCATION: (1)..(117)

<400> SEQUENCE: 16

Met Ala Gln Val Gln Leu Val Glu Ser Gly Gly Ala Leu Val Gln Pro
1               5                   10                  15

Gly Gly Ser Leu Arg Leu Ser Cys Ala Ala Ser Gly Phe Pro Val Asn
            20                  25                  30

Arg Tyr Ser Met Arg Trp Tyr Arg Gln Ala Pro Gly Lys Glu Arg Glu
        35                  40                  45

Trp Val Ala Gly Met Ser Ser Ala Gly Asp Arg Ser Ser Tyr Glu Asp
    50                  55                  60

Ser Val Lys Gly Arg Phe Thr Ile Ser Arg Asp Asp Ala Arg Asn Thr
65                  70                  75                  80

Val Tyr Leu Gln Met Asn Ser Leu Lys Pro Glu Asp Thr Ala Val Tyr
                85                  90                  95

Tyr Cys Asn Val Asn Val Gly Phe Glu Tyr Trp Gly Gln Gly Thr Gln
            100                 105                 110

Val Thr Val Ser Ser
        115

<210> SEQ ID NO 17
<211> LENGTH: 351
<212> TYPE: DNA
<213> ORGANISM: Artificial Sequence
<220> FEATURE:
<223> OTHER INFORMATION: Anti-GFP VHH encoding sequence
<220> FEATURE:
<221> NAME/KEY: misc_feature
<222> LOCATION: (1)..(351)

<400> SEQUENCE: 17
atggctcagg tgcagctggt ggagtctggg ggagccttgg tgcagccggg ggggtctctg     60
agactctcct gtgcagcctc tggattcccc gtcaatcgct atagtatgag gtggtaccgc    120
caggctccag ggaaggagcg cgagtgggtc gcgggtatga gtagtgctgg tgatcgttca    180
agttatgaag actccgtgaa gggccgattc accatctcca gagacgacgc caggaatacg    240
gtgtatctgc aaatgaacag cctgaaacct gaggacacgg ccgtgtatta ctgtaatgtc    300
aatgtgggct ttgagtactg gggccagggg acccaggtca ccgtctcctc a             351

<210> SEQ ID NO 18
<211> LENGTH: 132
<212> TYPE: PRT
<213> ORGANISM: Artificial Sequence
<220> FEATURE:
<223> OTHER INFORMATION: anti-EGFR VHH
<220> FEATURE:
<221> NAME/KEY: MISC_FEATURE
<222> LOCATION: (1)..(132)

<400> SEQUENCE: 18
```

```
Met Ala Gln Val Gln Leu Gln Glu Ser Gly Gly Gly Leu Val Gln Pro
1               5                   10                  15

Gly Gly Ser Leu Arg Leu Ser Cys Ala Ala Ser Gly Arg Thr Phe Ser
            20                  25                  30

Ser Tyr Ala Met Gly Trp Phe Arg Gln Ala Pro Gly Lys Glu Arg Glu
        35                  40                  45

Phe Val Ala Ala Ile Arg Trp Ser Gly Gly Tyr Thr Tyr Tyr Thr Asp
    50                  55                  60

Ser Val Lys Gly Arg Phe Thr Ile Ser Arg Asp Asn Ala Lys Thr Thr
65                  70                  75                  80

Val Tyr Leu Gln Met Asn Ser Leu Lys Pro Glu Asp Thr Ala Val Tyr
                85                  90                  95

Tyr Cys Ala Ala Thr Tyr Leu Ser Ser Asp Tyr Ser Arg Tyr Ala Leu
            100                 105                 110

Pro Gln Arg Pro Leu Asp Tyr Asp Tyr Trp Gly Gln Gly Thr Gln Val
        115                 120                 125

Thr Val Ser Ser
    130

<210> SEQ ID NO 19
<211> LENGTH: 396
<212> TYPE: DNA
<213> ORGANISM: Artificial Sequence
<220> FEATURE:
<223> OTHER INFORMATION: anti-EGFR VHH encoding sequence
<220> FEATURE:
<221> NAME/KEY: misc_feature
<222> LOCATION: (1)..(396)

<400> SEQUENCE: 19
atggctcagg tgcagctgca ggagtctggg ggaggattgg tgcagccagg gggctcgctg      60
agactctcct gtgcagcctc tggacgcacc ttcagtagct atgccatggg ctggttccgc     120
caggctccag ggaaggagcg tgagtttgta gcagctatta ggtggagtgg tggttacaca     180
tactatacag actccgtgaa gggccgattc accatctcca gagacaacgc caagactacg     240
gtgtatctgc aaatgaacag cctgaaacct gaggacacgg ccgtttatta ctgtgcagca     300
acatacctgt cctcggacta tagccgctat gcgttgcccc aaaggccctt ggactatgac     360
tactggggcc agggaccca ggtcaccgtc tcctca                                396

<210> SEQ ID NO 20
<211> LENGTH: 241
<212> TYPE: PRT
<213> ORGANISM: Artificial Sequence
<220> FEATURE:
<223> OTHER INFORMATION: anti-CD3 scFv
<220> FEATURE:
<221> NAME/KEY: MISC_FEATURE
<222> LOCATION: (1)..(241)

<400> SEQUENCE: 20

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60
```

Lys Asp Lys Ala Thr Leu Thr Thr Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Gly Gly Gly Ser Gly Gly Gly Gly
        115                 120                 125

Ser Gly Gly Gly Ser Asp Ile Asp Leu Thr Gln Ser Pro Ala Ile
130                 135                 140

Met Ser Ala Ser Pro Gly Glu Lys Val Thr Met Thr Cys Ser Ala Ser
145                 150                 155                 160

Ser Ser Val Ser Tyr Met Asn Trp Tyr Gln Gln Lys Ser Gly Thr Ser
                165                 170                 175

Pro Lys Arg Trp Ile Tyr Asp Thr Ser Lys Leu Ala Ser Gly Val Pro
            180                 185                 190

Ala His Phe Arg Gly Ser Gly Ser Gly Thr Ser Tyr Ser Leu Thr Ile
        195                 200                 205

Ser Gly Met Glu Ala Glu Asp Ala Ala Thr Tyr Tyr Cys Gln Gln Trp
210                 215                 220

Ser Ser Asn Pro Phe Thr Phe Gly Ser Gly Thr Lys Leu Glu Ile Asn
225                 230                 235                 240

Arg

<210> SEQ ID NO 21
<211> LENGTH: 723
<212> TYPE: DNA
<213> ORGANISM: Artificial Sequence
<220> FEATURE:
<223> OTHER INFORMATION: anti-CD3 scFv encoding sequence
<220> FEATURE:
<221> NAME/KEY: misc_feature
<222> LOCATION: (1)..(723)

<400> SEQUENCE: 21
caggtccagc tgcagcagtc tggcgccgag ctggctagac tggggccag cgtgaagatg      60 agctgcaagg ccagcggcta caccttcacc cggtacacca tgcactgggt caagcagcgg     120
cctgggcagg gcctggaatg gatcggctac atcaaccca gccggggcta caccaactac     180
aaccagaagt tcaaggacaa ggccaccctg accaccgaca agagcagcag caccgcctac     240
atgcagctga gcagcctgac cagcgaggac agcgccgtgt actactgcgc ccggtactac     300
gacgaccact actgcctgga ctactggggc cagggcacca ccctgacagt gtctagcggc     360
ggaggcggat ctggcggcgg aggatctggg ggaggcggct ctgacatcga cctgacacag     420
agccccgcca tcatgagcgc cagccctggc gagaaagtga ccatgacctg cagcgccagc     480
agcagcgtgt cctacatgaa ctggtatcag cagaagtccg gcaccagccc caagcggtgg     540
atctacgaca ccagcaagct ggctagcggc gtgcccgccc actttagagg cagcggcagc     600
ggtacaagct actccctgac catcagcggc atggaagccg aggacgccgc cacctactac     660
tgccagcagt ggtccagcaa ccccttcacc ttcggctccg gcaccaagct ggaaatcaac     720
aga                                                                    723

<210> SEQ ID NO 22
<211> LENGTH: 7
<212> TYPE: PRT

```
<213> ORGANISM: Artificial Sequence
<220> FEATURE:
<223> OTHER INFORMATION: peptide linker
<220> FEATURE:
<221> NAME/KEY: MISC_FEATURE
<222> LOCATION: (1)..(7)

<400> SEQUENCE: 22

Gly Gly Gly Gly Ser Ser Gly
1               5

<210> SEQ ID NO 23
<211> LENGTH: 17
<212> TYPE: PRT
<213> ORGANISM: Artificial Sequence
<220> FEATURE:
<223> OTHER INFORMATION: peptide linker
<220> FEATURE:
<221> NAME/KEY: MISC_FEATURE
<222> LOCATION: (1)..(17)

<400> SEQUENCE: 23

Ser Gly Ala Gly Gly Ser Gly Gly Ser Ser Gly Ser Asp Gly Ala Ser
1               5                   10                  15

Gly

<210> SEQ ID NO 24
<211> LENGTH: 21
<212> TYPE: PRT
<213> ORGANISM: Artificial Sequence
<220> FEATURE:
<223> OTHER INFORMATION: peptide linker
<220> FEATURE:
<221> NAME/KEY: MISC_FEATURE
<222> LOCATION: (1)..(21)

<400> SEQUENCE: 24

Lys Asn Ser Gly Ala Gly Gly Ser Gly Gly Ser Ser Gly Ser Asp Gly
1               5                   10                  15

Ala Ser Gly Ser Arg
            20

<210> SEQ ID NO 25
<211> LENGTH: 31
<212> TYPE: DNA
<213> ORGANISM: Artificial Sequence
<220> FEATURE:
<223> OTHER INFORMATION: ClaGFP (forward primer)
<220> FEATURE:
<221> NAME/KEY: misc_feature
<222> LOCATION: (1)..(31)

<400> SEQUENCE: 25
tgttgcggcc gctagggaga cggtgacctg g                              31

<210> SEQ ID NO 26
<211> LENGTH: 30
<212> TYPE: DNA
<213> ORGANISM: Artificial Sequence
<220> FEATURE:
<223> OTHER INFORMATION: NotGFP (reverse primer)
<220> FEATURE:
<221> NAME/KEY: misc_feature
<222> LOCATION: (1)..(30)

<400> SEQUENCE: 26
gccacatcga tggctcaggt gcagctggtg                                30
```

<210> SEQ ID NO 27
<211> LENGTH: 31
<212> TYPE: DNA
<213> ORGANISM: Artificial Sequence
<220> FEATURE:
<223> OTHER INFORMATION: ClaEGFR (forward primer)
<220> FEATURE:
<221> NAME/KEY: misc_feature
<222> LOCATION: (1)..(31)

<400> SEQUENCE: 27
gcatgatcga tgatggctca ggtgcagctc a                           31

<210> SEQ ID NO 28
<211> LENGTH: 33
<212> TYPE: DNA
<213> ORGANISM: Artificial Sequence
<220> FEATURE:
<223> OTHER INFORMATION: NotEGFR (reverse primer)
<220> FEATURE:
<221> NAME/KEY: misc_feature
<222> LOCATION: (1)..(33)

<400> SEQUENCE: 28
ttgtgcggcc gctgaggaga cggtgacctg ggt                         33

<210> SEQ ID NO 29
<211> LENGTH: 32
<212> TYPE: DNA
<213> ORGANISM: Artificial Sequence
<220> FEATURE:
<223> OTHER INFORMATION: XmaEGFR (forward primer)
<220> FEATURE:
<221> NAME/KEY: misc_feature
<222> LOCATION: (1)..(32)

<400> SEQUENCE: 29
gcatgctcga ggtatggctc aggtgcagct ca                          32

<210> SEQ ID NO 30
<211> LENGTH: 31
<212> TYPE: DNA
<213> ORGANISM: Artificial Sequence
<220> FEATURE:
<223> OTHER INFORMATION: XhoEGFR (reverse primer)
<220> FEATURE:
<221> NAME/KEY: misc_feature
<222> LOCATION: (1)..(31)

<400> SEQUENCE: 30
ttcccgggtg aggagacggt gacctgggtc c                           31

<210> SEQ ID NO 31
<211> LENGTH: 21
<212> TYPE: DNA
<213> ORGANISM: Artificial Sequence
<220> FEATURE:
<223> OTHER INFORMATION: FwCMV (forward primer)
<220> FEATURE:
<221> NAME/KEY: misc_feature
<222> LOCATION: (1)..(21)

<400> SEQUENCE: 31
cgcaaatggg cggtaggcgt g                                      21

<210> SEQ ID NO 32
<211> LENGTH: 18
<212> TYPE: DNA

```
<213> ORGANISM: Artificial Sequence
<220> FEATURE:
<223> OTHER INFORMATION: RvBGH (reverse primer)
<220> FEATURE:
<221> NAME/KEY: misc_feature
<222> LOCATION: (1)..(18)

<400> SEQUENCE: 32
tagaaggcac agtcgagg                                                 18

<210> SEQ ID NO 33
<211> LENGTH: 25
<212> TYPE: PRT
<213> ORGANISM: Artificial Sequence
<220> FEATURE:
<223> OTHER INFORMATION: signal peptide from oncostatin M
<220> FEATURE:
<221> NAME/KEY: MISC_FEATURE
<222> LOCATION: (1)..(25)

<400> SEQUENCE: 33

Met Gly Val Leu Leu Thr Gln Arg Thr Leu Leu Ser Leu Val Leu Ala
1               5                   10                  15

Leu Leu Phe Pro Ser Met Ala Ser Met
            20                  25

<210> SEQ ID NO 34
<211> LENGTH: 68
<212> TYPE: DNA
<213> ORGANISM: Artificial Sequence
<220> FEATURE:
<223> OTHER INFORMATION: signal peptide from oncostatin M encoding
      sequence
<220> FEATURE:
<221> NAME/KEY: misc_feature
<222> LOCATION: (1)..(68)

<400> SEQUENCE: 34 atggggtac tgctcacaca gaggacgctg ctcagtctgg tccttgcact cctgtttcca   60
agcatggc                                                           68

<210> SEQ ID NO 35
<211> LENGTH: 10
<212> TYPE: PRT
<213> ORGANISM: Artificial Sequence
<220> FEATURE:
<223> OTHER INFORMATION: myc-tag
<220> FEATURE:
<221> NAME/KEY: MISC_FEATURE
<222> LOCATION: (1)..(10)

<400> SEQUENCE: 35

Glu Gln Lys Leu Ile Ser Glu Glu Asp Leu
1               5                   10

<210> SEQ ID NO 36
<211> LENGTH: 30
<212> TYPE: DNA
<213> ORGANISM: Artificial Sequence
<220> FEATURE:
<223> OTHER INFORMATION: myc-tag encoding sequence
<220> FEATURE:
<221> NAME/KEY: misc_feature
<222> LOCATION: (1)..(30)

<400> SEQUENCE: 36
gaacaaaaac tcatctcaga agaggatctg                                   30
```

```
<210> SEQ ID NO 37
<211> LENGTH: 6
<212> TYPE: PRT
<213> ORGANISM: Artificial Sequence
<220> FEATURE:
<223> OTHER INFORMATION: 6xHis-tag
<220> FEATURE:
<221> NAME/KEY: MISC_FEATURE
<222> LOCATION: (1)..(6)

<400> SEQUENCE: 37

His His His His His His
1               5

<210> SEQ ID NO 38
<211> LENGTH: 18
<212> TYPE: DNA
<213> ORGANISM: Artificial Sequence
<220> FEATURE:
<223> OTHER INFORMATION: 6xHis-tag encoding sequence

<400> SEQUENCE: 38
catcatcatc accatcac                                              18

<210> SEQ ID NO 39
<211> LENGTH: 15
<212> TYPE: PRT
<213> ORGANISM: Homo sapiens
<220> FEATURE:
<221> NAME/KEY: IgG1 Core hinge sequence
<222> LOCATION: (1)..(15)

<400> SEQUENCE: 39

Glu Pro Lys Ser Cys Asp Lys Thr His Thr Cys Pro Pro Cys Pro
1               5                   10                  15

<210> SEQ ID NO 40
<211> LENGTH: 12
<212> TYPE: PRT
<213> ORGANISM: Homo sapiens
<220> FEATURE:
<221> NAME/KEY: IgG2 Core hinge sequence
<222> LOCATION: (1)..(12)

<400> SEQUENCE: 40

Glu Arg Lys Cys Cys Val Glu Cys Pro Pro Cys Pro
1               5                   10

<210> SEQ ID NO 41
<211> LENGTH: 16
<212> TYPE: PRT
<213> ORGANISM: Homo sapiens
<220> FEATURE:
<221> NAME/KEY: IgG3 Core hinge sequence
<222> LOCATION: (1)..(16)

<400> SEQUENCE: 41

Glu Leu Lys Thr Pro Leu Asp Thr Thr His Thr Cys Pro Arg Cys Pro
1               5                   10                  15

<210> SEQ ID NO 42
<211> LENGTH: 12
<212> TYPE: PRT
<213> ORGANISM: Homo sapiens
<220> FEATURE:
<221> NAME/KEY: IgG4 Core hinge sequence
<222> LOCATION: (1)..(12)
```

```
<400> SEQUENCE: 42

Glu Ser Lys Tyr Gly Pro Pro Cys Pro Ser Pro Cys
1               5                   10
```

SINGLE CHAIN FUSIONCONSTRUCTS COMPRISING MULTIMERIC ANTIBODY FRAGMENTS FUSED TO COLLAGEN TRIMERIZATION DOMAINS

FIELD OF THE INVENTION

The present invention relates to the field of biomedicine and antibody engineering. Specifically, it relates to mono and multispecific multivalent single chain polypeptide molecules and derivatives thereof, preferably to multispecific single chain (tandem) trimerbodies with defined stoichiometry, to nucleic acid sequences and vectors encoding thereof, and host cells expressing the same. It further relates to methods of producing thereof, pharmaceutical compositions, kits, methods of treatment, use as diagnostics or imaging reagents and combination therapies using thereof.

STATE OF THE ART

The development of hybridoma technology in 1975 by Köhler and Milstein (Köhler G, Milstein C., Nature 1975; 256:495-7.) provided an invaluable tool for the generation of highly specific monoclonal antibodies (mAb) with a plethora of applications in research, diagnosis, and therapy (Sanz L, et al., Acta Pharmacol Sin 2005, 26:641-8.). Up to date, forty-three mAbs have been approved by US or EU regulatory agencies for therapeutic use (Reichert J M., MAbs 2015, 7:1-8.). These molecules are generally well tolerated and constitute powerful treatment options for a variety of pathological conditions (Scott A M, et al., Nat Rev Cancer 2012, 12:278-87). However, conventional bivalent monospecific mAbs have limitations, such as inadequate pharmacokinetics and tissue accessibility and unwanted Fc-mediated interactions, at least in some contexts (Cuesta A M, et al., Trends Biotechnol 2010).

To overcome these handicaps, considerable efforts have focused on the development of next generation antibody-based therapeutics (Winter G, Milstein C., Nature 1991; 349:293-9). Conversion of monovalent antibody fragments [e.g. fragment antigen-binding (Fab), single-chain variable fragment (scFv), or single-domain antibody (sdAb)], into multivalent formats enhances functional affinity, decreases dissociation rates and improves biodistribution (Cuesta A M, et al., Trends Biotechnol 2010). The most common strategies to produce multivalent formats have been the engineering of fusion proteins in which the antibody fragment makes a complex with oligomerization domains, and the generation of concatenated "tandem" subunit constructs (Nuñez-Prado N, et al., Drug Discov Today 2015, 20:588-94.).

Recently, we have developed a technology platform for the rapid and efficient generation of multivalent antibodies, termed trimerbodies (Sánchez-Arévalo Lobo V J, et al., International J Cancer 2006, 119:455-62; Cuesta Á M, et al., PLoS One 2009, 4:e5381; Blanco-Toribio A, et al., MAbs 2013, 5:70-9; Cuesta Á M, et al., MAbs 2012, 4:226-32). Engineered homotrimeric antibodies have been obtained by fusing scFv fragments with collagen-derived trimerization (TIE) domains, composed of the N-terminal trimerization region of collagen XVIII NC1 or collagen XV NC1 flanked by flexible peptide linkers, as described in patent documents WO 2012/049328 and WO 2012/022811, respectively. Using this technology, the inventors generated monospecific trivalent trimerbodies (N-trimerbodies or C-trimerbodies; 110 kDa) and monospecific or bispecific hexavalent trimerbodies (N/C-trimerbodies; 190 kDa). Trimeric trivalent and hexavalent scFv-based trimerbodies demonstrated excellent antigen binding capacity and multivalency in vitro and tumor-targeting efficacy in vivo in several mouse models of cancer (Cuesta ÁM, et al., PLoS One 2009, 4:e5381; Sanchez-Martin D, et al., J Biol Chem 2011, 286:5197-203).

SUMMARY OF THE INVENTION

The present invention provides a new strategy that allows the rapid and efficient engineering of mono and multispecific multivalent antibodies comprised in a single polypeptide.

In particular, the inventors generated trimerbodies by fusing single-domain antibodies from camelid heavy-chain-only immunoglobulins ($V_{HHs}$) to the N-terminus of a $TIE^{XVIII}$ domain. $V_{HH}$ antibodies are of particular interest for protein engineering approaches. Despite their small-size (12-15 kDa) and strict monomeric behavior they possess affinities in the same range of conventional antibodies with paired $V_H/V_L$ domains (De Meyer T et al., Trends Biotechnol 2014, 32:263-70). The produced monospecific trimerbodies were efficiently secreted as soluble functional proteins by transfected mammalian cells and the purified $V_{HH}$-$TIE^{XVIII}$ trimerbodies were trimeric in solution and exhibited excellent antigen binding capacity.

Furthermore, tandem trimerbodies were built by connecting with two additional glycine-serine-based linkers three $V_{HH}$-$TIE^{XVIII}$ modules on a single polypeptide chain. Recombinant $V_{HH}$-based trimerbodies were efficiently secreted as soluble proteins by transfected human HEK-293 cells, were trimeric in solution, and were able to recognize their cognate antigen/s with high affinity and specificity. The strategy described herein can be used to efficiently produce multispecific molecules from pre-existent single-domain antibodies. As this new antibody format can target two or more antigens it might have therapeutic potential and conceivable diagnostic or imaging use in multiples diseases, inhibiting simultaneously different pathways involved in their etiopathogenesis as a means to avoid the appearance of resistance.

Furthermore, asymmetric bispecific tandem trimerbodies were built by connecting three anti-EGFR $V_{HH}$-$TIE^{XVIII}$ modules with two additional glycine-serine-based linkers on a single-polypeptide chain and one anti-CD3 scFv fused to the C-terminus of the third $TIE^{XVIII}$. Recombinant asymmetric bispecific trimerbodies were efficiently secreted as soluble proteins by transfected human HEK-293 cells, were easily purified using standard chromatographic methods and were very efficient at recognizing antigen. Importantly, asymmetric bispecific anti-EGFR×anti-CD3 tandem trimerbody were more effective that conventional bispecific anti-EGFR×anti-CD3 tandem antibodies at inducing T cell activation and to effectively engage T cells for redirected lysis of EGFR-expressing cancer cells.

Therefore, in accordance with one aspect of the invention, the invention relates to a molecule according to formula (I) which comprises or consists of:

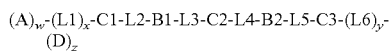

wherein B1 and B2 are monomeric single-domain polypeptides and at least one of B1 or B2 is a single-domain antibody (sdAb) or an antibody mimetic (AbM);

wherein C1, C2 and C3 are collagen XV or collagen XVIII trimerizing structural elements (TSE);

wherein L1, L2, L3, L4, L5 and L6 are peptide linkers, and wherein L2 and L4 have a length from 5 to 40 amino acids;

wherein C1-L2-B1-L3-C2-L4-B2-L5-C3 is a recombinant single-chain polypeptide, C1 being located at the N-terminus of the polypeptide and C3 at the C-terminus of the polypeptide; wherein w, x, y and z can be 1 or 0;
wherein when w is 1 and A is a moiety with binding, detection and/or effector properties, and then A is directly or indirectly covalently linked to the N-terminus of said single-chain polypeptide; and
wherein when z is 1 and D is a moiety with binding, detection and/or effector properties and then D is directly or indirectly covalently linked to the C-terminus of said single-chain polypeptide.

In addition, the present invention provides a nucleic acid sequence encoding a recombinant single-chain polypeptide of formula (I), a recombinant expression vector comprising said nucleic acid sequence and a host cell comprising said expression vector.

It further provides a composition comprising a molecule of formula (I), a nucleic acid sequence, a vector or a cell according to the previous aspects of the invention.

The invention also relates to a pharmaceutical composition comprising a molecule of formula (I), a nucleic acid sequence, a vector or a cell according to the previous aspects of the invention, and a pharmaceutically acceptable excipient or carrier.

In a related aspect, the invention relates to a molecule of formula (I), a nucleic acid sequence, a vector or a cell according to the previous aspects of the invention, for use as a medicament, alone or as a combination therapy. The invention also relates to the use of a molecule of formula (I), a nucleic acid sequence, a vector or a cell according to the previous aspects of the invention in the manufacture of a medicament.

It further provides a method of treatment of a disease or disorder, comprising administering to a subject in need of such treatment a therapeutically effective amount of a molecule of formula (I), a nucleic acid sequence, a vector or a cell according to the previous aspects of the invention. In a particular embodiment, said molecule, nucleic acid sequence, vector or cell is administered with a therapeutically effective amount of another drug, which is administered prior, concomitantly or after its administration. Said other drug may form part of the same composition, or be provided as a separate composition for administration at the same time or at a different time.

The invention further provides a kit which comprises a dosage form of a molecule of formula (I), a nucleic acid sequence, a vector, a cell, composition or pharmaceutical composition of the invention; optionally with a dosage form of another drug; and instructions for the use thereof.

In a further aspect, the present invention also provides a molecule of formula (I), a nucleic acid sequence, a vector, a cell, or pharmaceutical composition of the invention, for use in a method of preventing or treating a disease selected from the group consisting of cancer, inflammatory, immunologic and other angiogenesis-related disorders.

In a related aspect, the invention pertains to a molecule of formula (I), a nucleic acid sequence, a vector or a cell according to the previous aspects of the invention, for use in the manufacturing of a diagnostic kit or as a imaging reagent, alone or in combination with other chemical moieties. The invention also relates to the use of a molecule of formula (I), a nucleic acid sequence, a vector, a cell or pharmaceutical composition of the invention according to the previous aspects of the invention.

In another aspect, the invention relates to a process for the production of a molecule of formula (I), comprising the steps of:
a. introducing a recombinant expression vector comprising a nucleic acid sequence of the invention into an appropriate host cell;
b. culturing the host cell in conditions which enable expression of the nucleic acid sequence,
c. optionally, isolating and/or purifying the expressed polypeptide.

DETAILED DESCRIPTION OF THE INVENTION

Definitions

Figure 1:
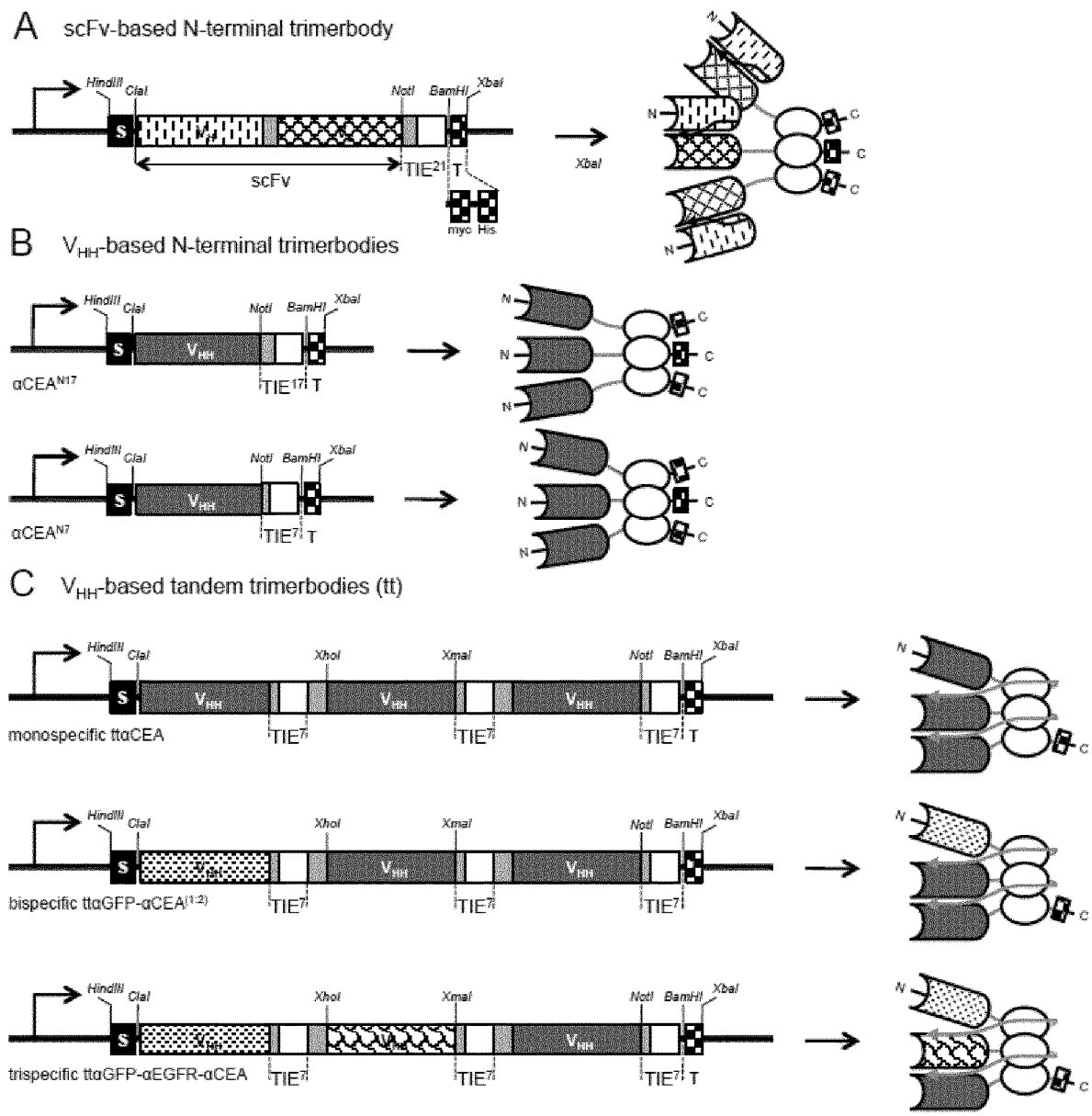
FIG. 1. Schematic diagrams showing the genetic (left) and domain structure (right) of scFv-based (A) and $V_{HH}$-based (B and C) trimerbodies. Conventional multichain trimerbodies (A and B) bear a signal peptide from oncostatin M (S) (SEQ ID NO: 33 and 34), a scFv gene ($V_H$ and $V_L$ domains joined by a flexible linker) (A) or a $V_{HH}$ gene (B), and one TIE domain flanked by flexible peptide linkers of different lengths, and epitope tags (T). The myc-tag (SEQ ID NO: 35 and 36) and the 6×His-tag (SEQ ID NO: 37 and 38) were appended for immunodetection and affinity purification, respectively. Tandem $V_{HH}$-based trimerbodies (C) bear a signal peptide from the oncostatin M (S), three $V_{HH}$ genes and three TIE domains (teal boxes) flanked by 7-mer and 17-mer flexible peptide linkers (grey boxes), and epitope tags (T). Arrows indicate the direction of transcription.

The term "treatment", as used herein, refers to the prophylactic and/or therapeutic treatment.

The term "therapeutic treatment" as used herein refers to bringing a body from a pathological state or disease back to its normal, healthy state. Specifically, unless otherwise indicated, includes the amelioration, cure, and/or maintenance of a cure (i.e., the prevention or delay of relapse) of a disease or disorder. Treatment after a disorder has started aims to reduce, alleviate, ameliorate or altogether eliminate the disorder, and/or its associated symptoms, to prevent it from becoming worse, to slow the rate of progression, or to prevent the disorder from re-occurring once it has been initially eliminated (i.e., to prevent a relapse). It is noted that, this term as used herein is not understood to include the term "prophylactic treatment" as defined herein.

The term "prophylactic treatment" as used herein refers to preventing a pathological state. It is noted that, this term as used herein is not understood to include the term "therapeutic treatment" as defined herein.

A "blocking" antibody or an "antagonist" antibody is one which inhibits or reduces biological activity of the antigen it binds.

An "agonist antibody", as used herein, is an antibody which mimics at least one of the functional activities of a polypeptide of interest.

The term "disease" as used herein is intended to be generally synonymous, and is used interchangeably with, the terms "disorder" and "condition" (as in medical condition), in that all reflect an abnormal condition of the body or of one of its parts that impairs normal functioning and is typically manifested by distinguishing signs and symptoms. This includes chronic and acute disorders or diseases including those pathological conditions which predispose the mammal to the disorder or disease in question. Non-limiting examples of disorders to be treated herein include cancer, inflammatory, immunologic and other angiogenesis-related disorders.

The term "therapeutically effective amount" as used herein refers to an amount that is effective, upon single or multiple dose administration to a subject (such as a human patient) in the prophylactic or therapeutic treatment of a disease, disorder or pathological condition.

The term "combination" or "combination therapy" as used throughout the specification, is meant to encompass the administration of the referred therapeutic agents to a subject suffering from cancer, in the same or separate pharmaceutical formulations, and at the same time or at different times. If the therapeutic agents are administered at different times they should be administered sufficiently close in time to provide for the potentiating or synergistic response to occur. In such instances, it is contemplated that one would typically administer both therapeutic agents within about 12-24 hours of each other and, more preferably, within about 6-12 hours of each other. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations. In other situations, it might be desirable to reduce the time between administration, administering both therapeutic agents within seconds or minutes to hours, preferably within about 6 hours from each other, more preferably within about 1 or 3 hours.

The term "subject" as used herein refers to a mammalian subject. Preferably, it is selected from a human, companion animal, non-domestic livestock or zoo animal. For example, the subject may be selected from a human, dog, cat, cow, pig, sheep, horse, bear, and so on. In a preferred embodiment, said mammalian subject is a human subject.

The term "dosage form" refers to a pharmaceutical composition devised to enable administration of a drug medication in the prescribed dosage amounts. Depending on the method/route of administration different dosage forms will be used. Oral dosage forms comprise liquids (i.e., solutions, suspensions, and emulsions), semi-solids (i.e., pastes), and solids (i.e., tablets, capsules, powders, granules, premixes, and medicated blocks), these may be immediate release or modified release forms. Parenteral dosage forms and delivery systems include injectables (i.e., solutions, suspensions, emulsions, and dry powders for reconstitution), intramammary infusions, intravaginal delivery systems, and implants. Topical dosage forms include solids (i.e., dusting powders), semi-solids (i.e., creams, ointments, and pastes), and liquids (i.e., solutions, suspension concentrates, suspoemulsions, and emulsifiable concentrates). It further includes transdermal delivery systems.

The term "targeted therapy" as used herein refers to compounds that block and/or regulate specific molecules ("molecular targets") that are involved in a disease etiology and development mechanisms, e.g. in the growth, progression, and/or spread of cancer.

The term "resistance" as used herein refers to lack of response to a treatment. It can be either "primary (de novo)", when resistance occurs because of some inherent characteristics of the patient/disease which prevent the treatment's effectiveness; or "secondary (acquired)", which occurs when a patient/disease becomes resistant during treatment because of traits that the patient's cells gain in response to the treatment.

The term "single-domain polypeptides" include biologically functional naturally existing single-domain antibodies (e.g., derived from camelids or sharks); artificial single-domain antibodies; single-domain antibody mimetics (e.g. anticalins, adnectins, Kunitz domanins, avimers, fynomers, Darpins, affibodies, Affilins Armadillo repeat domains, etc.), for a recent review see Weidle et al. Cancer Genomics & Proteomics. 2013, 10:1-18; single-domain growth factors; single-domain cytokines; single-domain chemokines; single-domain truncated cell surface receptors; and other single-domain biologically active polypeptides. The term "biologically active" or "biologically functional" as used herein may refer to the ability of performing a biological function which is characteristic of the specific polypeptide. For instance, in the case of single-domain antibodies or antibody mimetics, this biological activity could be the ability to specifically bind to a particular antigen epitope.

The term "specificity" as used herein may refer to the number of different types of antigens or antigenic determinants to which a particular antigen-binding molecule can bind. The specificity of an antigen-binding molecule can be determined based on affinity and/or avidity. Typically, antigen-binding proteins will bind to their antigen with a dissociation constant (KD) of $10^{-5}$ to $10^{-12}$ moles/liter or less, and preferably $10^{-7}$ to $10^{-12}$ moles/liter or less and more preferably $10^{-8}$ to $10^{-12}$ moles/liter (i.e., with an association constant (KA) of $10^5$ to $10^{12}$ liter/moles or more, and preferably $10^7$ to $10^{12}$ liter/moles or more and more preferably $10^8$ to $10^{12}$ liter/moles). Preferably, antigen-binding domains of the molecule of the invention (e.g. sdAbs, scFv or AbMs) will bind to the desired antigen with an affinity less than 500 nM, preferably less than 200 nM, more preferably less than 10 nM, such as less than 500 pM. Specific binding of an antigen-binding molecule to an antigen or antigenic determinant can be determined in any suitable manner known in the art, including, for example, Scatchard analysis and/or competitive binding assays, such as radioimmunoassays (RIA), enzyme immunoassays (EIA) and sandwich competition assays, and the different variants thereof known per se in the art; as well as the other techniques mentioned herein.

The term "affinity" as used herein may refer to the equilibrium constant for the dissociation of an antigen with an antigen-binding protein (KD), and is considered a measure for the binding strength between an antigenic determinant and an antigen-binding site on the antigen-binding protein: the lesser the value of the KD, the stronger the binding strength between an antigenic determinant and the antigen-binding molecule (alternatively, the affinity can also be expressed as the association constant (KA), which is 1/KD). It will be clear to the skilled person that the dissociation constant may be the actual or apparent dissociation constant.

The KD can also be expressed as the ratio of the dissociation rate constant of a complex, denoted as koff, to the rate of its association, denoted kon (so that KD=koff/kon and KA=kor Aoff). The off-rate koff has units $s^{-1}$ (where s is the SI unit notation of second). The on-rate kon has units $M^{-1} s^{-1}$. The on-rate may vary between $10^2 M^{-1} s^{-1}$ to about $10^7 M^{-1} s^{-1}$, approaching the diffusion-limited association rate constant for bimolecular interactions. The off-rate is related to the half-life of a given molecular interaction by the relation $t_{1/2}=\ln(2)/koff$. The off-rate may vary between $10^{-6} s^{-1}$ (near irreversible complex with a $t_{1/2}$ of multiple days) to $1 s^{-1}$ ($t_{1/2}=0.69$ s). The affinity of a molecular interaction between two molecules can be measured via different techniques known per se, such as the well the known surface plasmon resonance (SPR) biosensor technique (see for example Ober et ah, Intern. Immunology, 13, 1551-1559, 2001) where one molecule is immobilized on the biosensor chip and the other molecule is passed over the immobilized molecule under flow conditions yielding kon, koff measurements and hence KD (or KA) values. This can for example be performed using the well-known BIACORE instruments. The term "avidity" as used herein may refer to the measure of the strength of binding between an antigen-binding molecule and the pertinent antigen. Avidity is related to both the affinity between an antigenic determinant and its antigen binding site on the antigen-binding molecule and the number of pertinent binding sites present on the antigen-binding molecule.

The term "single-domain antibody" (sdAb) as used herein refers to antigen-binding antibodies (or antibody fragments) consisting of a single $V_H$ domain. Examples of sdAbs include, but are not limited to, heavy chain antibodies which are naturally devoid of light chains, and single-domain antibodies derived from conventional four-chain antibodies. The terms sdAbs and immunoglobulin single heavy variable domains (ISHVDs) may be used interchangeably in the present disclosure. Single-domain antibodies may be any of the art, or any future single-domain antibodies. Single-domain antibodies may be derived from any species including, but not limited to mouse, human, camel, llama, goat, rabbit, bovine, shark. According to preferred embodiments of the invention, a single-domain antibody as used herein is a naturally occurring single-domain antibody known as heavy chain antibody devoid of light chains. Such single-domain antibodies are disclosed in WO 94/04678 for example. For clarity reasons, this variable domain derived from a heavy chain antibody naturally devoid of light chain is known herein as a $V_{HH}$ to distinguish it from the conventional $V_H$ of four-chain immunoglobulins. Such a $V_{HH}$ molecule can be derived from antibodies raised in Camelidae species, for example in camel, dromedary, llama, alpaca and guanaco. Other species besides Camelidae may produce heavy chain antibodies naturally devoid of light chain; such $V_{HH_S}$ are within the scope of the invention.

The term "antibody mimetic" (AbM) as used herein refers to single-domain polypeptide scaffolds, which have been engineered to create artificial binding sites against antigens or antigenic determinants (e.g., therapeutic targets) with affinity and specificity that match that of natural antibodies. Antibody mimetics have been developed utilizing an immunoglobulin-like fold which imitates the antibody paratope, for example, fibronectin type III, NCAM and CTLA-4. As way of example, these include: adnectins, anticalins, kunitz domain-based binders, avimers, knottins (cysteine knot miniproteins), fynomers, atrimers and CTLA4-based binders. Other mimetic scaffolds bearing no similarity to immunoglobulin folds have also been obtained based on surface-exposed side chains of secondary structure elements. These include for instance: darpins, affibodies, affilins and armadillo repeat protein-based scaffolds. See for instance, Weidle et al. Cancer Genomics & Proteomics. 2013, 10:1-18; Lofblom, J. et al., Curr. Opin. Biotechnol. 2011, 22: 843-848; Banta, S. et al., Annu. Rev. Biomed. Eng., 2010, 15: 93-113 which provide further details on each of this specific AbM molecules and are herein incorporated by reference.

The term "recombinant antibody" as used herein refers to an antibody produced or expressed using a recombinant expression vector, where the expression vector comprises a nucleic acid encoding the recombinant antibody, such that introduction of the expression vector into an appropriate host cell results in the production or expression of the recombinant antibody. Recombinant antibodies may be chimeric or humanized antibodies, mono- or multi-specific antibodies. The term "antibody" also refers to fragments and derivatives of all of the foregoing, and may further comprise any variants thereof that retain the ability to specifically bind an epitope. Antibodies may include, but are not limited to monoclonal antibodies (mAbs), camelid antibodies, single-chain antibodies (scFvs), Fab fragments, F(ab')2 fragments, disulphide-linked Fvs (sdFv) fragments, anti-idiotypic (anti-Id) antibodies, intra-bodies, synthetic antibodies, and epitope-binding fragments of any of the above. The term "antibody" also refers to fusion protein that includes a region equivalent to the Fc region of an immunoglobulin. In some embodiments, a recombinant antibody is sdAb (preferably a $V_{HH}$) or scFv.

A "polynucleotide" or "nucleic acid" sequence as used herein refers to a DNA or RNA sequence, preferably to a DNA sequence. The term captures sequences that include any of the known base analogs of DNA and RNA such as, but not limited to 4-acetylcytosine, 8-hydroxy-N6-methyl-adenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethyl-guanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonyl-methyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

A "coding sequence" or a sequence which "encodes" a gene product as used herein, refers to a nucleic acid sequence which is transcribed (in the case of DNA) and translated (in the case of mRNA), in vitro or in vivo when placed under the control of appropriate regulatory sequences.

The terms DNA "control sequences" and "control elements" as used herein, refer collectively to promoter sequences, polyadenylation signals, transcription termination sequences, upstream regulatory domains, origins of replication, internal ribosome entry sites ("IRES"), enhancers, and the like, which collectively provide for the replication, transcription and translation of a coding sequence in a recipient cell. Not all of these control sequences/elements need always be present so long as the selected coding sequence is capable of being replicated, transcribed and translated in an appropriate host cell.

"Operably linked" as used herein refers to an arrangement of elements wherein the components so described are configured so as to perform their usual function. Thus, control sequences operably linked to a coding sequence are capable of effecting the expression of the coding sequence. The control sequences need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

The term "promoter" as used herein refers to a region of DNA that initiates transcription of a particular coding sequence. Promoters are located near the transcription start sites of genes, on the same strand and upstream on the DNA (towards the 5' region of the sense strand). Promoters can be about 100-1000 base pairs long. An "eukaryotic promoter" includes cis-acting elements such as binding sites for activating protein-1 (AP-1), nuclear factor κB (NF-κB), CArG binding factor A (CBF-A), nuclear factor Y (NF-Y) and others, in addition to the TATA box sequence.

The term "amino acid" as used herein, includes the 20 common naturally occurring amino acids, seleno cysteine, pyrrolysine and "unnatural amino acids". The term "unnatural amino acid" as used herein refers to any other amino acid, modified amino acid, and/or amino acid analogue. Examples of unnatural amino acids include but are not limited to: a p-acetyl-L-phenylalanine, a p-iodo-L-phenylalanine, an O-methyl-L-tyrosine, a p-propargyloxyphenylalanine, a p-propargyl-phenylalanine, an L-3-(2-naphthyl)alanine, a 3-methyl-phenylalanine, an O-4-allyl-L-tyrosine, a 4-propyl-L-tyrosine, a tri-O-acetyl-GlcNAcβ-serine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-bromophenylalanine, a p-amino-L-phenylalanine, an isopropyl-L-phenylalanine, an unnatural analogue of a tyrosine amino acid; an unnatural analogue of a glutamine amino acid; an unnatural analogue of a phenylalanine amino acid; an unnatural analogue of a serine amino acid; an unnatural analogue of a threonine amino acid; an alkyl, aryl, acyl, azido, cyano, halo, hydrazine, hydrazide, hydroxyl, alkenyl, alkynl, ether, thiol, sulfonyl, seleno, ester, thioacid, borate, boronate, phospho, phosphono, phosphine, heterocyclic, enone, imine, aldehyde, hydroxylamine, keto, or amino substituted amino acid, or any combination thereof; an amino acid with a photoactivatable cross-linker; a spin-labeled amino acid; a fluorescent amino acid; a metal binding amino acid; a metal-containing amino acid; a radioactive amino acid; a photocaged and/or photoisomerizable amino acid; a biotin or biotin-analogue containing amino acid; a keto containing amino acid; an amino acid comprising polyethylene glycol or polyether; a heavy atom substituted amino acid; a chemically cleavable or photocleavable amino acid; an amino acid with an elongated side chain; an amino acid containing a toxic group; a sugar substituted amino acid; a carbon-linked sugar-containing amino acid; a redox-active amino acid; an α-hydroxy containing acid; an amino thio acid; an α,α disubstituted amino acid; a β-amino acid; a cyclic amino acid other than proline or histidine, an aromatic amino acid other than phenylalanine, tyrosine or tryptophan, and/or the like.

DETAILED DESCRIPTION

A Monospecific or Multispecific Molecule of the Invention

In accordance with one aspect of the invention, the invention relates to a molecule according to formula (I) which comprises or consists of:

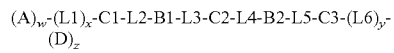

wherein B1 and B2 are monomeric single-domain polypeptides and at least one of B1 or B2 is a single-domain antibody (sdAb) or an antibody mimetic (AbM);

wherein C1, C2 and C3 are collagen XV or collagen XVIII trimerizing structural elements (TSE);

wherein L1, L2, L3, L4, L5 and L6 are peptide linkers, and wherein L2 and L4 have a length from 5 to 40 amino acids;

wherein C1-L2-B1-L3-C2-L4-B2-L5-C3 is a recombinant single-chain polypeptide, C1 being located at the N-terminus of the polypeptide and C3 at the C-terminus of the polypeptide;

wherein w, x, y and z can be 1 or 0;

wherein when w is 1 and A is a moiety with binding, detection and/or effector properties, and then A is directly or indirectly covalently linked to the N-terminus of said single-chain polypeptide; and wherein when z is 1 and D is a moiety with binding, detection and/or effector properties and then D is directly or indirectly covalently linked to the C-terminus of said single-chain polypeptide.

The term "tandem trimerbody" or "tandem trimerbodies" is used throughout the specification to refer to a molecule according to formula (I).

In some embodiments, w and/or z are 1. Preferably, when w is 1 and A is a (poly)peptide then x is 1, and when z is 1 and D is a (poly)peptide then y is 1. In other embodiments, w, x, y and z are 0.

In a particular embodiment, optionally in combination with one or more features of the embodiments described above or below, B1 and B2 are sdAbs or AbMs. Preferably at least one of B1 or B2 is a $V_{HH}$ antibody, more preferably both are $V_{HH}$ antibodies.

AbM scaffolds can be structurally divided under two main groups i) wherein binding can be mediated by one or more loops on a typically rigid protein structure which imitates the antibody paratope and ii) by surface-exposed side chains of secondary structure elements. For illustration purposes, the first (i) group includes but it is not limited to: adnectins, anticalins, kunitz domain-based binders, avimers, knottins, fynomers, atrimers and CTLA4-based binders; whereas illustrative non-limiting examples of the second (ii) group include: darpins, affibodies, affilins and armadillo repeat protein-based scaffolds. Further details on each of these specific AbM molecules are provided in Weidle et al. Cancer Genomics & Proteomics. 2013, 10:1-18; Lofblom, J. et al., Curr. Opin. Biotechnol. 2011, 22: 843-848; Banta, S. et al., Annu. Rev. Biomed. Eng., 2010, 15: 93-113 which are herein incorporated by reference.

Accordingly, the AbM may be selected from the group consisting of adnectins, lipocalins, kunitz domain-based binders, avimers, knottins, fynomers, atrimers, CTLA4-based binders, darpins, affibodies, affilins and armadillo repeat protein-based scaffolds. These have typically a size of between 4-20 kDa which is similar to that of sdAbs (about 12-15 kDa). As a reference, the table below provides the molecular mass of some AbMs, namely of adnectins, anticalins, kunitz domain peptides, avimers, fynomers, affibodies, affilins and darpins.

| Name | Molecular scaffold | Sequence (amino acids) | Molecular mass |
|---|---|---|---|
| Adnectins | Fibronectin type III domain (FN3) | 94 | 10 kDa |
| Anticalins | Lipocalin | 180 | 20 kDa |
| Kunitz domain peptides | Kunitz domains of various protease inhibitors | 50-60 | 6 kDa |
| Avimers | A domains of membrane receptors | 30-35 (x1/x3) | 4-18 kDa |
| Fynomers | SH3 domain of Fyn | 63 | 7 kDa |
| Affibodies | Z domain of protein A | 58 | 6 kDa |
| Affilins | γ-B crystallin or human ubiquitin | 180 | 20 kDa |
| Darpins | ankyrin protein | 33 (x2/x7) | 10-26 kDa |

In preferred embodiments, AbMs are selected from the group consisting of adnectins, anticalins, kunitz domain peptides, avimers, fynomers, affibodies, affilins and darpins. Preferably, and irrespectively of the selected molecular scaffold, said AbMs have a molecular mass of no more than 20 kDa, more preferably less than 16 kDa, such as between 10 kDa and 15 kDa. Collagen XV and collagen XVIII trimerizing structural elements are described in the specification of WO 2012/022811 and WO 2012/049328 which are herein incorporated by reference. As used herein, the term "collagen XV trimerizing structural element" or "XVTSE" refers to a polypeptide which comprises or consists of a polypeptide having the amino acid sequence shown in SEQ ID NO: 1: VTAFSNMDDMLQKAHLVIEGTFIYLRDST-EFFIRVRDGWKKLQLGELIPIPADSPPPPALSSNP, or to a polypeptide having at least 60%, preferably at least 65%, 70%, 75%, 80%, 85%, 90%, 95%, 98% or at least 99% amino acid sequence identity with the sequence shown in SEQ ID NO: 1, and maintains the ability to form trimers and/or produce intramolecular trimerization. SEQ ID NO: 1 comprises the amino acid sequence of the trimerization domain of human collagen XV (i.e., the human collagen XV NC1 domain without the ES domain—sometimes referred to in this description as "NC1$^{ES-}$", "NC1" or "trimerization domain"). Preferably, the XVTSE comprises, or consists of, the amino acid sequence shown in SEQ ID NO: 1.

As used herein, the term "collagen XVIII trimerizing structural element" or "XVIIITSE" refers to a polypeptide which comprises or consists of a polypeptide having the amino acid sequence shown in SEQ ID NO: 2:SGVRL-WATRQAMLGQVHEVPEGWLIFVAEQEELYVRVQNG-FRKVQLEARTPL PRGTDNE, or to a polypeptide having at least 60%, preferably at least 65%, 70%, 75%, 80%, 85%, 90%, 95%, 98% or at least 99% amino acid sequence identity with the sequence shown in SEQ ID NO: 1, and maintains the ability to form trimers and/or produce intramolecular trimerization. Preferably, the XVIIITSE comprises, or consists of, the amino acid sequence shown in SEQ ID NO: 2.

The above-defined variants of SEQ ID NO: 1 or SEQ ID NO: 2, may result from the modification of SEQ ID NO: 0.1 or SEQ ID NO: 0.2, respectively, by the conservative or non-conservative substitution of one or more amino acids, the insertion and/or the deletion of one or more amino acids. The degree of identity between two amino acid sequences can be determined by any conventional method, for example, by means of standard sequence alignment algorithms known in the state of the art, such as, for example BLAST (Altschul S. F. et al., J Mol Biol. 1990, 215:403-10).

The XVTSE and XVIIITSE domains have the ability to form trimers and/or produce intramolecular trimerization, at physiological conditions, i.e., conditions that permit in vivo protein expression in the cytosol of an eukaryotic or a prokaryotic organism. The ability of a polypeptide to trimerize can be determined by conventional methods known by the skilled person in the art. For example, by way of a simple illustration, the ability of a polypeptide to trimerize can be determined by using standard chromatographic techniques. Thus, the polypeptide to be assessed is put under suitable trimerization conditions and the complex is subjected to a standard chromatographic assay under non-denaturing conditions so that the eventually formed complex (trimer) is not altered. If the variant trimerizes properly, the molecular size of the complex would be three times heavier than the molecular size of a single molecule of the variant. The molecular size of the complex can be revealed by using standard methods such as analytical centrifugation, mass spectrometry, size-exclusion chromatography, etc.

The degree of identity of the trimerization region from collagen XV NC1 domain is about 32%>with respect to the trimerization region from collagen XVIII NC1 domain. The person skilled in the art will understand that the amino acid sequences referred herein can be chemically modified, for example, by means of chemical modifications which are physiologically relevant, such as, phosphorylations, acetylations, etc.

The term "peptide linker", "linker" or "spacer" as used herein refers to a spacer acting as a hinge region between polypeptide domains, allowing them to move independently from one another while maintaining the three-dimensional form of the individual domains. In this sense, a preferred spacer would be a hinge region characterized by a structural ductility or flexibility allowing this movement. This includes flexible peptide linkers as defined below, as well as the hinge region of antibodies or other spacer peptides used for the production of dimeric or multimeric antibody-based molecules.

The length of the spacer can vary; typically, the number of amino acids in the spacer is 100 or less amino acids, preferably 50 or less amino acids, more preferably 40 or less amino acids, still more preferably, 30 or less amino acids, or even more preferably 20 or less amino acids. Preferred ranges are from 5 to 50, preferably from 10 to 30, more preferably from 15 to 25 amino acids. In a preferred embodiment the length of the spacer is of about 15 or about 20 amino acids. In another preferred embodiment, the length of the spacer is of around 10 amino acids. Preferred linkers have 7, 17 or 21 amino acids.

In a particular embodiment, optionally in combination with one or more features of the embodiments described above or below, the peptide linkers L2, L4 and/or L6 of the molecule according to formula (I) have a length from 5 to 40 amino acids, preferably from 10 to 30 amino acids, more preferably of around 10, around 15, around 20 or around 25 amino acids, even more preferably of about 17 or about 21 amino acids.

In a preferred embodiment, optionally in combination with one or more features of the embodiments described above or below, L1, L3 and/or L5 have from 4 or 5 to 10 amino acids, preferably around 7 amino acids; and L2, L4 and/or L6 have from 15 to 20 or 21 amino acids, preferably about 17 or about 21 amino acids.

In preferred embodiments, said spacer is a peptide having structural flexibility (i.e., a flexible linking peptide or "flexible linker") and comprises 2 or more amino acids selected from the group consisting of glycine, serine, alanine and threonine. Preferably, wherein at least 65%, preferably 70%, 75%, 80%, 85%, 90%, 95%, 96%, 97%, 98%, 99% or 100% of the amino acids in said flexible peptide linker are selected from the group consisting of glycine, serine, alanine and threonine.

The spacer peptide may preferably contain repeats of amino acid residues, particularly Gly and Ser, or any other suitable repeats of amino acid residues. Regardless the presence or absence of repeats, it is also preferred that at least 65%, preferably 70%, 75%, 80%, 85%, 90%, 95%, 96%, 97%, 98%, 99% or 100% of the amino acids in the peptide linker are selected from the group consisting of Gly and Ser.

Illustrative, non-limitative examples of flexible linkers include amino acid sequences such SGGTSGSTSGTGST (SEQ ID NO: 3), AGSSTGSSTGPGSTT (SEQ ID NO: 4), GGSGGAP (SEQ ID NO: 5), GGGVEGGG (SEQ ID NO: 6), Gly-Ser-Pro-Gly (GSPG; SEQ ID NO: 7), Ala-Ala-Ala-Gly-Gly-Ser-Gly-Gly-Ser-Ser-Gly-Ser-Arg (AAAGGSGGSSGSR; SEQ ID NO: 8), Gly-Ser-Gly-Ser-Gly-Ser-Gly-Ser (Gly-Ser)4 (GSGSGSGS; SEQ ID NO: 9) or Ala-Asn-Ser-Gly-Ala-Gly-Gly-Ser-Gly-Gly-Ser-Ser-Gly-Ser-Asp-Gly-Ala-Ser-Gly-Ser-Arg (ANSGAGGSGGSSGSDGASGSR; SEQ ID NO: 10).

Alternatively, a suitable spacer can be based on the sequence of 10 amino acid residues of the upper hinge region of murine IgG3; said peptide (PKPSTPPGSS, SEQ ID NO: 11)) has been used for the production of dimerized antibodies by means of a coiled coil (Pack P. and Pluckthun, A., Biochemistry 1992, 31:1579-1584) and can be useful as a spacer peptide according to the present invention.

Said spacer can also be a corresponding sequence of the upper hinge region of human IgG3 or other human Ig subclasses (IgG1, IgG2, IgG4, IgM and IgA). The sequences of human Igs are not expected to be immunogenic in human beings. For illustrative purposes, the core hinge sequence of human IgG1, IgG2, IgG3 and IgG4 subtypes are provided in the table below:

| IgG subtype | Core hinge sequence | SEQ ID NO: |
|---|---|---|
| IgG1 | EPKSCDKTHTCPPCP | 39 |
| IgG2 | ERKCCVECPPCP | 40 |
| IgG3 | ELKTPLDTTHTCPRCP | 41 |
| IgG4 | ESKYGPPCPSPC | 42 |

Additional spacers that can be used in the instant invention include the peptides of the amino acid sequences GAP, AAA, or those shown in APAETKAEPMT (SEQ ID NO: 12), or AAALE (SEQ ID NO: 13).

In some embodiments, said peptide linkers contain an amino acid sequence specifically cleavable by enzymatic or chemical means. In a particular embodiment, said one or more peptide linkers comprises an amino acid sequence which is cleavable by a protease such as an enterokinase, Arg-C endoprotease, Glu-C endoprotease, Lys-C endoprotease, factor Xa, furin-like proprotein convertase, etc. Alternatively, in another particular embodiment, said cleavable linker comprises an amino acid sequence which is cleavable by a chemical reagent, such as, for example, cyanogen bromide which cleaves methionine residues, or any other suitable chemical reagent. Preferably one or more of the peptide linkers contain the recognition site for a peptidase, more preferably wherein said peptidase is a furin-like proprotein convertase (Fang J et al., Nat Biotechnol 2005; 23:584-90).

In particularly preferred embodiments, optionally in combination with one or more features of the embodiments described above or below, said flexible peptide linkers are selected from the group consisting of:

```
7-mer linker:
                            (SEQ ID NO: 22)
GGGGSSG 17-mer linker:
                            (SEQ ID NO: 23)
SGAGGSGGSSGSDGASG
and 21-mer linker:
                            (SEQ ID NO: 24)
KNSGAGGSGGSSGSDGASGSR.
```

In a more preferred embodiment, optionally in combination with one or more features of the embodiments described above or below, L2, L4 and/or L6 are selected from the group consisting of amino acid sequences SEQ ID NO:23 and SEQ ID NO:24. Preferably, L1, L3 and/or L5 have amino acid sequence SEQ ID NO:22; and L2, L4 and/or L6 are selected from the group consisting of amino acid sequences SEQ ID NO:23 and SEQ ID NO:24.

The term "moiety" as used herein refers to any chemical or biological entity, which may be fused or covalently linked to the (A)w-(L1)x-C1-L2-B1-L3-C2-L4-B2-L5-C3-(L6)y-(D)z recombinant single-chain polypeptide. Said moiety typically has binding, detection and/or effector properties. Illustrative, non-limitative, examples of moieties include:

a) a ligand binding structure, such as a receptor molecule or the ligand binding part of a receptor molecule, such as for example a truncated form of the vascular endothelial factor receptor (VEGFR) 1 or 2; a recombinant antibody, antibody mimetics, or other ligand binding molecules without restriction such as avidin, streptavidin, or a lectin;

b) a toxin such as ricin, *Pseudomonas* exotoxin A, etc.;
c) a detectable label such as a fluorescence labelled molecule, a radioactively labelled molecule, or an enzymatically labelled molecule;
d) a pro-drug or substance which may be activated in situ, such as a molecule which can be induced by a magnetic field or by radiation to be radioactively or chemically active;
e) an enzyme such as a peroxidase, etc.;
f) a radioactive moiety such as a y-, a-, ß-, or ß+-emitting molecule, e.g. a molecule comprising one or more radioactive isotopes;
g) a cytokine such as an interferon, an interleukin (e.g., interleukin-12.), a leukotriene, an angiogenic growth factor such as vascular endotelial factor (e.g., VEGF);
h) an angiogenesis inhibitor such as endostatin, angiostatin, etc.
i) a Peptide Nucleic Acid (PNA);
j) a non-proteinaceous polymer such as a polymeric alkaloid;
K) a polyalcohol;
l) a polysaccharide;
m) a lipid;
n) a polyamine;
o) a photo cross-linking moiety, i.e., a chemical entity which effects cross-linking upon photo-activation;
p) a group facilitating conjugation of the monomer polypeptide to a target; or
q) a tag, i.e., a tag for the purpose of facilitating the isolation and purification of the trimeric complex of the invention, for example an affinity purification tag such as a tag peptide; illustrative, non-limitative examples of said tags include polyhistidine [poly(His)] sequences (e.g., 6×His-tag), peptide sequences capable of being recognized by antibodies that may be used to purify the resultant fusion protein by immunoaffinity chromatography, for example epitopes derived from the hemagglutinin of the fever virus or C-myc epitope, Strep tag, Flag-tag, etc.

In some embodiments, said moiety is a recombinant antibody and/or an antibody mimetic (AbM). In other embodiments, said moiety is other than a recombinant antibody or an AbM. In a particular embodiment, the moiety comprises a specific affinity purification tag. Said affinity purification tag can be fused directly in-line or, alternatively, fused to the polypeptide via a cleavable linker, i.e., a peptide segment containing an amino acid sequence that is specifically cleavable by enzymatic or chemical means (i.e., a recognition/cleavage site). In a particular embodiment, said cleavable linker comprises an amino acid sequence which is cleavable by a protease such as an enterokinase, Arg-C endoprotease, Glu-C endoprotease, Lys-C endoprotease, factor Xa, furin-like proprotein convertase, etc.; alternatively, in another particular embodiment, said cleavable linker comprises an amino acid sequence which is cleavable by a chemical reagent, such as, for example, cyanogen bromide which cleaves methionine residues, or any other suitable chemical reagent. The cleavable linker is useful if subsequent removal of the affinity purification tags is desirable.

In a particular embodiment, optionally in combination with the embodiments described above or below, said molecule of formula (I) is selected from the group consisting of:
i. a molecule wherein w and x are 1; A, B1 and B2 are sdAbs or AbMs; y is 0, and z is 0 or z is 1 when D is a moiety other than a (poly)peptide, preferably other than a recombinant antibody or an AbM;
ii. a molecule wherein w and x are 1; A is a single-chain variable fragment (scFv), and B1 and B2 are sdAbs or AbMs; y is 0, and z is 0 or z is 1 when D is a moiety other than a (poly)peptide, preferably other than a recombinant antibody or an AbM;
iii. a molecule wherein z and y are 1; D, B1, and B2 are sdAbs; x is 0, and w is 0 or w is 1 when is a moiety other than a (poly)peptide, preferably other than a recombinant antibody or an AbM;
iv. a molecule wherein z and y are 1; D is a scFv, and B1 and B2 are sdAbs; x is 0, and w is 0 or w is 1 when A is a moiety other than a (poly)peptide, preferably other than a recombinant antibody or an AbM;
v. a molecule wherein w, x, y and z are 1; and A, B1, B2 and D are sdAbs or AbMs;
vi. a molecule wherein w, x, y and z are 1; and A, B1 and B2 are sdAbs or AbMs, and D is a scFv;
vii. a molecule wherein w, x, y and z are 1; and D, B1 and B2 are sdAbs or AbMs, and A is a scFv;
viii. a molecule wherein w, x, y and z are 1; and A and D are scFv and B1 and B2 are sdAbs or AbMs;
ix. a molecule wherein w and x are 0; y and z are 1; B1 and B2 are sdAbs or AbMs; and D is a (poly)peptide other than scFv, sdAbs or AbMs;
x. a molecule wherein y and z are 0; w and x, are 1; B1 and B2 are sdAbs or AbMs; and A is a (poly)peptide other than scFv, sdAbs or AbMs;
xi. a molecule wherein w and z are 1; x and y are 0; B1 and B2 are sdAbs or AbMs; and A and D are moieties other than a (poly)peptide;
xii. a molecule wherein w, x, y and z are 0; and B1 and B2 are sdAbs or AbMs.

In preferred embodiments, said (poly)peptide other than scFv, sdAbs or AbMs is selected from the group consisting of a receptor molecule or the ligand-binding part of said receptor molecule, a cytokine, a toxin polypeptide, an enzyme, a peptide tag and the Fc region of an antibody.

Figure 10:
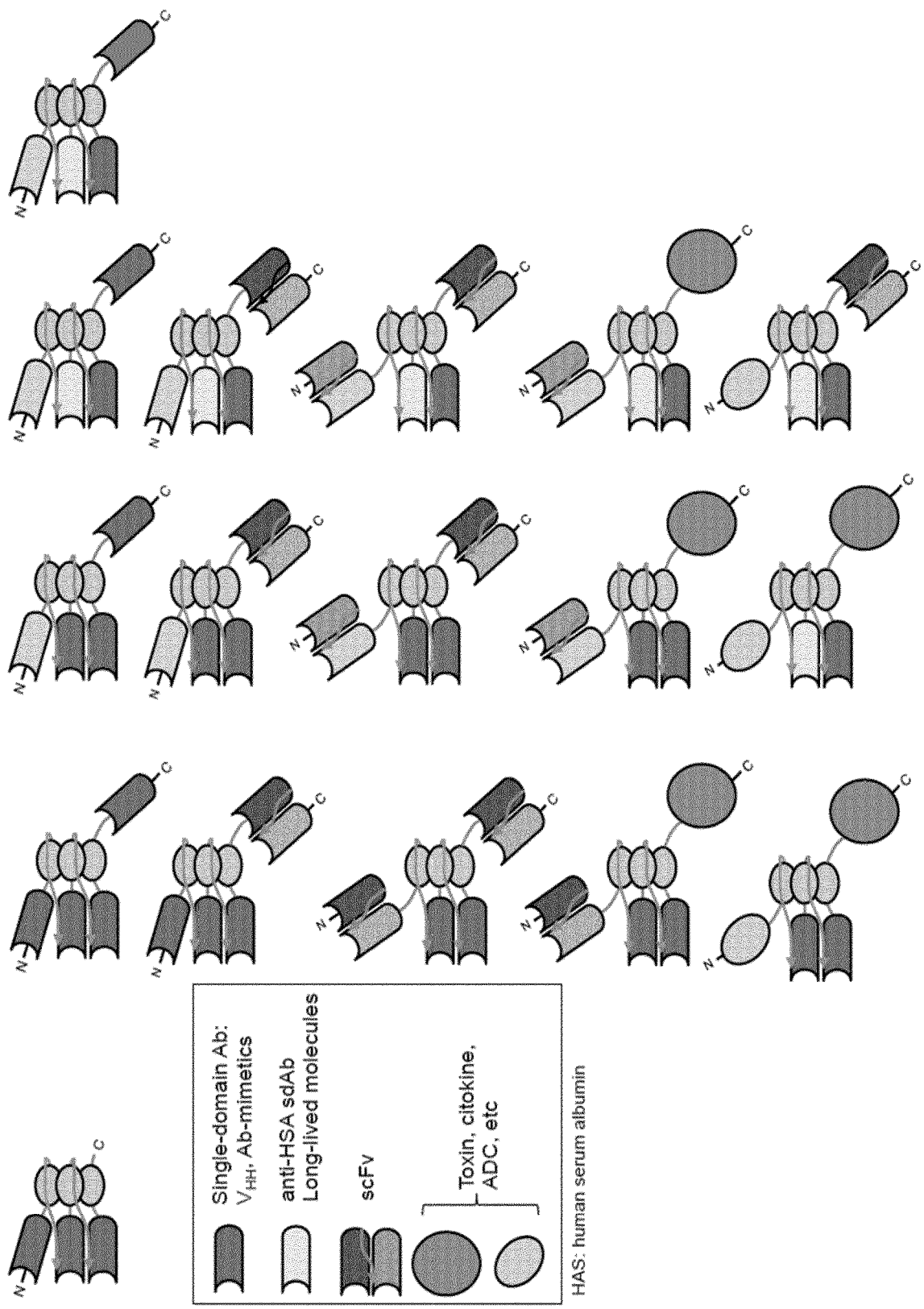
FIG. 10. Schematic diagrams showing the domain structure of non-limiting tandem trimerbodies, FIG. 11. Schematic diagrams showing the genetic (left) and domain structure (right) of the antibodies used in Example 2. Conventional multichain trimerbodies (A, B and C) bear a signal peptide from the oncostatin M (S), a $V_{HH}$ gene (A) or a scFv gene ($V_H$ and $V_L$ domains joined by a flexible linker) (B), or both (C) and one TIE domain (white box) flanked by flexible peptide linkers of different lengths (light grey boxes). Conventional tandem antibodies (D) bear a signal peptide from the oncostatin M (S), a $V_{HH}$ gene and a scFv gene joined by a five residues peptide linker (G₄S). Tandem $V_{HH}$-based trimerbodies (E and F) bear a signal peptide from the oncostatin M (S), three $V_{HH}$ genes and three TIE domains flanked by 7-mer (light grey boxes); and 17-mer and 21-mer (light grey boxes) flexible peptide linkers (E) and a scFv (F). Arrows indicate the direction of transcription. His6myc tag (T) appended was for immunodetection.

Non-limiting examples for illustration purposes only are provided in FIG. 10.

Preferably, at least one of said sdAbs is a $V_{HH}$ antibody, more preferably all the sdAbs molecules are $V_{HH}$ antibodies.

In a preferred embodiment, optionally in combination with one or more features of the embodiments described above or below, said molecule of formula (I) is selected from (i) to (viii) listed above, wherein L2, L4 and/or L6 have between 15 to 20 or 21 amino acids, preferably about 17 or about 21 amino acids. It is preferred that L1, L3 and/or L5 have from 4 or 5 to 10 amino acids, preferably around 7 amino acids; and L2, L4 and/or L6 have between 15 to 20 or 21 amino acids, preferably about 17 or about 21 amino acids.

More preferably, L2, L4 and/or L6 are selected from the group consisting of amino acid sequences SEQ ID NO:23 and SEQ ID NO:24. In a more preferred embodiment, said molecule of formula (I) is selected from (i) to (viii) listed above, wherein L1, L3 and/or L5 have amino acid sequence SEQ ID NO:22; and L2, L4 and/or L6 are selected from the group consisting of amino acid sequences SEQ ID NO:23 and SEQ ID NO:24.

In a particularly preferred embodiment, said molecule of formula (I) is a molecule according to (i) above, wherein:
L1, L3 and/or L5 have from 4 or 5 to 10 amino acids, preferably around 7 amino acids, more preferably are SEQ ID NO: 22; and
L2 and/or L4 have from 15 to 20 or 21 amino acids, preferably around 17 amino acids, more preferably are SEQ ID NO: 23.

In another particularly preferred embodiment, said molecule of formula (I) is a molecule according to (vi) above, wherein:
- L1, L3 and/or L5 have from 4 or 5 to 10 amino acids, preferably around 7 amino acids, more preferably are SEQ ID NO: 22;
- L2 and/or L4 have from 15 to 20 or 21 amino acids, preferably around 17 amino acids, more preferably are SEQ ID NO: 23; and
- L6 has from 15 to 20 or 21 amino acids, preferably around 21 aminoacids, and preferably is SEQ ID NO: 24.

In a particular embodiment, optionally in combination with one or more features of the embodiments described above or below, said molecule of formula (I) is multispecific, preferably bispecific, trispecific or tetraspecific.

B1 and B2 are sdAbs Directed Against the Same Antigen

In a particular embodiment, optionally in combination with the embodiments described above or below, B1 and B2 are sdAbs directed against the same antigen, preferably wherein said antigen is a target cell surface antigen.

In a preferred embodiment, optionally in combination with one or more features of the embodiments described above or below, A and/or D is a $V_{HH}$, AbM or scFv directed against the same antigen of B1 and B2, preferably wherein said antigen is a target cell surface antigen.

Preferably, said target cell surface antigen is a tumor-associated cell surface antigen or an immune function modulating antigen.

The term "tumor antigen," or "tumor-associated cell surface antigen" as used herein includes any molecule that is differentially expressed on a tumor cell compared to a normal cell. In some embodiments, the molecule is expressed at a detectably or significantly higher or lower level in a tumor cell compared to a normal cell. In other embodiments, the molecule exhibits a detectably or significantly higher or lower level of biological activity in a tumor cell compared to a normal cell. In some embodiments, the molecule is known or thought to contribute to a tumorigenic characteristic of the tumor cell. Numerous tumor antigens are known in the art. Whether a molecule is a tumor antigen can also be determined according to techniques and assays well known to those skilled in the art, such as for example clonogenic assays, transformation assays, in vitro or in vivo tumor formation assays, gel migration assays, gene knock-out analysis, etc.

In a particular embodiment, optionally in combination with one or more features of the embodiments described above or below, A, B1 and B2 are sdAbs against the same target cell surface antigen and D is a $V_{HH}$, AbM or scFv against a T-cell surface antigen, preferably wherein said target cell surface antigen is Epidermal Growth Factor Receptor (EGFR) and said T-cell surface antigen is CD3.

Figure 11:
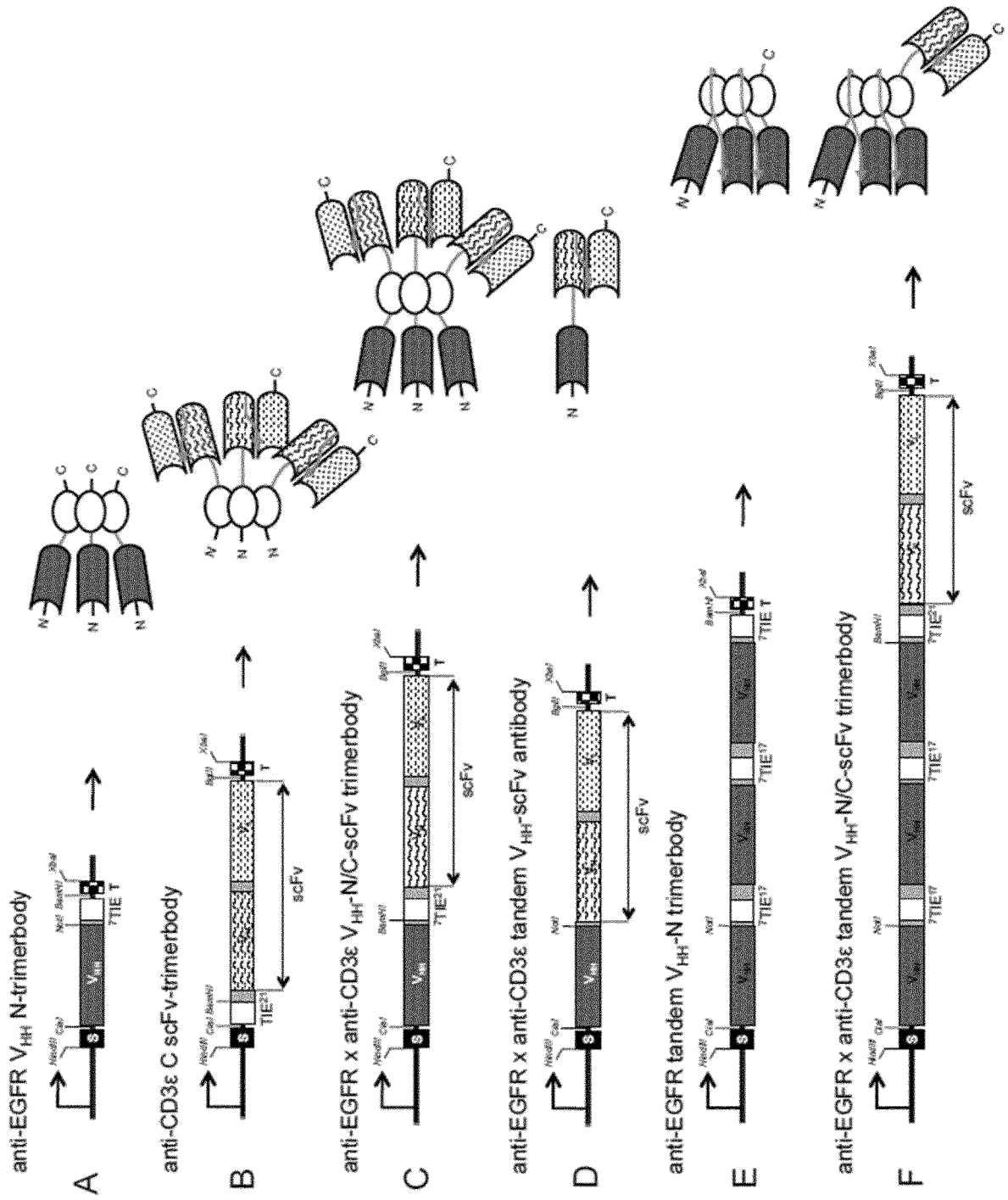

In a preferred embodiment, A, B1 and B2 are an anti-EGFR sdAb, preferably a $V_{HH}$ with amino acid sequence SEQ ID NO:18, and D is an anti-CD3 scFv with amino acid sequence SEQ ID NO:20, e.g., the anti-EGFR×anti-CD3c tandem $V_{HH}$-N/C-scFv trimerbody of FIG. 11.

In another particular embodiment, optionally in combination with one or more features of the embodiments described above or below, A is a $V_{HH}$, AbM or scFv directed against the same antigen of B1 and B2, wherein B1 and B2 are directed against the carcinoembryonic antigen (CEA).

In a preferred embodiment, A, B1 and B2 are an anti-CEA $V_{HH}$ with amino acid sequence SEQ ID NO:14, e.g., the monospecific ttαCEA of FIG. 1C.

In another particular embodiment, optionally in combination with one or more features of the embodiments described above or below, said molecule of formula (I) is bispecific, preferably wherein B1 and B2 are directed against the same antigen and A is a $V_{HH}$, AbM or scFv directed against a different antigen.

In a preferred embodiment, B1 and B2 are an anti-CEA $V_{HH}$ with amino acid sequence SEQ ID NO:14 and A is an anti-GFP $V_{HH}$ with amino acid sequence SEQ ID NO:16, e.g., the bispecific ttα-GFP-αCEA of FIG. 1C.

B1 and B2 are sdAbs Directed Against Different Antigens

In another particular embodiment, optionally in combination with one or more features of the embodiments described above or below, B1 and B2 are sdAbs directed against different antigens, preferably wherein at least one, more preferably all, of said antigens is a target cell surface antigen.

In a preferred embodiment, said molecule of formula (I) is trispecific, wherein B1 and B2 are sdAbs, wherein A is a $V_{HH}$, AbM or scFv, and wherein A, B1 and B2 are directed against different antigens, preferably wherein at least one, more preferably all, of said antigens is a target cell surface antigen.

In a preferred embodiment, A is an anti-GFP $V_{HH}$ with amino acid sequence SEQ ID NO:16, B1 is an anti-EGFR $V_{HH}$ with amino acid sequence SEQ ID NO:18, and B2 is an anti-CEA $V_{HH}$ with amino acid sequence SEQ ID NO:14, e.g., the trispecific ttα-GFP-α-EGRF-αCEA of FIG. 1C.

In another preferred embodiment, said molecule of formula (I) is tetraspecific, wherein B1 and B2 are sdAbs, wherein A and D are $V_{HH}$, AbM or scFv, and wherein A, B1, B2 and D are directed against four different antigens, preferably wherein at least one, more preferably all, of said antigens is a target cell surface antigen.

In another particular embodiment, optionally in combination with one or more features of the embodiments described above or below, B1 and B2 are sdAbs directed against different antigens, wherein said antigens are the carcinoembryonic antigen (CEA) and the Epidermal Growth Factor Receptor (EGFR).

Nucleic Acid Sequences, Vectors and Cells of the Invention

In a second aspect, the invention relates to a nucleic acid sequence encoding a recombinant single-chain polypeptide according to formula (I) as defined under the first aspect of the invention.

In a particular embodiment, the invention relates to a polynucleotide sequence comprising said nucleic acid sequence encoding a recombinant single-chain polypeptide according to formula (I) as defined above operably linked to control sequences. Preferably, said nucleic acid is operably linked to at least one promoter, preferably to a eukaryotic promoter, i.e., which enables the expression of the inserted coding sequence in eukaryotic cells, for instance, in mammalian cells.

Preferably, the polynucleotide sequence comprising a nucleic acid sequence encoding a recombinant single-chain polypeptide according to formula (I) further comprises a signal peptide operably linked to said nucleotide acid sequence. The term "signal peptide" as used herein refers to an amino acid sequence which permits the secretion of a recombinant polypeptide from the cell and cleavage of the signal peptide. The signal peptide has typically from 15 to 30 amino acid residues but may have up to 50 amino acids, and is usually located at the amino-terminus. A person skilled in the art will know how to select the most appropriate signal peptide. The best choice for a signal peptide sequence may be the proteins native signal peptide unless truncations from the amino terminus are to be explored. In either case, testing a small panel of commonly utilized signal sequences may be desirable. A handful of efficient and well-described signal sequences include interleukin-2, CD5, the Immunoglobulin Kappa light chain, trypsinogen, serum albumin, and prolactin, although there are many others that have proved beneficial as well (Stern et al. Trends Cell Mol Biol 2:1-17; Kober et al., Biotechnol Bioeng 110:1164-1173). Preferably, said signal peptide is useful for the secretion of a recombinant polypeptide from a mammalian cell. In a preferred embodiment, optionally in combination with one or more features of the embodiments described above or below, the signal peptide is that from oncostatin M of SEQ ID NO: 33, used in the Examples. Genetic engineering techniques are well known in the art and are described in handbooks such as Sambrook et al, "Molecular Cloning: A Laboratory Manual" (4th.Ed.), Vols. 1-3, Cold Spring Harbor Laboratory Press (2012).

In a third aspect, the invention relates to a recombinant expression vector comprising a nucleic acid sequence as defined above. By "vector" is meant any genetic element, such as a plasmid, phage, transposon, cosmid, chromosome, virus, virion, etc., which is capable of replication when associated with the proper control elements and which can transfer gene sequences between cells.

In a forth aspect, the invention relates to a host cell comprising a nucleic acid or vector of the previous aspects of the invention. The expression vectors can be introduced into a host cell to produce the desired polypeptide. Systems for cloning and expression of a polypeptide in a variety of different host cells are well known in the art, these may be from eukaryotic or prokaryotic organisms (i.e., bacterial cells, such as *E. coli*). For cells suitable for producing antibodies, see for instance Gene Expression Systems, Academic Press, eds. Fernandez et al, 1999.

The polypeptides of formula I of the invention may be prepared through expression in any suitable polypeptide production system, such as bacterial, fungal, yeast, amphibian, insect, plant, avian or mammalian production system. These as well as suitable corresponding expression systems, vectors, host cells, regulatory elements, etc., will be known to the skilled person. Also it will be clear to the skilled person, that polypeptides of the invention can be prepared using techniques for peptide synthesis. For production on industrial scale, preferred heterologous hosts include strains of *E. coli, Pichia pastoris, S. cerevisiae* that are suitable for large scale expression/production/fermentation, and in particular for large scale pharmaceutical (i.e., GMP grade) expression/production/fermentation. Suitable examples of such strains will be clear to the skilled person.

In other preferred embodiments, said host cells are eukaryotic cells. A number of powerful eukaryotic expression systems are available for expression of secreted proteins and membrane-bound receptors including those that contain unique post-translational modifications. The most common eukaryotic expression platforms currently include yeast (e.g., *Pichia pastoris* and *Saccharomyces cerevisiae*), baculovirus expression vector systems (*Autographa californica* multiple nuclear polyhedrosis virus and insect cell hosts *Spodoptera frugiperda* (e.g., Sf9 and Sf21 cells) or *Trichoplusia ni*), and mammalian cell systems (including a variety of transformed and/or genetically modified cell lines). More preferably, said cells are mammalian cells, including simian, human, dog and rodent cells. Examples of human cells are PER.C6 cells (WO01/38362), MRC-5 (ATCC CCL-171), WI-38 (ATCC CCL-75), HEK-293 cells (ATCC CRL-1573), HeLa cells (ATCC CCL2), and fetal rhesus lung cells (ATCC CL-160). Examples of non-human primate cells are Vero cells (ATCC CCL81), COS-1 cells (ATCC CRL-1650) or COS-7 cells (ATCC CRL-1651). Examples of dog cells are MDCK cells (ATCC CCL-34). Examples of rodent cells are hamster cells, such as BHK21-F, HKCC cells, or CHO cells. Any protein compatible expression system may be used to produce the disclosed single-chain polypeptides of the invention. Suitable expression systems include transgenic animals described in Gene Expression Systems, Academic Press, eds. Fernandez et al., 1999.

In a preferred embodiment, the host cells are human cells or cell lines, preferably, HEK-293 cells.

A still further aspect provides a method comprising introducing the nucleic acid or expression vector of the invention into a host cell. The introduction may employ any available technique. For eukaryotic cells, suitable techniques may include calcium phosphate transfection, DEAE-Dextran, electroporation, Liposome-mediated transfection and transduction using retrovirus or other virus, e.g., vaccinia or, for insect cells, baculovirus. For bacterial cells, suitable techniques may include calcium chloride transformation, electroporation and transfection using bacteriophage. The Introduction of the nucleic acid into the cells may be followed by causing or allowing expression from the nucleic acid, e.g., by entering host cells under conditions for expression of the gene. Following production by expression an antibody may be isolated and/or purified using any suitable technique, then used as appropriate.

Medical Uses of the Invention

The invention further provides, a method of treatment of a disease or disorder, comprising administering to a subject in need of such treatment a therapeutically effective amount of a molecule of formula (I), a nucleic acid sequence, a vector or a cell according to the previous aspects of the invention. In a particular embodiment, said molecule, nucleic acid sequence, vector or cell is administered with a therapeutically effective amount of another drug, which is administered prior, concomitantly or after its administration. Said other drug may form part of the same composition, or be provided as a separate composition for administration at the same time or at a different time.

In a related aspect, the invention relates to a molecule of formula (I), a nucleic acid sequence, a vector or a cell according to the previous aspects of the invention, for use as a medicament, alone or as a combination therapy. The invention also relates to the use of a molecule of formula (I), a nucleic acid sequence, a vector or a cell according to the previous aspects of the invention in the manufacture of a medicament.

In a further aspect, the invention relates to a composition comprising a molecule of formula (I), a nucleic acid sequence, a vector or a cell of the invention. Preferably, said composition is a pharmaceutical composition further comprising a pharmaceutically acceptable excipient and/or carrier. The compositions may also contain other active compounds providing supplemental, additional, or enhanced therapeutic functions.

Pharmaceutically acceptable excipients include, but are not limited to a carrier or diluent, such as a gum, a starch (e.g. corn starch, pregeletanized starch), a sugar (e.g. lactose, mannitol, sucrose, dextrose), a cellulosic material (e.g. microcrystaline cellulose), an acrylate (e.g. polymethylacrylate), calcium carbonate, magnesium oxide, talc, or mixtures thereof; a binder (e.g. acacia, cornstarch, gelatin, carbomer, ethyl cellulose, guar gum, hydroxypropyl cellulose, hydroxypropyl methyl cellulose, povidone); a disintegrating agent (e.g. cornstarch, potato starch, alginic acid, silicon dioxide, croscarmelose sodium, crospovidone, guar gum, sodium starch glycolate), a buffer (e.g. Tris-HCl, acetate, phosphate) of various pH and ionic strength; and additive such as albumin or gelatin to prevent absorption to surfaces; a detergent (e.g. Tween 20, Tween 80, Pluronic F68, bile acid salts); a protease inhibitor; a surfactant (e.g. sodium lauryl sulfate); a permeation enhancer; a solubilizing agent (e.g. glycerol, polyethylene glycerol); an antioxidants (e.g. ascorbic acid, sodium metabisulfite, butylated hydroxyanisole); a stabilizer (e.g. hydroxypropyl cellulose, hydroxypropylmethyl cellulose); a viscosity increasing agent (e.g. carbomer, colloidal silicon dioxide, ethyl cellulose, guar gum); a sweetener (e.g. aspartame, citric acid); a preservative (e.g. thimerosal, benzyl alcohol, parabens); a lubricant (e.g. stearic acid, magnesium stearate, polyethylene glycol, sodium lauryl sulfate); a flow-aid (e.g. colloidal silicon dioxide), a plasticizer (e.g. diethyl phthalate, triethyl citrate); an emulsifier (e.g. carbomer, hydroxypropyl cellulose, sodium lauryl sulfate); a polymer coating (e.g. poloxamers or poioxamines); a coating and film forming agent (e.g. ethyl cellulose, acrylates, polymethacrylates); a pharmaceutically acceptable carrier for liquid formulations, such as an aqueous (water, alcoholic/aqueous solution, emulsion or suspension, including saline and buffered media) or non-aqueous (e.g., propylene glycol, polyethylene glycol, and injectable organic esters, such as ethyl oleate) solution, suspension, emulsion or oil; and a parenteral vehicle (e.g., for subcutaneous, intravenous, intraarterial, or intramuscular injection), including but not limited to, water, oils, saline solution, Ringer's dextrose, aqueous dextrose and other sugar solutions. A pharmaceutically acceptable excipient also includes excipients for nanoencapsulation purposes, such as a cationic polyelectrolyte (e.g. gelatin and an anionic polyelectrolyte (e.g. arabic gum).

A pharmaceutical composition is typically formulated to be compatible with its intended route of administration. Methods to accomplish the administration are known to those of ordinary skill in the art. These includes, for example, injections, by parenteral routes such as intravenous, intravascular, intraarterial, subcutaneous, intramuscular, intraperitoneal, intraventricular, intraepidural, or others as well as oral, nasal, ophthalmic, rectal or topical. Sustained release administration is also specifically contemplated, e.g., as depot injections or erodible implants. Localized delivery is particularly contemplated, e.g., as delivery via a catheter to one or more arteries, such as the renal artery or a vessel supplying a localized site of interest. In one embodiment, said pharmaceutical composition is for oral administration. In another embodiment, said pharmaceutical composition is for intravenous, intramuscular or subcutaneous infusion or injection.

Said pharmaceutical composition can be administered a single time. It may also be administered regularly throughout the course of the method of treatment, for example, one, two, three, four, or more times a day, weekly, bi-weekly, every three weeks or monthly. The pharmaceutical composition may also be administered continuously to the subject (e.g, intravenously or by release from an implant, pump, sustained release formulation, etc.). The dosage to be administered can depend on multiple factors, including the type and severity of the cancer and/or on the characteristics of the subject, such as general health, age, sex, body weight and tolerance to drugs and should be adjusted, as needed, according to individual need and professional judgment. The dosage may also vary depending upon factors, such as route of administration, target site, or other therapies administered. The skilled artisan will be able to determine appropriate doses depending on these and other factors. A therapeutically effective amount may include, but is not limited to, dosage ranges of about 0.1 mg/kg to about 100 mg/kg; about 0.25 mg/kg to about 10 mg/kg; about 0.5 mg/kg to 75 mg/kg; 1 mg/kg to about 50 mg/kg; 1 mg/kg to about 10 mg/kg; about 0.5 mg/kg to about 25 mg/kg; or about 1 mg/kg to about 5 mg/kg.

Therapeutic agents and methods of administration, dosages, etc., are well known to those of skill in the art (see for example, the "Physicians Desk Reference", Klaassen's "The Pharmacological Basis of Therapeutics", "Remington's Pharmaceutical Sciences", and "The Merck Index, Eleventh Edition", incorporated herein by reference), and may be combined with the invention in light of the disclosures herein. Some variation in dosage will necessarily occur depending on the condition of the subject being treated. The person responsible for administration will, in any event, determine the appropriate dose for the individual subject, and such individual determinations are within the skill of those of ordinary skill in the art.

The invention further provides a kit which comprises a dosage form of a molecule of formula (I), a nucleic acid sequence, a vector, a cell, composition or pharmaceutical composition of the invention; optionally with a dosage form of another drug; and instructions for the use thereof. The containers in which the compound or pharmaceutical composition is supplied can be any conventional container that is capable of holding the supplied dosage forms.

In a further aspect, the present invention also provides a molecule of formula (I), a nucleic acid sequence, a vector, a cell, or pharmaceutical composition of the invention, for use in a method of preventing or treating a disease selected from the group consisting of autoimmune diseases, cancer, inflammatory diseases, and other angiogenesis-related disorders.

The expression "angiogenesis related disease" relates to all those diseases where pathogenic angiogenesis occur i.e. when said process is harmful or undesirable, whether cancerous or not. The scope of the present invention thus excludes the treatment of angiogenesis in situations where it is necessary, such as wound healing. Diseases associated to an undesired angiogenesis which may be treated with the compounds in accordance with the present invention, without limitation, are inflammatory diseases, especially chronic inflammatory diseases such as rheumatoid arthritis, psoriasis, sarcoidosis and such like; autoimmune diseases; viral diseases; genetic diseases; allergic diseases; bacterial diseases; ophthalmological diseases such as diabetic retinopathy, premature retinopathy, proliferative atrial retinopathy, retinal vein oclusion, macular degeneration, senile discoid macular degeneration, neovascular ocular glaucoma, choroidal neovascularization diseases, retinal neovascularization diseases, rubeosis (angle neovascularization), corneal graft rejection, retrolental fibroplasia, epidermal keratoconjunctivitis, vitamin A deficiency, contact lens exhaustion, atopical keratitis, superior limbic keratitis, pterygium dry eye, Sjogrens syndrome, acne rosacea, phlyctenulosis, syphilis, mycobacterial infections, lipid degeneration, burns with corrosive substances, bacterial ulcers, mycotic ulcers, protozoan infections, Kaposi sarcoma, Mooren's ulcer, Terrien marginal degeneration, marginal keratolysis, scleritis, chronic retinal detachment and such like; atherosclerosis; endometriosis; obesity; cardiac insufficiency; advanced renal insufficiency; endotoxemia; toxic shock syndrome; meningitis; silicon-induced fibrosis; asbestos-induced fibrosis; apoplexia; periodontitis; gingivitis; macrocytic anaemia; refractory anaemia; 5q deletion syndrome; conditions where the vascularization is altered as infection by HIV, hepatitis, hemorrhagic telangiectasia or Rendu-Osler-Weber's disease.

In a particular embodiment, the disease associated to an undesired angiogenesis is a disease selected from cancer, rheumatoid arthritis, psoriasis, sarcoidosis, diabetic retinopathy, premature retinopathy, retinal vein occlusion, senile discoid macular degeneration, atherosclerosis, endometriosis and obesity, preferably cancer.

In another particular embodiment the diseases associated to an undesired angiogenesis are inflammatory diseases. "Inflammatory disease" is understood to be any disease where there is an excessive or altered inflammatory response that leads to inflammatory symptoms. Said inflammatory diseases which may be treated by compounds of the invention include, without limitation, Addison's disease, acne vulgaris, alopecia areata, amyloidosis, ankylosing spondylitis, ulcerations, aphthous stomatitis, arthritis, arteriosclerosis, osteoarthritis, rheumatoid arthritis, bronchial asthma, Bechet's disease, Boeck's disease, intestinal inflammatory disease, Crohn's disease, choroiditis, ulcerative colitis, celiac's disease, cryoglobulinemia, macular degeneration, dermatitis, dermatitis herpetiformis, dermatomyositis, insulin dependent diabetes, juvenile diabetes, inflammatory demyelinating disease, Dupuytren contracture, encephalomyelitis, allergic encephalomyelitis, endophthalmia, allergic enteritis, autoimmune enteropathy syndrome, erythema nodosum leprosum, ankylosing spondylitis, idiopathic facial paralysis, chronic fatigue syndrome, rheumatic fever, cystic fibrosis, gingivitis, glomerulonephritis, Goodpasture syndrome, Graves syndrome, Hashimoto's disease, chronic hepatitis, histiocytosis, regional ileitis, iritis, disseminated lupus erythematous, systemic lupus erythematous, cutaneous lupus erythematous, lymphogranuloma, infectious mononucleosis, miastenia gravis, transverse myelitis, primary idiopathic myxedema, nephrosis, obesity, sympathetic ophthalmia, granulomatous orchitis, pancreatitis, panniculitis, pemphigus vulgaris, periodontitis, polyarteritis nodosa, chronic polyarthritis, polymyositis, acute polyradiculitis, psoriasis, chronic obstructive pulmonary disease, purpura, gangrenous pioderma, Reiter's syndrome, diabetic retinopathy, rosacea, sarcoidosis, ataxic sclerosis, progressive systemic sclerosis, scleritis, sclerodermia, multiple sclerosis, disseminated sclerosis, acute anterior uveitis, vitiligo, Whipple's disease, diseases associated to AIDS, severe combined immunodeficiency and Epstein Barr's virus such as Sjogren's syndrome, osteoarticular tuberculosis and parasitic diseases such as leishmaniasis. Preferred inflammatory diseases are rheumatoid arthritis, psoriasis, sarcoidosis, diabetic retinopathy, macular degeneration, arteriosclerosis and obesity.

The term "cancer" as used herein refers to the physiological condition in mammals that is typically characterized by unregulated cell growth/proliferation and includes tumors, neoplasias, and any other malignant disease having as cause malignant tissue or cells. Examples of cancer include but are not limited to, carcinoma, lymphoma, blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, myeloma (e.g., multiple myeloma), hepatocellular cancer, gastrointestinal cancer, pancreatic cancer, glioblastoma/glioma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma and various types of head and neck cancer.

An "autoimmune disease" herein is a non-malignant disease or disorder arising from and directed against an individual's own tissues. The autoimmune diseases herein specifically exclude malignant or cancerous diseases or conditions, especially excluding B cell lymphoma, acute lymphoblastic leukemia (ALL), chronic lymphocytic leukemia (CLL), Hairy cell leukemia and chronic myeloblastic leukemia. Examples of autoimmune diseases or disorders include, but are not limited to, inflammatory responses such as inflammatory skin diseases including psoriasis and dermatitis (e.g. atopic dermatitis); systemic scleroderma and sclerosis; responses associated with inflammatory bowel disease (such as Crohn's disease and ulcerative colitis); respiratory distress syndrome (including adult respiratory distress syndrome; ARDS); dermatitis; meningitis; encephalitis; uveitis; colitis; glomerulonephritis; allergic conditions such as eczema and asthma and other conditions involving infiltration of T cells and chronic inflammatory responses; atherosclerosis; leukocyte adhesion deficiency; rheumatoid arthritis; systemic lupus erythematosus (SLE); diabetes mellitus (e.g. Type I diabetes mellitus or insulin dependent diabetes mellitis); multiple sclerosis; Reynaud's syndrome; autoimmune thyroiditis; allergic encephalomyelitis; Sjorgen's syndrome; juvenile onset diabetes; and immune responses associated with acute and delayed hypersensitivity mediated by cytokines and T-lymphocytes typically found in tuberculosis, sarcoidosis, polymyositis, granulomatosis and vasculitis; pernicious anemia (Addison's disease); diseases involving leukocyte diapedesis; central nervous system (CNS) inflammatory disorder; multiple organ injury syndrome; hemolytic anemia (including, but not limited to cryoglobinemia or Coombs positive anemia); myasthenia gravis; antigen-antibody complex mediated diseases; anti-glomerular basement membrane disease; antiphospholipid syndrome; allergic neuritis; Graves' disease; Lambert-Eaton myasthenic syndrome; pemphigoid bullous; pemphigus; autoimmune polyendocrinopathies; Reiter's disease; stiff-man syndrome; Behcet disease; giant cell arteritis; immune complex nephritis; IgA nephropathy; IgM polyneuropathies; immune thrombocytopenic purpura (ITP) or autoimmune thrombocytopenia etc.

Other Uses of the Invention

In a related aspect, the invention relates to the use of a molecule of formula (I), a nucleic acid sequence, a vector or a cell according to the previous aspects of the invention, in the manufacturing of a diagnostic kit or as imaging reagent, alone or in combination with other chemical moieties. The invention also relates to the use of a molecule of formula (I), a nucleic acid sequence, a vector or a cell according to the previous aspects of the invention.

In some embodiments, a molecule of formula (I) is used in immunoassays (e.g., radioimmunoassays or ELISA assays) for diagnostic purposes in vitro. In a more particular embodiment, the molecule of formula (I) of the invention is labeled with a suitable marker, such as a fluorescent, chemoluminiscent, isotope marker etc.

In other embodiments, a molecule of formula (I) is labeled for in vivo imaging. In one particular embodiment, the molecule of formula (I) is labeled with a radiotracer for Nuclear Imaging. In another embodiment, the antibodies are labeled with a magnetic contrast agent for Magnetic Resonance Imaging, such as a superparamagnetic contrast agent or a paramagnetic contrast agent.

The term "imaging" or "medical imaging" refers to any technique, method or process used to produce images of the human body for medical purposes. Preferred medical imaging techniques include Magnetic Resonance Imaging and Nuclear Imaging. Nuclear imaging methods typically use the properties of isotopes to visualize labeled molecules bound to the target cells or tissue. Suitable nuclear imaging methods include scintigraphy, PET (positron emission tomography) and SPECT (Single Photon Emission Computed Tomography).

A Process for the Production of a Molecule of Formula (I)

In another aspect, the invention relates to a process for the production of a molecule of formula (I), comprising the steps of:
a. introducing a recombinant expression vector comprising a nucleic acid sequence of the invention into an appropriate host cell;
b. culturing the host cell in conditions which enable expression of the nucleic acid sequence,
c. optionally, isolating and/or purifying the expressed polypeptide.

A person skilled in the art will know the most appropriate culture conditions according to the host cell. Examples of host cells have been provided above.

Typically cells are cultured in a cell culture medium under appropriate temperature and atmosphere conditions (e.g., 37° C. and 5% $CO_2$ for mammalian cells). By "cell growth medium" or "cell culture medium" it is meant a nutritive solution for culturing or growing cells. The ingredients that compose such media may vary depending on the type of cell to be cultured. In addition to nutrient composition, osmolarity and pH are considered important parameters of culture media.

Depending on the host cell, this culture media may be a "microbiological media" which refers to any suitable substrate for the growth and reproduction of microorganisms, such as bacteria or fungi. The most common growth media for microorganisms are nutrient broths (liquid nutrient medium) or LB medium (lysogeny broth). Liquid media are often mixed with agar and poured via a sterile media dispenser into Petri dishes to solidify. A person skilled in the art will understand that the term "microbiological media" encompasses solid plated media, as well as semi-solid and liquid microbial growth systems.

The cell growth medium comprises a number of ingredients well known by the man skilled in the art, which typically for the culturing of eukaryotic cells includes amino acids, vitamins, organic and inorganic salts, sources of carbohydrate, lipids, trace elements (CuSO4, FeSO4, Fe(NO3)3, ZnSO4, etc), each ingredient being present in an amount which supports the cultivation of a cell in vitro (i.e, survival and growth of cells).

Ingredients may also include different auxiliary substances, such as buffer substances (like sodium bicarbonate, Hepes, Tris, etc.), oxidation stabilizers, stabilizers to counteract mechanical stress, protease inhibitors, animal growth factors, plant hydrolyzates, anti-clumping agents, anti-foaming agents. If required, a non-ionic surfactant, such as polypropylene glycol can be added to the cell growth medium as an anti-foaming agent. These agents are generally used to protect cells from the negative effects of aeration since, without an addition of a surfactant, the ascending and bursting air bubbles can lead to damage of those cells that are located on the surface of these air bubbles ("sparging").

The cell growth medium is preferably an animal serum-free mediums" (SFM), which meant that the cell growth medium is ready to use, that is to say that it does not required serum addition allowing cells survival and cell growth. The cell growth medium is preferably chemically defined, but it may also contained hydrolyzates of various origin, from plant for instance. Preferably, said cell growth medium is "non-animal origin" qualified, that is to say that it does not contain components of animal or human origin (FAO status: "free of animal origin"). Several media are commercial available and can be used. Media for the culturing of eukaryotic cells include, for example: Ham's F12 Medium (Sigma, St. Louis, Mo.), Dulbecco's Modified Eagles Medium (DMEM, Sigma), VP SFM (InVitrogen Ref 1 1681-020, catalogue 2003), Opti Pro (InVitrogen Ref 12309-019, 20 catalogue 2003), Episerf (InVitrogen Ref 10732-022, catalogue 2003), Pro 293 S-CDM (Cambrex ref 12765Q, catalogue 2003), LC17 (Cambrex Ref BESP302Q), Pro CHO 5-CDM (Cambrex ref 12-766Q, catalogue 2003), HyQ SFM4CHO (Hyclone Ref SH30515-02), HyQ SFM4CHO-Utility (Hyclone Ref SH30516.02), HyQ PF293 (Hyclone ref SH30356.02), HyQ PF Vero (Hyclone Ref SH30352.02), CDM4PERMAb (Hyclone Ref. 25 SH30871), or Excell media (SAFC).

Methods for polypeptide isolation and/or purification are well known in the art (see for instance, Isolation and Purification of Proteins, Feb. 5, 2003 by CRC Press, ISBN 9780824707262). Procedures for purification of polypeptides initially depend on the site of expression of the protein. Some proteins are secreted into the cell culture media; others are intracellular proteins. In the second instance, the first step of a purification process involves lysis of the cell, which can be done by a variety of methods, including mechanical shear, osmotic shock, or enzymatic treatments. Optionally, cell debris is removed by differential centrifugation or by filtration.

Once a clarified solution containing the polypeptide of interest has been obtained, its separation from the other proteins produced by the cell is usually attempted using a combination of different chromatography techniques. These techniques separate mixtures of proteins on the basis of their charge, degree of hydrophobicity, or size. Several different chromatography resins are available for each of these techniques, allowing accurate tailoring of the purification scheme to the particular protein involved. Affinity chromatography, which exploits a specific interaction between the protein to be purified and an immobilized capture agent, may also be an option for some polypeptides. Preferably, affinity chromatography is used for the purification of the polypeptide molecules of the invention.

In a particular embodiment, optionally in combination with one or more features of the embodiments described above or below, the invention relates to the process for the production of a molecule of formula (I), wherein the molecule of formula (I) is selected from the group consisting of:
i. a molecule wherein w, x, y and z are 0;
ii. a molecule wherein w and x are 1; y and z are 0, and A is a (poly)peptide;
iii. a molecule wherein z and y are 1; w and x are 0, and D is a (poly)peptide; and
iv. a molecule wherein w, x, y and z are 1, and A and D are a (poly)peptide; and
preferably, wherein for points ii), iii) and iv) A and/or D is part of the expressed polypeptide.

In a particular embodiment, optionally in combination with one or more features of the embodiments described above or below, the invention relates to the process for the production of a molecule of formula (I), wherein the molecule of formula (I) is selected from the group consisting of:
i. a molecule wherein w is 1, x is 0 and A is a moiety other than a poly(peptide); and/or
ii. a molecule wherein z is 1, y is 0 and D is a moiety other than a poly(peptide); and and the process further comprises covalently linking the expressed polypeptide to A and/or D. Preferably, to enable covalent linking either the expressed polypeptide or A and/or D are chemically modified.

Items of the Invention

1. A molecule according to formula (I) which comprises or consists of:

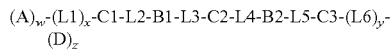

wherein B1 and B2 are monomeric single-domain polypeptides and at least one of B1 or B2 is a single-domain antibody (sdAb) or AbM;
wherein C1, C2 and C3 are collagen XV or collagen XVIII trimerizing structural elements (TSE);
wherein L1, L2, L3, L4, L5 and L6 are peptide linkers, and wherein L2 and L4 have a length from 5 to 40 amino acids;
wherein C1-L2-B1-L3-C2-L4-B2-L5-C3 is a recombinant single-chain polypeptide, C1 being located at the N-terminus of the polypeptide and C3 at the C-terminus of the polypeptide;
wherein w, x, y and z can be 1 or 0;
wherein when w is 1 and A is a moiety with binding, detection and/or effector properties, and then A is directly or indirectly covalently linked to the N-terminus of said single-chain polypeptide; and
wherein when z is 1 and D is a moiety with binding, detection and/or effector properties and then D is directly or indirectly covalently linked to the C-terminus of said single-chain polypeptide.

2. The molecule according to item 1, wherein when w is 1 and A is a (poly)peptide then x is 1, and when z is 1 and D is a (poly)peptide then y is 1.

3. The molecule according to any of items 1 or 2, wherein L2 and L4 have a length from 10 to 30 amino acids, preferably of around 20 amino acids.

4. The molecule according to any of items 1 to 3, wherein said TSE comprises or consists of the N-terminal trimerization region of collagen XV of SEQ ID NO: 1 or of collagen XVIII of SEQ ID NO: 2, preferably wherein said TSE comprises or consists of the N-terminal trimerization region of collagen XVIII of SEQ ID NO: 2.

5. The molecule according to any of items 1 to 4, wherein one or more of said peptide linkers is a flexible peptide linker which comprises 2 or more amino acids selected from the group consisting of Gly, Ser, Ala and Thr, preferably said peptide linkers contain repeats of amino acid residues, more preferably said repeats of amino acid residues are of Gly and Ser.

6. The molecule according to any of items 1 to 5, wherein one or more of the peptide linkers contain an amino acid sequence specifically cleavable by enzymatic or chemical means, preferably wherein one or more of the peptide linkers contain the recognition site for a peptidase, more preferably wherein said peptidase is a furin-like proprotein convertase.

7. The molecule according to any of items 1 to 6, wherein B1 and B2 are sdAbs or AbMs, preferably at least one of B1 or B2 is a $V_{HH}$ antibody, more preferably both are $V_{HH}$ antibodies.

8. The molecule according to any of items 1 to 7, wherein w is 1.

9. The molecule according to any of items 1 to 8, wherein z is 1.

10. The molecule according to any of items 1 to 9, wherein w and z are 1.

11. The molecule according to any of items 8 to 10, wherein A and/or D is a recombinant antibody, preferably a single-chain variable fragment (scFv), or an AbM.

12. The molecule according to any of items 8 to 9 or 11, wherein said molecule is selected from the group consisting of:
   i. a molecule wherein w and x are 1; A, B1 and B2 are sdAbs or AbMs; y is 0, and z is 0 or z is 1 when D is a moiety other than a (poly)peptide, preferably other than a recombinant antibody or an AbM;
   ii. a molecule wherein w and x are 1; A is a single-chain variable fragment (scFv), and B1 and B2 are sdAbs or AbMs; y is 0, and z is 0 or z is 1 when D is a moiety other than a (poly)peptide, preferably other than a recombinant antibody or an AbM;
   iii. a molecule wherein z and y are 1; D, B1, and B2 are sdAbs or AbMs; x is 0, and w is 0 or w is 1 when is a moiety other than a (poly)peptide, preferably other than a recombinant antibody or an AbM;
   iv. a molecule wherein z and y are 1; D is a scFv, and B1 and B2 are sdAbs or AbMs; x is 0, and w is 0 or w is 1 when A is a moiety other than a (poly)peptide, preferably other than a recombinant antibody or an AbM;
   v. a molecule wherein w, x, y and z are 1; and A, B1, B2 and D are sdAbs or AbMs;
   vi. a molecule wherein w, x, y and z are 1; and A, B1 and B2 are sdAbs or AbMs, and D is a scFv;
   vii. a molecule wherein w, x, y and z are 1; and D, B1 and B2 are sdAbs or AbMs, and A is a scFv;
   viii. a molecule wherein w, x, y and z are 1; and A and D are scFv and B1 and B2 are sdAbs or AbMs;
   ix. a molecule wherein w and x are 0; y and z are 1; B1 and B2 are sdAbs or AbMs; and D is a (poly)peptide other than scFv, sdAbs or AbMs;
   x. a molecule wherein y and z are 0; w and x, are 1; B1 and B2 are sdAbs or AbMs; and A is a (poly)peptide other than scFv, sdAbs or AbMs;
   xi. a molecule wherein w and z are 1; x and y are 0; B1 and B2 are sdAbs or AbMs; and A and D are moieties other than a (poly)peptide;
   xii. a molecule wherein w, x, y and z are 0; and B1 and B2 are sdAbs or AbMs.

13. The molecule according to item 12, wherein at least one of said sdAbs is a $V_{HH}$ antibody, preferably wherein all the sdAbs molecules are $V_{HH}$ antibodies.

14. The molecule according to any of items 1 to 13, wherein said molecule is multispecific, preferably wherein said molecule is bispecific, trispecific or tretraspecific.

15. The molecule according to any of items 1 to 14, wherein B1 and B2 are sdAbs directed against the same antigen, preferably wherein said antigen is a target cell surface antigen.

16. The molecule according to item 15, wherein A is a $V_{HH}$, AbM or scFv directed against the same antigen.

17. The molecule according to any of items 15 or 16, wherein D is a $V_{HH}$, AbM or scFv directed against a different antigen, preferably wherein said antigen is a target cell surface antigen.

18. The molecule according to item 15, wherein A is a $V_{HH}$, AbM or scFv directed against a different antigen, preferably wherein said antigen is a target cell surface antigen.

19. The molecule according to any of items 1 to 14, wherein B1 and B2 are sdAbs or AbMs directed against different antigens, preferably wherein at least one, more preferably all, of said antigens is a target cell surface antigen.
20. The molecule according to any of items 1 to 14, wherein said molecule is trispecific and wherein B1 and B2 are sdAbs or AbMs, wherein A is a $V_{HH}$, AbM or scFv, and wherein A, B1 and B2 are directed against different antigens, preferably wherein at least one, more preferably all, of said antigens is a target cell surface antigen.
21. The molecule according to any of items 1 to 14, wherein said molecule is tetraspecific and wherein B1, B2 are sdAbs or AbMs, wherein A and D are $V_{HH}$, AbM or scFv, and wherein A, B1, B2 and D are directed against four different antigens, preferably wherein at least one, more preferably all, of said antigens is a target cell surface antigen.
22. The molecule according to any of items 15 to 21, wherein said target cell surface antigen is a tumor-associated cell surface antigen or an immune function modulating antigen.
23. The molecule according to item 17, wherein A, B1 and B2 are sdAbs or AbMs against the same target cell surface antigen and D is a $V_{HH}$, AbM or scFv against a T-cell surface antigen, preferably wherein said target cell surface antigen is Epidermal Growth Factor Receptor (EGFR) and said T-cell surface antigen is CD3.
24. The molecule according to item 18, wherein B1 and B2 are directed against the carcinoembryonic antigen (CEA).
25. The molecule according to item 19, wherein said antigens are the carcinoembryonic antigen (CEA) and the Epidermal Growth Factor Receptor (EGFR).
26. The molecule according to item 10, wherein A and D are moieties other than a (poly)peptide, preferably other than recombinant antibodies or AbMs.
27. The molecule according to any of items 1 to 7, wherein w, x, y and z are 0.
28. A nucleic acid sequence encoding a recombinant single-chain polypeptide as defined in any of items 1 to 25.
29. A recombinant expression vector comprising a nucleic acid sequence of item 28.
30. A host cell comprising a vector of item 29.
31. A composition comprising a molecule according to any of items 1 to 27, a nucleic acid sequence according to item 28, a vector according to item 29 or a cell according to item 30.
32. A pharmaceutical composition comprising a molecule according to any of items 1 to 27, a nucleic acid sequence according to item 28, a vector according to item 29 or a cell according to item 30, and a pharmaceutically acceptable excipient.
33. A molecule according to any of items 1 to 27, a nucleic acid sequence according to item 28, a vector according to item 29, a cell according to item 30, or a composition according to item 31, for use as a medicament, alone or as a combination therapy.
34. A molecule according to any of items 1 to 27, a nucleic acid sequence according to item 28, a vector according to item 29, a cell according to item 30, or a composition according to item 31, for use in the treatment of cancer, alone or as a combination therapy.
35. A molecule according to any of items 1 to 27 a nucleic acid sequence according to item 28, a vector according to item 29, a cell according to item 30, or a composition according to item 31, for use in the treatment of an autoimmune disease, alone or as a combination therapy.
36. A process for the production of a molecule of formula (I) as defined in item 1, comprising the steps of:
  a. introducing a recombinant expression vector comprising a nucleic acid sequence as defined in item 28 into an appropriate host cell;
  b. culturing the host cell in conditions which enable expression of the nucleic acid sequence,
  c. optionally, isolating and/or purifying the expressed polypeptide.
37. The process according to item 35, wherein the molecule of formula (I) is selected from the group consisting of:
  i. a molecule wherein w, x, y and z are 0;
  ii. a molecule wherein w and x are 1; y and z are 0, and A is a (poly)peptide;
  iii. a molecule wherein z and y are 1; w and x are 0, and D is a (poly)peptide; and
  iv. a molecule wherein w, x, y and z are 1, and A and D are a (poly)peptide; and
preferably, wherein for points ii), iii) and iv) A and/or D is part of the expressed polypeptide.
38. The process according to item 35, wherein the molecule of formula (I) is selected from the group consisting of:
  i. a molecule wherein w is 1, x is 0 and A is a moiety other than a poly(peptide); and/or
  ii. a molecule wherein z is 1, y is 0 and D is a moiety other than a poly(peptide); and
and the process further comprises covalently linking the expressed polypeptide to A and/or D.
39. The process according to item 37, wherein to enable covalent linking either the expressed polypeptide or A and/or D are chemically modified.
40. Use of a molecule according to any of items 1 to 27 for the targeted delivery of a therapeutic and/or diagnostic moiety.

It is contemplated that any embodiment discussed in this specification can be implemented with respect to any medical use, pharmaceutical composition, kit, method of treatment, method of manufacturing a medicament and combination therapies of the invention, and vice versa. It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" may mean "one," but it is also consistent with the meaning of "one or more," "at least one," and "one or more than one". The use of the term "another" may also refer to one or more. The use of the term "or" in the claims is used to mean "and/or" unless explicitly indicated to refer to alternatives only or the alternatives are mutually exclusive.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. As used herein, the phrase "consisting essentially of" limits the scope of a claim to the specified materials or steps and those that do not materially affect the basic and novel characteristic(s) of the claimed invention. As used herein, the phrase "consisting of" excludes any element, step, or ingredient not specified in the claim except for, e.g., impurities ordinarily associated with the element or limitation.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "around", "approximately" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" or "around" may vary from the stated value by ±1, 2, 3, 4, 5, 6, 7, 10, 12 or 15%.

EXAMPLES

Example 1. Intramolecular Trimerization, a Novel Strategy for Making Multispecific Antibodies with Controlled Orientation of the Antigen Binding Domains I. Materials & Methods
Reagents and Antibodies.

Bovine serum albumin (BSA) (catalog no. A9418) and pooled normal human serum (catalog no. H4522) were from Sigma-Aldrich (St. Louis, Mo., USA). Native human carcinoembryonic antigen (CEA) (catalog no. 219369) and recombinant green fluorescent protein (GFP) (catalog no. 14-392) expressed in E. coli, were from Merck Millipore (Billerica, Mass., USA). The human EGFR-Fc chimera (catalog no. 10001-H02H-50) was from Sino Biological (Beijing, P.R.China). The mAbs used included: mouse anti-c-myc clone 9E10 (catalog no. ab32) (Abcam, Cambridge, UK), mouse anti-human CD3ε clone OKT3 (Ortho Biotech, Bridgewater, N.J., USA), and fully human anti-human epidermal growth factor receptor (EGFR) panitumumab (Amgen, Thousand Oaks, Calif., USA). The polyclonal antibodies included: rabbit anti-GFP (catalog no. ab6556) (Abcam); phycoerytrin (PE)-conjugated goat F(ab')$_2$ fragment anti-mouse IgG, Fc specific, (catalog no. 115-116-146) (Jackson Immuno Research, Newmarket, UK); PE-conjugated goat F(ab')$_2$ fragment anti-human IgG (H&L) (catalog no. ab7006) (Abcam); horseradish peroxidase (HRP)-conjugated goat anti-mouse IgG, Fc specific, (catalog no. A0168) (Sigma-Aldrich); HRP-conjugated goat anti-rabbit IgG (catalog no. A8275) (Sigma-Aldrich); and IRDye800 conjugated donkey anti-mouse IgG (H&L) (catalog no. 610-732-002) (Rockland Immunochemicals, Gilbertsville, Pa., USA).

Cells and Culture Conditions.

HEK-293 (catalog no. CRL-1573) and HeLa cells (catalog no. CCL-2) were cultured in Dulbecco's modified Eagle's medium (DMEM) (Lonza, Walkersville, Md., USA) supplemented with 2 mM L-glutamine, 10% (vol/vol) heat inactivated Fetal Calf Serum (FCS) and antibiotics (all from Life Technologies, Carlsbad, Calif., USA) referred as to DMEM complete medium (DCM), unless otherwise stated. Jurkat clone E6-1 cells (TIB-152) were maintained in RPMI-1640 (Lonza) supplemented with 2 mM L-glutamine, heat-inactivated 10% FCS. All of these cell lines were obtained from the American Type Culture Collection (Rockville, Md., USA). All cell lines were routinely screened for the absence of mycoplasma contamination by PCR using the Mycoplasma Plus TM Primer Set (Stratagene, Cedar Creek, Tex., USA).

Construction of Expression Vectors.

The mammalian expression vector pCEP4-MFE23-NC1$^{ES-}$ encoding the CEA-specific MFE23 scFv-based N-terminal trimerbody has been previously described (Cuesta A M, et al., PLoS One 2009, 4:e5381). To construct the plasmids pCR3.1-CEA.1-TIE$^{17}$ and pCR3.1-CEA.1-TIE$^7$, two synthetic genes encoding the CEA-specific CEA.1 $V_{HH}$ gene (Cortez-Retamozo V et al., Cancer Res 2004, 64:2853-7) fused by a 17-mer or a 7-mer flexible linker to the N-terminus of the human TIE$^{XVIII}$ domain (CEA.1-TIE$^{17}$ and CEA.1-TIE$^7$) were synthesized by Geneart AG (Regensburg, Germany) and subcloned as NotI/BamHI into the vector pCR3.1-L36 (Sanz L et al., EMBO J 2003, 22:1508-17). To generate the plasmid pCR3.1-αGFP-TIE$^7$ the DNA fragment encoding the anti-GFP $V_{HH}$ (αGFP) (Rothbauer U, e al., Nat methods 2006, 3:887-9) was PCR amplified from pNVgfp (Salema V et al., PloS one 2013, 8:e75126), with primers ClaGFP (SEQ ID NO: 25: 5'-TGTTGCGGCCGCTAGGGAGACGGTGACCTGG-3') and NotGFP (SEQ ID NO: 26: 5"-GCCACATC-GATGGCTCAGGTGCAGCTGGTG-3). The ClaI/NotI-digested PCR fragment was ligated into the ClaI/NotI-digested backbone of plasmid pCR3.1-CEA.1-TIE$^7$. To generate the plasmid pCR3.1-EGa1-TIE$^7$ the DNA fragment encoding the anti-EGFR $V_{HH}$ (EGa1) (Hofman E G et al., J Cell Sci 2008, 121:2519-28) was PCR amplified from pNVEGa1, with primers ClaEGFR (SEQ ID NO: 27: 5"-GCATGATC-GATGATGGCTCAGGTGCAGCTCA-3') and NotEGFR (SEQ ID NO: 28: 5"-TTGTGCG GCCGCTGAGGA-GACGGTGACCTGGGT-3). The ClaI/NotI-digested PCR fragment was ligated into the ClaI/NotI-digested backbone of plasmid pCR3.1-CEA.1-TIE$^7$.

To construct the tandem anti-CEA $V_{HH}$-based trimerbody expression vector, a synthetic gene encoding two CEA.1-TIE$^7$ constructs connected by a 17-mer flexible linker ($^{17}$CEA.1$^7$TIE$^{17}$CEA.1$^7$TIE) was synthesized by Geneart AG. The NotI cleaved fragment was ligated into pCR3.1-CEA.1-TIE[7] to obtain the plasmid pCR3.1-scCEA.1-TIE. To generate the single-chain bispecific [αGFP×αCEA (×2)] $V_{HH}$-based trimerbody expression vector, the NotI cleaved [17]CEA.1[7]TIE[17]CEA.1[7]TIE gene was ligated into the NotI-digested backbone of plasmid pCR3.1-aGFP-TIE[7] to obtain the plasmid pCR3.1-scaGFP-CEA.1(×2)-TIE. To generate the single-chain trispecific anti-GFP×anti-EGFR×anti-CEA $V_{HH}$-based trimerbody expression vector the DNA fragment encoding the EGa1 $V_{HH}$ was PCR amplified from pNVEGa1, with primers XmaEGFR (SEQ ID NO: 29: 5"-GCATGCTCGAGGTATGGCTCAGGTGCAGCTCA-3') and XhoEGFR (SEQ ID NO: 30: 5"-TTCCCGGGT-GAGGAGACGGTGACCTGGGTCC-3). The XhoI/XmaI-digested PCR fragment was ligated into the XhoI/XmaI-digested backbone of plasmid pCR3.1-scαGFP-CEA.1(×2)-TIE, to obtain the plasmid pCR3.1-scaGFP-EGa1-CEA.1-TIE. The sequences were verified using primers FwCMV (SEQ ID NO: 31: 5"-CGCAAATGGGCGG TAGGCGTG-3') and RvBGH (SEQ ID NO: 32: 5"-TAGAA GGCACAGTCGAGG-3).

Antibody Fragment Sequences

```
anti-CEA1 V_HH (SEQ ID NO: 14):
MAQVQLVESGGGSVQAGGSLRLSCAASGDTYGSYWMGWFRQAPGKEREG

VAAINRGGGYTVYADSVKGRFTISRDTAKNTVYLQMNSLRPDDTADYYC

AASGVLGGLHEDWFNYWGQGTQVTVSS

Anti-CEA1 V_HH encoding sequence (SEQ ID NO: 15):
ATGGCTCAGGTGCAGCTGGTGGAGTCTGGGGGAGGCTCGGTGCAGGCTG

GAGGGTCTCTGAGACTCTCCTGTGCGGCCTCTGGAGACACCTACGGTAG

CTACTGGATGGGCTGGTTCCGCCAGGCTCCAGGGAAGGAGCGTGAGGGG

GTCGCAGCTATTAATAGGGGTGGTGGCTATACAGTCTACGCCGACTCCG

TGAAGGGCCGATTCACCATCTCCCGAGACACCGCCAAGAACACGGTGTA

TCTGCAAATGAACAGCCTGAGACCTGACGACACGGCCGACTATTACTGT

GCGGCTAGCGGGGTACTAGGTGGTTTACATGAGGACTGGTTTAACTACT

GGGGCCAGGGGACCCAGGTCACCGTCTcctca anti-GFP V_HH (SEQ ID NO: 16):
MAQVQLVESGGALVQPGGSLRLSCAASGFPVNRYSMRWYRQAPGKEREW

VAGMSSAGDRSSYEDSVKGRFTISRDDARNTVYLQMNSLKPEDTAVYYC

NVNVGFEYWGQGTQVTVSS

Anti-GFP V_HH encoding sequence (SEQ ID NO: 17):
ATGGCTCAGGTGCAGCTGGTGGAGTCTGGGGGAGCCTTGGTGCAGCCGG

GGGGGTCTCTGAGACTCTCCTGTGCAGCCTCTGGATTCCCCGTCAATCG

CTATAGTATGAGGTGGTACCGCCAGGCTCCAGGGAAGGAGCGCGAGTGG

GTCGCGGGTATGAGTAGTGCTGGTGATCGTTCAAGTTATGAAGACTCCG

TGAAGGGCCGATTCACCATCTCCAGAGACGACGCCAGGAATACGGTGTA

TCTGCAAATGAACAGCCTGAAACCTGAGGACACGGCCGTGTATTACTGT

AATGTCAATGTGGGCTTTGAGTACTGGGGCCAGGGGACCCAGGTCACCG

TCTCCTCA anti-EGFR V_HH (SEQ ID NO: 18):
MAQVQLQESGGGLVQPGGSLRLSCAASGRTFSSYAMGWFRQAPGKEREF

VAAIRWSGGYTYYTDSVKGRFTISRDNAKTTVYLQMNSLKPEDTAVYYC

AATYLSSDYSRYALPQRPLDYDYWGQGTQVTVSS anti-EGFR V_HH encoding sequence (SEQ ID NO: 19):
ATGGCTCAGGTGCAGCTGCAGGAGTCTGGGGGAGGATTGGTGCAGCCAG

GGGGCTCGCTGAGACTCTCCTGTGCAGCCTCTGGACGCACCTTCAGTAG

CTATGCCATGGGCTGGTTCCGCCAGGCTCCAGGGAAGGAGCGTGAGTTT

GTAGCAGCTATTAGGTGGAGTGGTGGTTACACATACTATACAGACTCCG

TGAAGGGCCGATTCACCATCTCCAGAGACAACGCCAAGACTACGGTGTA

TCTGCAAATGAACAGCCTGAAACCTGAGGACACGGCCGTTTATTACTGT

GCAGCAACATACCTGTCCTCGGACTATAGCCGCTATGCGTTGCCCCAAA

GGCCCTTGGACTATGACTACTGGGGCCAGGGGACCCAGGTCACCGTCTC

CTCA
```

Peptide Linker Sequences

```
V_HH-based tandem trimerbodies (tt) (FIG. 1C):
7-mer linker:
                                    (SEQ ID NO: 22)
GGGGSSG 17-mer linker:
                                    (SEQ ID NO: 23)
SGAGGSGGSSGSDGASG V_HH-based N-terminal trimerbodies (FIG. 1B):
7-mer linker:
                                    (SEQ ID NO: 22)
GGGGSSG 17-mer linker:
                                    (SEQ ID NO: 23)
SGAGGSGGSSGSDGASG scFv-based N-terminal trimerbody
(MFE23^N21, FIG. 1A):
21-mer linker:
                                    (SEQ ID NO: 24)
KNSGAGGSGGSSGSDGASGSR.
```

Expression and Purification of Recombinant Antibodies.

HEK-293 cells were transfected with the appropriate expression vectors using calcium phosphate (Compte M et al., Cancer Gene Ther 2007, 14:380-8) and selected in DCM with 500 μg/ml G-418 (Sigma-Aldrich) to generate stable cell lines. Supernatants from transiently and stably transfected cell populations were analyzed by ELISA, western blotting and FACS. Stably transfected cell lines were used to collect serum free conditioned medium that was dialyzed against PBS (pH 7.4) and loaded onto a HisTrap HP 1 ml column using and ÄKTA Prime plus system (GE Healthcare, Uppsala, Sweden). The purified proteins were dialyzed against PBS and stored at −80° C.

Western Blotting.

Samples were separated under reducing conditions on 12% Tris-glycine gels and transferred to nitrocellulose membranes (Life Technologies) and probed with anti-c-myc mAb, followed by incubation with an IRDye800-conjugated donkey anti-mouse IgG. Visualization and quantitative analysis of protein bands were carried out with the Odyssey infrared imaging system (LI-COR Biosciences, Lincoln, Nebr., USA).

ELISA.

The ability of $V_{HH}$-based trimerbodies to bind purified antigens (CEA or GFP) was studied by ELISA as described (Cuesta Á M, et al., PLoS One 2009, 4:e5381). Briefly, Maxisorp (NUNC Brand Products, Roskilde, Denmark) plates were coated with CEA (0.3 µg/well) or GFP (0.5 µg/well) and after washing and blocking with 200 µl 5% BSA in PBS, 100 µl of purified protein solution, or 100 µl of neat supernatant from transiently or stably transfected HEK-293 cells, were added and incubated for 1 hour at room temperature. After three washes, 100 µl of HRP-conjugated goat anti-mouse IgG were added for 1 h at room temperature, after which the plate was washed and developed. To demonstrate the simultaneous reactivity of the two antigen specificities present in the bispecific and in the trispecific tandem trimerbody a dual ELISA was performed. Briefly, Maxisorp plates were coated with CEA (0.3 µg/well) and after washing and blocking, 100 µl of purified protein solution, or 100 µl of neat supernatant from transiently or stably transfected HEK-293 cells, were added and incubated for 1 hour at room temperature. After washing, 100 µl of recombinant GFP (10 µg/ml) were added followed by 100 µl of rabbit anti-GFP antibody. After washing, 100 µl of HRP-conjugated goat anti-rabbit IgG were added for 1 hour at room temperature, after which the plate was washed and developed.

Flow Cytometry.

The ability of $V_{HH}$-based trimerbodies to bind to cell surface EGFR was studied by FACS as described previously (Blanco-Toribio A, et al. MAbs 2013, 5:70-9). Briefly, HeLa or Jurkat cells were incubated with supernatants or purified trimerbodies (10 µg/ml) and anti-c-myc mAb for 30 min. After washing, the cells were treated with appropriate dilutions of PE-conjugated goat F(ab')$_2$ anti-mouse IgG. The samples were analyzed with a Beckman-Coulter FC-500 Analyzer (Coulter Electronics, Hialeah, Fla., USA). Anti-CD3 (OKT3, mouse IgG2a) and anti-EGFR (panitumumab, human IgG2) mAbs were used as controls on FACS studies, using appropriate dilutions of PE-conjugated goat F(ab')$_2$ anti-mouse IgG and PE-conjugated goat F(ab')$_2$ anti-human IgG, respectively.

Cell Adhesion Assay.

96-well microtiter plates (Corning Costar, Cambridge, Mass., USA) were coated overnight at 4° C. with CEA (2 µg/well), GFP (0.5 µg/well) or LM111 (1 µg/well) and after washing and blocking with 200 µl 3% BSA-DMEM for 1 hour at 37° C., 100 µl of supernatant from transfected HEK-293 cells were added for 1 hour at 4° C. After washing aliquots of 5×10$^4$ Jurkat or HeLa cells were loaded per well in serum-free medium and incubated for 30 minutes in humidified 5% CO$_2$ atmosphere at 37° C. After washing 100 µl of substrate CellTiter-Glo (Promega, Madison, Wis., USA) were added per well, and the bioluminescence measured using a Tecan Infinite F200 µlate-reading luminometer (Tecan Trading AG, Switzerland).

Kinetic Data Acquisition Using Biolayer Interferometry.

Investigation of the kinetic characteristics of αCEA$^{N7}$ and ttαCEA trimerbodies was performed by loading four AR2G biosensors (Fortebio, Menlo Park, Calif., USA) with either purified trimerbody at 10 µg/ml in loading buffer (10 mM acetate, pH 6), for 30 minutes, to a signal of 4.69±0.06 nm for αCEA$^{N7}$ and 2.95±0.03 nm for ttαCEA. Following re-equilibration in kinetics buffer (0.1% BSA in PBS, 0.05% Tween20), association was measured over 2 hours against 50, 25 and 12.5 nM of CEA diluted in kinetics buffer, followed by 2 hours of dissociation in analyte-free kinetics buffer. The experiments were performed at 30° C. on an Octet RED96 instrument (Fortebio) while shaken at 1000 rpm. Sensorgrams obtained from individual biosensors were analyzed by local fitting to a 1:1 model with Octet Data Analysis software (Fortebio). The multispecificity of ttαGFP-αCEA$^{(1:2)}$ and ttαGFP-αEGFR-αCEA trimerbodies were demonstrated by measuring their simultaneous binding of multiple antigens. First, GFP was immobilized onto AR2G biosensors at 10 µg/mL in loading buffer, for 20 minutes, to a signal of 0.77±0.12 nm. The GFP-coated biosensors were loaded with ttαGFP-αCEA$^{(1:2)}$ or ttαGFP-αEGFR-αCEA trimerbodies at 30 nM for 1 hour in kinetics buffer. The trimerbody-loaded biosensors were then moved into wells containing 50 nM of CEA in kinetics buffer for 1 hour. Finally, the biosensors were moved into wells with 10 nM of EGFR in kinetics buffer for 1 hour, followed by 1 hour of dissociation in analyte-free kinetics buffer. For every step involving analyte (e.g. trimerbody, CEA, and EGFR), a control biosensor was included which was moved into an analyte-free well, and a trimerbody-free biosensor was used to monitor the non-specific binding of CEA and EGFR to the GFP-coated biosensor surface. BSA-coated biosensors gave no response against 30 nM of ttαGFP-αCEA$^{(1:2)}$ or ttαGFP-αEGFR-αCEA trimerbodies in kinetics buffer (data not shown).

Circular Dichroism (CD).

Circular dichroism measurements were performed with a Jasco J-810 spectropolarimeter (JASCO, Tokyo, Japan). The spectra were recorded on protein samples at 0.05 g/L in PBS using 0.2 cm path length quartz cuvettes at 25° C. Thermal denaturation curves from 10 to 95° C. were recorded on the same protein samples and cuvette by increasing temperature at a rate of 1° C./minute and measuring the change in ellipticity at 210 nm. The reported mid-point temperature of protein denaturation corresponds to the minima (or maxima) in the corresponding derivative curve.

Size Exclusion Chromatography-Multiangle Laser Light Scattering (SEC-MALLS).

Static light scattering experiments were performed at room temperature using a Superdex 200 10/300 GL column (GE HealthCare) attached in-line to a DAWN-HELEOS light scattering detector and an Optilab rEX differential refractive index detector (Wyatt Technology, Santa Barbara, Calif., USA). The column was equilibrated with running buffer (PBS+0.03% NaN$_3$, 0.1 µm filtered) and the SEC-MALLS system was calibrated with a sample of BSA at 1 g/L in the same buffer. Then 100 µL samples of the different antibodies at 0.8-0.5 g/L in PBS were injected into the column at a flow rate of 0.5 mL/min. Data acquisition and analysis were performed using ASTRA software (Wyatt Technology). The molar mass data shown in the figures were smoothed (the mass measured at the center of the peak changes by less than 0.5% after smoothing). Based on numerous measurements on BSA samples at 1 g/L under the same or similar conditions we estimate that the experimental error in the molar mass is around 5%.

Mass Spectrometry.

A 2 µl protein sample was desalted using ZipTip® C4 micro-columns (Millipore) and eluted with 0.5 µl SA (sinapinic acid, 10 mg/ml in [70:30] Acetonitrile: Trifluoroacetic acid 0.1%) matrix onto a GroundSteel massive 384 target (Bruker Daltonics, Billerica, Mass., USA). An Autoflex III MALDI-TOF/TOF spectrometer (Bruker Daltonics) was used in linear mode with the following settings: 5000-40000 Th window, linear positive mode, ion source 1:20 kV, ion source 2: 18.5 kV, lens: 9 kV, pulsed ion extraction of 120 ns, high gating ion suppression up to 1000 Mr. Mass calibration was performed externally with protein 1 standard calibration mixture (Bruker Daltonics). Data acquisition, peak peaking and subsequent spectra analysis was performed using FlexControl 3.0 and FlexAnalysis 3.0 software (Bruker Daltonics).

Analysis of the Active Surface.

The comparative analysis of the range of movement of the $V_{HH}$ domains between the trimerbody and the tandem trimerbody was performed through homology modeling with MODELLER (Sali A, Blundell T L., J Mol Biol 1993; 234:779-815.). The crystal structure of human collagen XVIII trimerization domain (Boudko S P, et al., J Mol Biol 2009, 392:787-802) deposited in the Protein Data Bank (Berman H M, et al., J Comput Aided Mol Des 2014, 28:1009-14) with entry 3HSH was used as template for the trimerization domain, and the crystal structure of one of the Fab fragments in PDB entry 2VXS (Gerhardt S, et al., J Mol Biol 2009, 394:905-21) for the $V_{HH}$, as previously described (Blanco-Toribio A, et al., MAbs 2013, 5:70-9). To analyze the space accessible to the $V_{HH}$ domains in each construct, a total of 150 highly optimized models where build for each, in which the relative position between the $V_{HH}$ and the trimerization domains was left loose, thus allowing the exploration of multiple configurations for the flexible linkers. Finally, all the models where aligned through the trimerization domain and the surface of all of them was merged and evaluated with Pymol (Schrodinger L. The PyMOL molecular graphics system, version 1.3 r1. 2010).

II. Results

Figure 2:
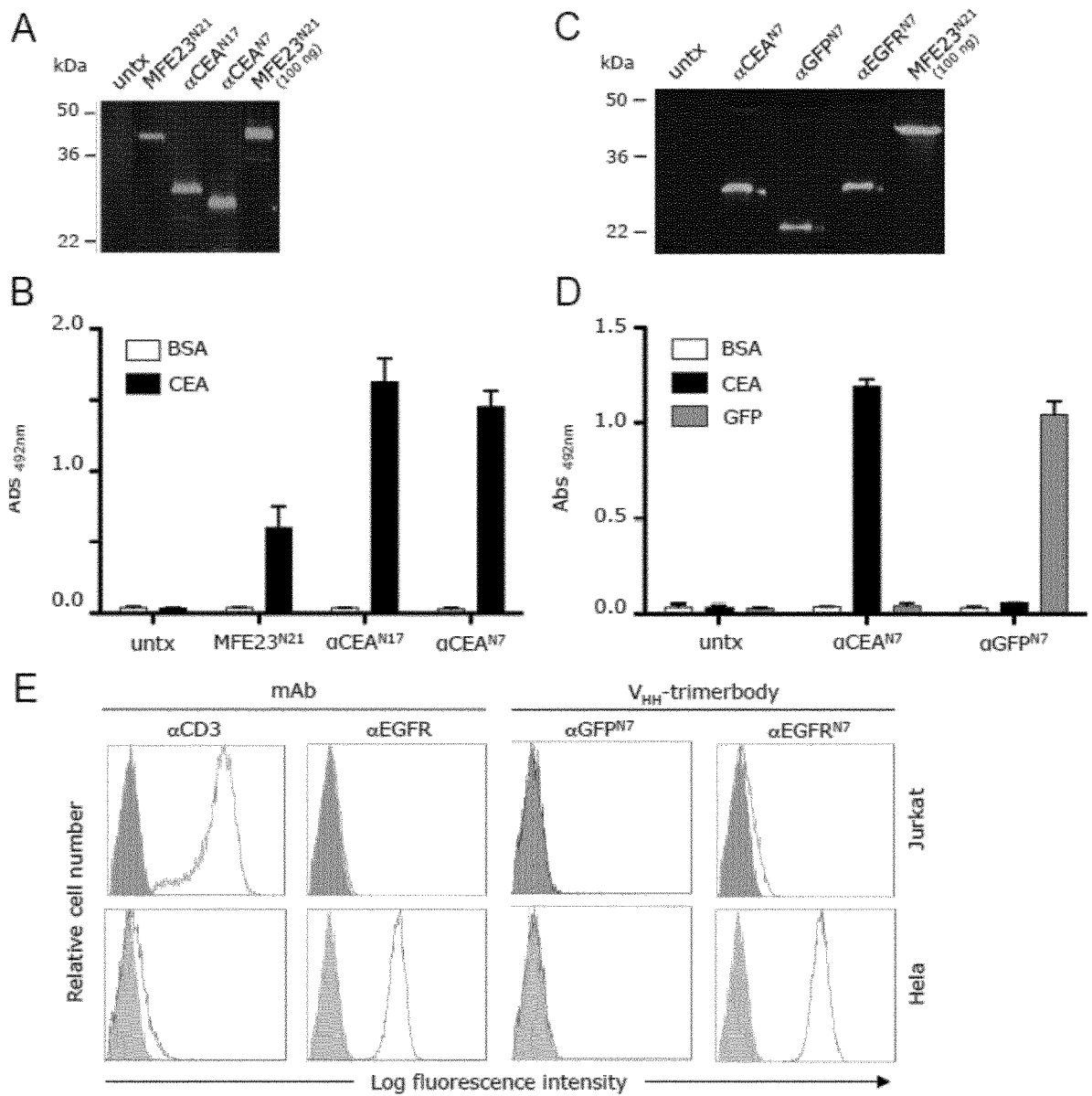
FIG. 2. Characterization of recombinant trimerbodies. The presence of secreted scFv-based and $V_{HH}$-based trimerbodies in the conditioned media from untransfected (untx) or transfected HEK-293 cells was demonstrated by western blot analysis (A and C). Migration distances of molecular mass markers are indicated (kDa). The blots were developed with anti-c-myc mAb, followed by incubation with an IRDye800-conjugated donkey anti-mouse IgG. The functionality of secreted trimerbodies was demonstrated, as described in the experimental procedures section, by ELISA against plastic immobilized CEA and GFP (B and D), and by FACS on EGFR-negative Jurkat cells and EGFR-positive HeLa cells (E), using 100 µl of neat supernatant from transiently transfected HEK-293 cells. Anti-CD3 (OKT3) and anti-EGFR (panitumumab) mAbs were used as controls on FACS studies.

Design and expression of $V_{HH}$-based N-terminal trimerbodies. In this study we generated N-terminal trimerbodies using single-domain antibody fragments ($V_{HH}$) as binding domains. We fused the CEA-specific CEA.1 $V_{HH}$ to the N-terminus of a TIE$^{XVIII}$ domain through flexible linkers of 17 or 7 residues ($\alpha CEA^{N17}$ or $\alpha CEA^{N7}$) (FIG. 1). Both constructs were produced in HEK-293 cells more efficiently than the anti-CEA scFv-based trimerbody (MFE23$^{N21}$) ($\alpha CEA^{N17}$, 2.2 µg/ml×10$^5$/48 h; $\alpha CEA^{N7}$ 2.9 µg/ml×10$^5$/48 h; MFE23$^{N21}$, 1.3 µg/ml×10$^5$/48 h). Western blot analysis under reducing conditions also showed a migration pattern of $\alpha CEA^{N17}$ and $\alpha CEA^{N7}$ consistent with the molecular weights calculated from their amino acid sequences (27.6 and 25.8 kDa, respectively) (FIG. 2A). ELISA analysis demonstrated that both $\alpha CEA^{N17}$ and $\alpha CEA^{N7}$ trimerbodies specifically recognize CEA (FIG. 2B).

To validate the ability of TIE domains to trimerize $V_{HH}$ antibodies with different specificities, we designed N-terminal trimerbody constructs bearing an anti-GFP $V_{HH}$ ($\alpha GFP$) or an anti-EGFR $V_{HH}$ ($\alpha EGFR$) fused to the N-terminus of a TIE$^{XVIII}$ domain through a 7-residue-long flexible linker (TIE$^{N7}$) Both $\alpha GFP^{N7}$ and $\alpha EGFR^{N7}$ constructs were secreted by transfected human HEK-293 cells, to similar levels as the $\alpha CEA^{N7}$ ($\alpha GFP^{N7}$, 1.9 µg/ml×10$^5$/48 h; $\alpha EGFR^{N7}$ 2.1 µg/ml×10$^5$/48 h). Western blot analysis, under reducing conditions, demonstrated that $\alpha GFP^{N7}$ and $\alpha EGFR^{N7}$ trimerbodies were single-chain type molecules with a migration pattern consistent with the molecular weights calculated from their amino acid sequences (22.4 and 27.1 kDa, respectively) (FIG. 2C).

ELISA analysis demonstrated that both secreted $\alpha CEA^{N7}$ and $\alpha GFP^{N7}$ trimerbodies specifically recognize their cognate antigens immobilized on plastic surface (FIG. 2D). The ability to detect antigen in a cellular context was studied by immunofluorescence labeling of human tumor cells (Jurkat or HeLa). Fluorescence staining was observed after incubation of the EGFR-expressing human cervix adenocarcinoma cell line HeLa with $\alpha EGFR^{N7}$, while no binding was detected for $\alpha GFP^{N7}$ (FIG. 2E). The EGFR-negative human T lymphoblastoid cell line Jurkat showed no binding of $\alpha EGFR^{N7}$ and $\alpha GFP^{N7}$ (FIG. 2E). These results demonstrated that the $V_{HH}$-based N-terminal trimerbodies recognized not only purified immobilized antigen, but also the antigen when expressed on the cell surface.

Design and Expression of Tandem $V_{HH}$-Based Trimerbodies.

Figure 3:
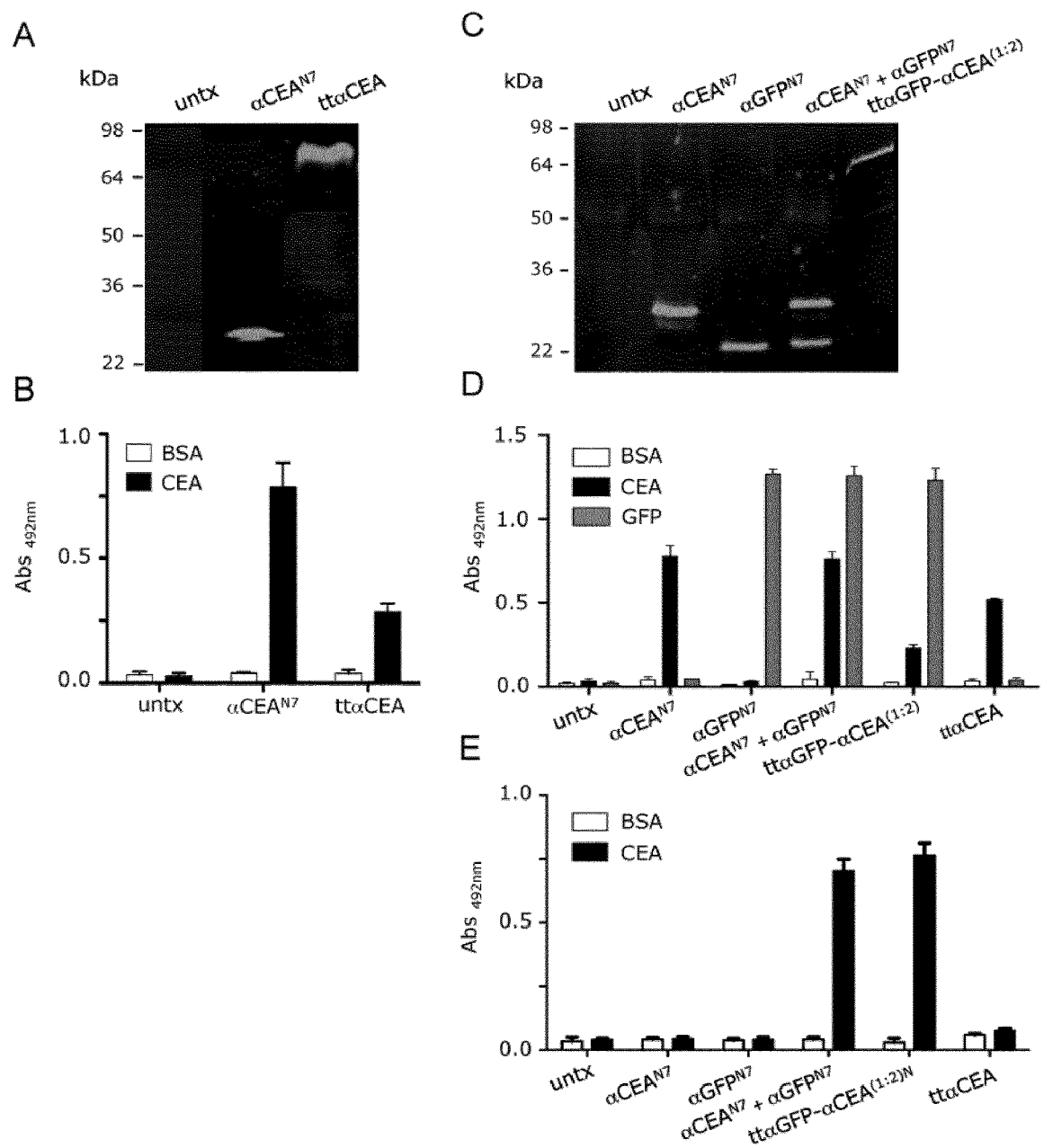
FIG. 3. Characterization of recombinant tandem $V_{HH}$-based trimerbodies. The presence of secreted multichain and tandem $V_{HH}$-based trimerbodies in the conditioned media from gene-modified HEK-293 cells was demonstrated by western blot analysis (A and C). Migration distances of molecular mass markers are indicated (kDa). The blots were developed with anti-c-myc mAb, followed by incubation with an IRDye800-conjugated donkey anti-mouse IgG. The functionality of secreted trimerbodies was demonstrated, as described in the experimental procedures section, by ELISA against plastic immobilized CEA and GFP (B and D), using 100 µl of neat supernatant from transiently transfected HEK-293 cells. Simultaneous binding to the two targets was assessed by dual ELISA by direct immobilization of CEA, followed by 100 µl of neat supernatant from gene-modified HEK-293 cells and addition of GFP (E). Data shown are from a representative experiment out of three independent ones.

Next, we designed a new $V_{HH}$-based monospecific trimerbody in a tandem format consisting of three $\alpha CEA^{N7}$ trimerbodies connected by two glycine-serine-based linkers on a single protein chain (FIG. 10). The anti-CEA tandem trimerbody (tt$\alpha$CEA) was secreted as soluble functional protein by transfected HEK-293 cells (0.8 µg/ml×10$^5$/48 h). Western blot analysis demonstrated that under reducing conditions the migration pattern of the secreted tt$\alpha$CEA is a single polypeptide chain with a molecular mass consistent with the 69.9 kDa calculated from its amino acid sequence (FIG. 3A). The functionality of tt$\alpha$CEA was demonstrated by ELISA against plastic immobilized CEA (FIG. 3B). The differences in the ELISA signals may be a result of the number of tags, three copies in the conventional multi-chain trimerbody ($\alpha CEA^{N7}$) and one copy in the tandem single-chain trimerbody (tt$\alpha$CEA) (FIGS. 1B and 1C).

To further assess the multivalency and multispecificity of tandem $V_{HH}$-based trimerbodies we designed a construct containing one copy of the $\alpha GFP^{N7}$ gene and two copies of the $\alpha CEA^{N7}$ gene connected by the described flexible linkers [tt$\alpha$GFP-$\alpha$CEA$^{(1:2)}$] (FIG. 10). This construct was produced as soluble functional protein by gene-mdified HEK-293 cells (1.3 µg/ml×10$^5$/48 h). Western blot analysis under reducing conditions demonstrated that tt$\alpha$GFP-$\alpha$CEA$^{(1:2)}$ is a single polypeptide chain with a molecular mass consistent with the 69.6 kDa calculated from its amino acid sequence (66.9 kDa without the signal sequence; FIG. 3C). The bispecificity of the tt$\alpha$GFP-$\alpha$CEA$^{(1:2)}$ was analyzed by ELISA using immobilized human CEA and GFP. Whereas the tt$\alpha$CEA showed specific binding to CEA, the tt$\alpha$GFP-$\alpha$CEA$^{(1:2)}$ showed binding to both antigens (FIG. 3D). Furthermore, when conditioned medium from cotransfected ($\alpha GFP^{N7}$ and $\alpha CEA^{N7}$) or single-transfected (tt$\alpha$GFP-$\alpha$CEA$^{(1:2)}$) HEK-293 cells was added to CEA-coated wells and, after washing, the CEA-bound trimerbodies were able to capture soluble GFP (FIG. 3E). Anti-CEA $V_{HH}$-based trimerbodies ($\alpha CEA^{N7}$ and tt$\alpha$CEA) were found to bind to CEA, but the bound trimerbodies did not capture soluble GFP (FIG. 3E).

Figure 4:
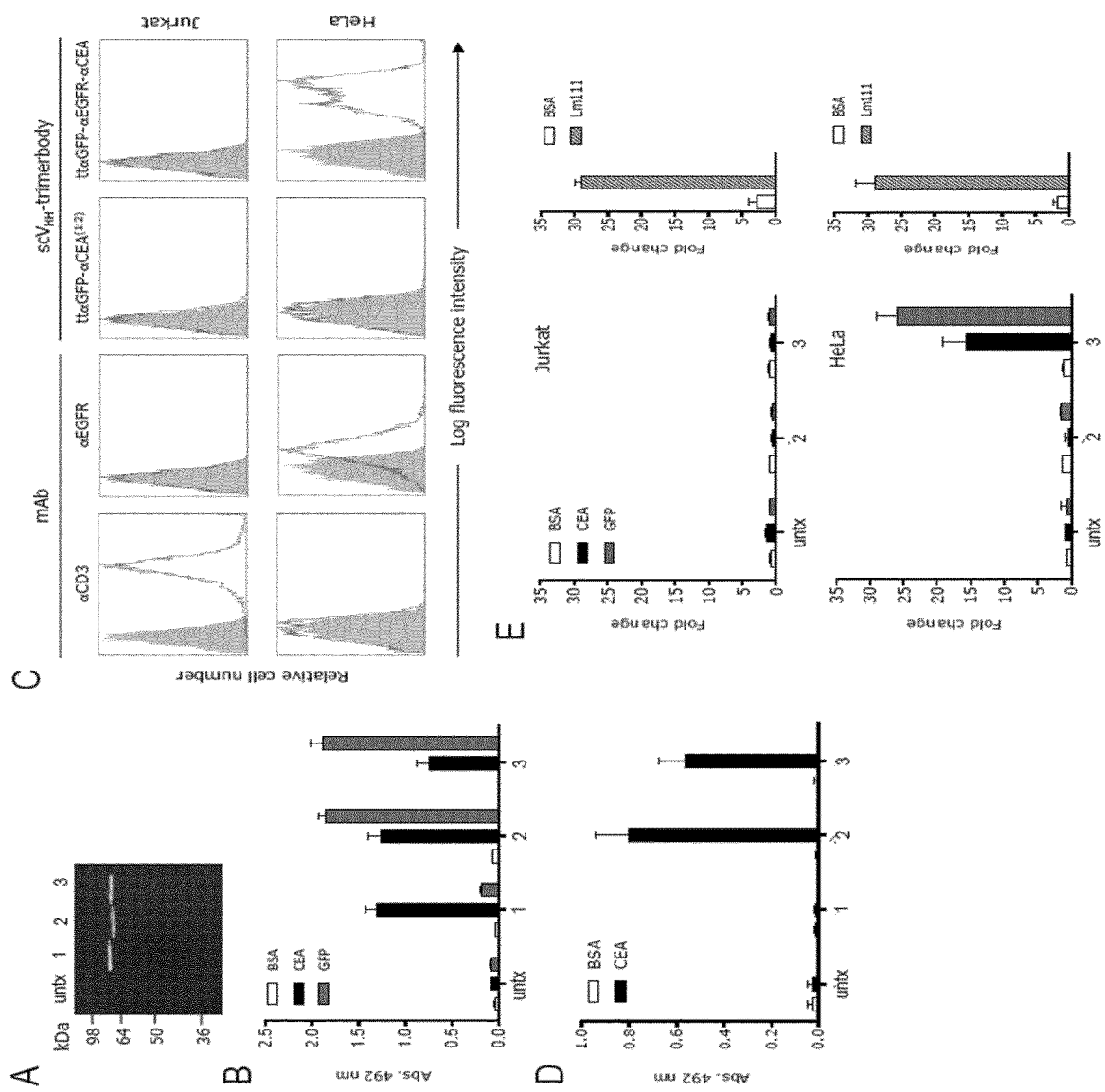
FIG. 4. Characterization of recombinant tandem $V_{HH}$-based trimerbodies: ttαCEA (1), ttαGFP-αCEA$^{(1:2)}$ (2) and ttαGFP-αEGFR-αCEA (3). The presence of secreted tandem $V_{HH}$-based trimerbodies in the conditioned media from gene-modified HEK-293 cells was demonstrated by western blot analysis (A). Migration distances of molecular mass markers are indicated (kDa). The blot was developed with anti-c-myc mAb, followed by incubation with an IRDye800-conjugated donkey anti-mouse IgG. The functionality of secreted tandem trimerbodies was demonstrated, as described in the experimental procedures section, by ELISA against plastic immobilized CEA and GFP (B), and by FACS on EGFR⁻ Jurkat cells and EGFR⁺ HeLa cells (C). Simultaneous binding to CEA and GFP was assessed by dual ELISA by direct immobilization of CEA, followed by 100 µl of neat supernatant from gene-modified HEK-293 cells and addition of GFP (D). Adhesion of EGFR⁻ Jurkat cells and EGFR⁺ HeLa cells to plastic-immobilized BSA, CEA or GFP, after incubation with 100 µl of neat conditioned media from gene-modified HEK-293 cells containing tandem $V_{HH}$-based trimerbodies: ttαGFP-αCEA$^{(1:2)}$ (2) and ttαGFP-αCEA-αEGFR (3). Adhesion of Jurkat and HeLa cells to plastic-immobilized laminin 111 (Lm111) was used as a control. Data are plotted as the log of fold change in adhesion relative to BSA. Data shown are from a representative experiment out of three independent ones.

In a further approach, we designed a tandem $V_{HH}$-based trimerbody construct containing three different $V_{HH}$ ($\alpha GFP^{N7}$, $\alpha EGFR^{N7}$ and $\alpha CEA^{N7}$) connected by the described flexible linkers [tt$\alpha$GFP-$\alpha$EGFR-$\alpha$CEA] (FIG. 1C). The trispecific tandem trimerbody was secreted by transfected HEK-293 cells (1.0 µg/ml×10$^5$/48 h). Western blot analysis under reducing conditions revealed that tt$\alpha$GFP-$\alpha$EGFR-$\alpha$CEA is a single polypeptide chain with a molecular mass consistent with the 72.2 kDa calculated from its amino acid sequence (68.5 without the signal sequence; FIG. 4A). Conditioned media from HEK-293 cells transfected with tt$\alpha$GFP-$\alpha$EGFR-$\alpha$CEA recognized GFP and CEA immobilized on plastic (FIG. 4B). Tandem trimerbodies were further analyzed by flow cytometry for binding to EGFR-negative and EGFR-positive tumor cell lines. Fluorescence staining was observed after incubation of EGFR-expressing HeLa cells with tt$\alpha$GFP-$\alpha$EGFR-$\alpha$CEA trimerbody, demonstrating its ability to detect the antigen in a cellular context (FIG. 4C). In contrast, incubation of HeLa cells with tt$\alpha$GFP-$\alpha$CEA$^{(1:2)}$ trimerbody or incubation of Jurkat cells with tt$\alpha$GFP-$\alpha$EGFR-$\alpha$CEA trimerbody revealed no staining (FIG. 4C). Conditioned medium from HEK-293 cells transfected with plasmids ttαGFP-αCEA$^{(1:2)}$ or ttαGFP-αEGFR-αCEA was added to CEA-coated wells and, after washing, the CEA-bound trimerbodies were able to capture soluble GFP (FIG. 4D). $V_{HH}$-based trimerbodies in the supernatant from HEK-293 transfected with plasmid encoding ttαCEA did not capture soluble GFP (FIG. 4D). To further assess the multivalency and multi-specificity of tandem $V_{HH}$-based trimerbodies we performed adhesion assays. As shown in FIG. 4E, EGFR-positive HeLa cells adhered to GFP- and CEA-coated wells after incubation with conditioned medium containing ttαGFP-αEGFR-αCEA. Moreover, trispecific tandem trimerbody was as efficient as laminin in supporting the adhesion of EGFR-positive cells. The adhesion of HeLa cells was specific since no adhesion of EGFR-negative Jurkat cells to GFP- and CEA-coated wells was detected (FIG. 4E). Furthermore, GFP- and CEA-coated wells, preincubated with conditioned medium from HEK-293 cells transfected with ttαGFP-αCEA$^{(1:2)}$ plasmids did not support any significant cell adhesion (FIG. 4E).

Purification and Characterization of $V_{HH}$-Based Trimerbodies.

Figure 5:
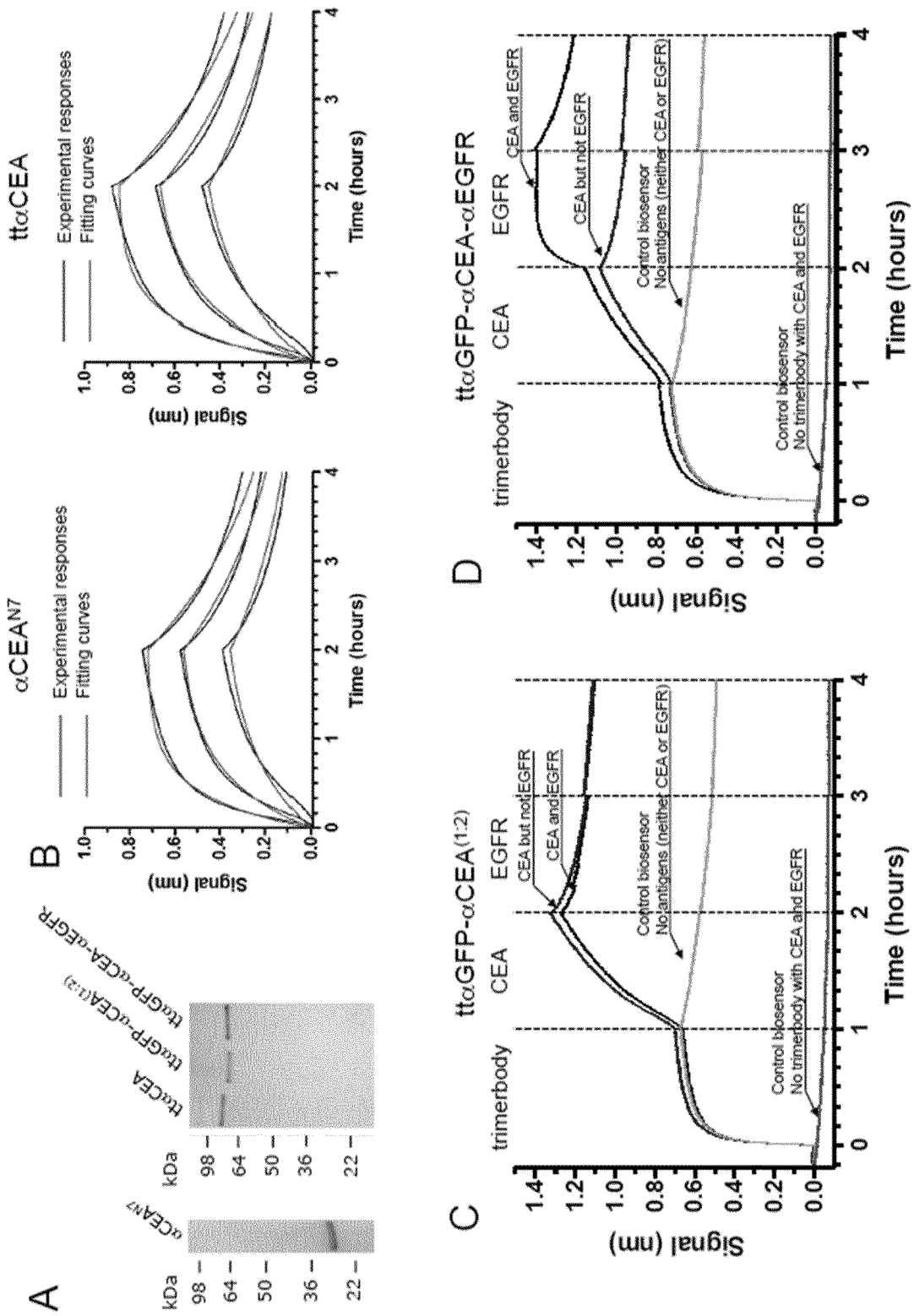
FIG. 5. Functional characterization of purified multi-chain (αCEA$^{N7}$) and tandem (ttαCEA, ttαGFP-αCEA$^{(1:2)}$ and ttαGFP-αCEA-αEGFR) $V_{HH}$-based trimerbodies. Reducing SDS-PAGE of the monospecific αCEA$^{N7}$ and ttαCEA, the bispecific ttαGFP-αCEA$^{(1:2)}$ and the trispecific ttαGFP-αCEA-αEGFR trimerbodies (A). Biolayer interferometry (BLI)-derived sensorgrams from the interactions between immobilized αCEA$^{N7}$ or ttαCEA trimerbody, and analyte CEA at 50, 25, or 12.5 nM. (B). The αCEA$^{N7}$ and ttαCEA fitting curves use a $k_a$ of $1.23*10^4 M^{-1} s^{-1}$ and $1.14*10^4 M^{-1} s^{-1}$, and a $k_d$ of $1.48*10^{-4} s^{-1}$ and $1.34*10^{-4} s^{-1}$, respectively. Concurrent binding of the ttαGFP-αCEA$^{(1:2)}$ and ttαGFP-αCEA-αEGFR trimerbodies to antigens measured using BLI (C-D). In these experiments, GFP was immobilized on the biosensors. Simultaneous binding of the bispecific ttαGFP-αCEA$^{(1:2)}$ trimerbody to GFP and human CEA (C). Concurrent binding of the trispecific ttαGFP-αCEA-αEGFR trimerbody to the three antigens: GFP, CEA and EGFR (D). Control biosensors were associated with trimerbody and CEA but not EGFR, with trimerbody but neither antigen or without trimerbody, with both CEA and EGFR.

The αCEA$^{N7}$ and the ttαCEA, ttαGFP-αCEA$^{(1:2)}$ and ttαGFP-αEGFR-αCEA trimerbodies were purified from conditioned medium by immobilized metal affinity chromatography, which yielded proteins that were >90% pure by reducing SDS-PAGE (FIG. 5A). The binding kinetics of the purified αCEA$^{N7}$ multi-chain trimerbody and ttαCEA tandem trimerbody were studied using biolayer interferometry (BLI). As shown in FIG. 5B, the kinetic behavior of the αCEA$^{N7}$ and ttαCEA interactions were highly similar, indicating that the additional glycine-serine linkers introduced in the tandem trimerbody do not compromise its antigen binding capacity. Sensograms obtained using 50, 25, and 12.5 nM of CEA could be fit to a 1:1 model using nearly identical kinetic rate constants for both trimerbodies (FIG. 5B), giving a $K_D$ of 12 nM for both the αCEA$^{N7}$ and ttαCEA interactions.

We next studied whether the binding sites of the purified ttαGFP-αCEA$^{(1:2)}$ and ttαGFP-αEGFR-αCEA trimerbodies can bind concurrently to their cognate antigens. Preliminary test binding experiments (data not shown) suggested that best binding responses are obtained when GFP is immobilized on AR2G biosensors. BLI-derived sensorgrams show a clear binding of both ttαGFP-αCEA$^{(1:2)}$ and ttαGFP-αEGFR-αCEA trimerbodies to GFP-coated biosensors (FIG. 5C-D). Both trimerbody-loaded biosensors give additional binding curves upon addition of CEA. The ttαGFP-αEGFR-αCEA-loaded biosensors give a third binding curve upon addition of EGFR (FIG. 5D). In the absence of ttαGFP-αCEA$^{(1:2)}$ and ttαGFP-αEGFR-αCEA trimerbodies, GFP-coated biosensors do not respond to CEA or hEGFR-Fc (FIG. 5C-D). These experiments show that the bispecific and trispecific tandem trimerbodies can simultaneously bind to all their cognate antigens.

Figure 6:
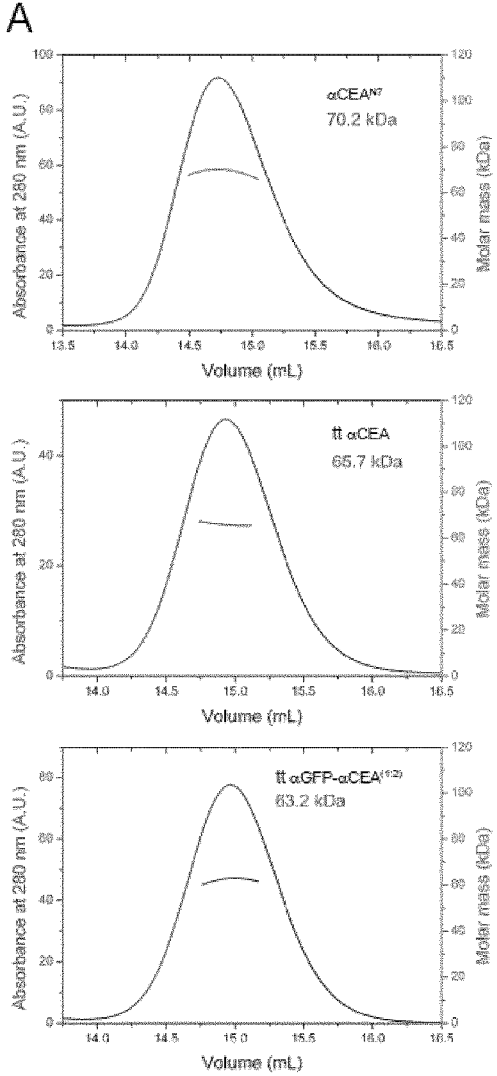
FIG. 6. Structural characterization of purified multi-chain (αCEA$^{N7}$) and tandem (ttαCEA and ttαGFP-αCEA$^{(1:2)}$ $V_{HH}$-based trimerbodies. Oligomeric analysis of the monospecific αCEA$^{N7}$ and ttαCEA and the bispecific ttαGFP-CEA$^{(1:2)}$ trimerbodies by SEC-MALLS with the indicated molecular masses measured at the center of the chromatography peaks (A). Secondary structure analysis by circular dichroism spectra (B) and tertiary structure analysis by thermal denaturation measured by the change in ellipticity at 210 nm for the three molecules (C).
Figure 6:
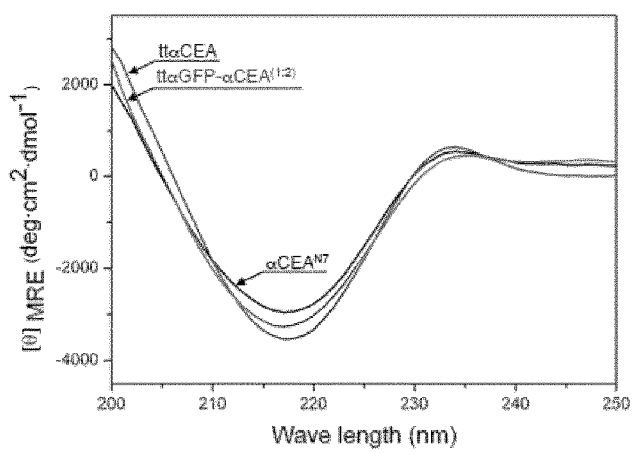
Figure 6:
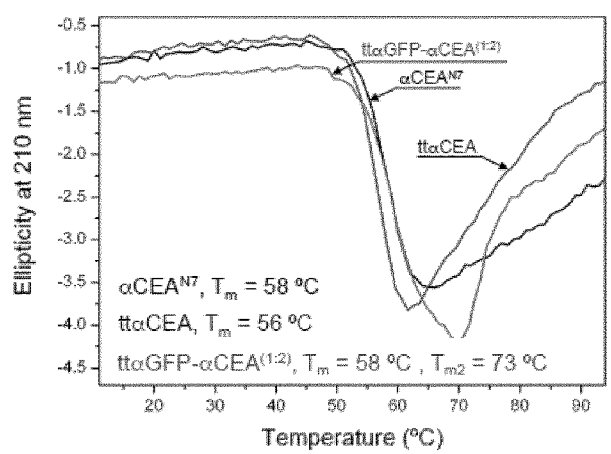
Figure 9:
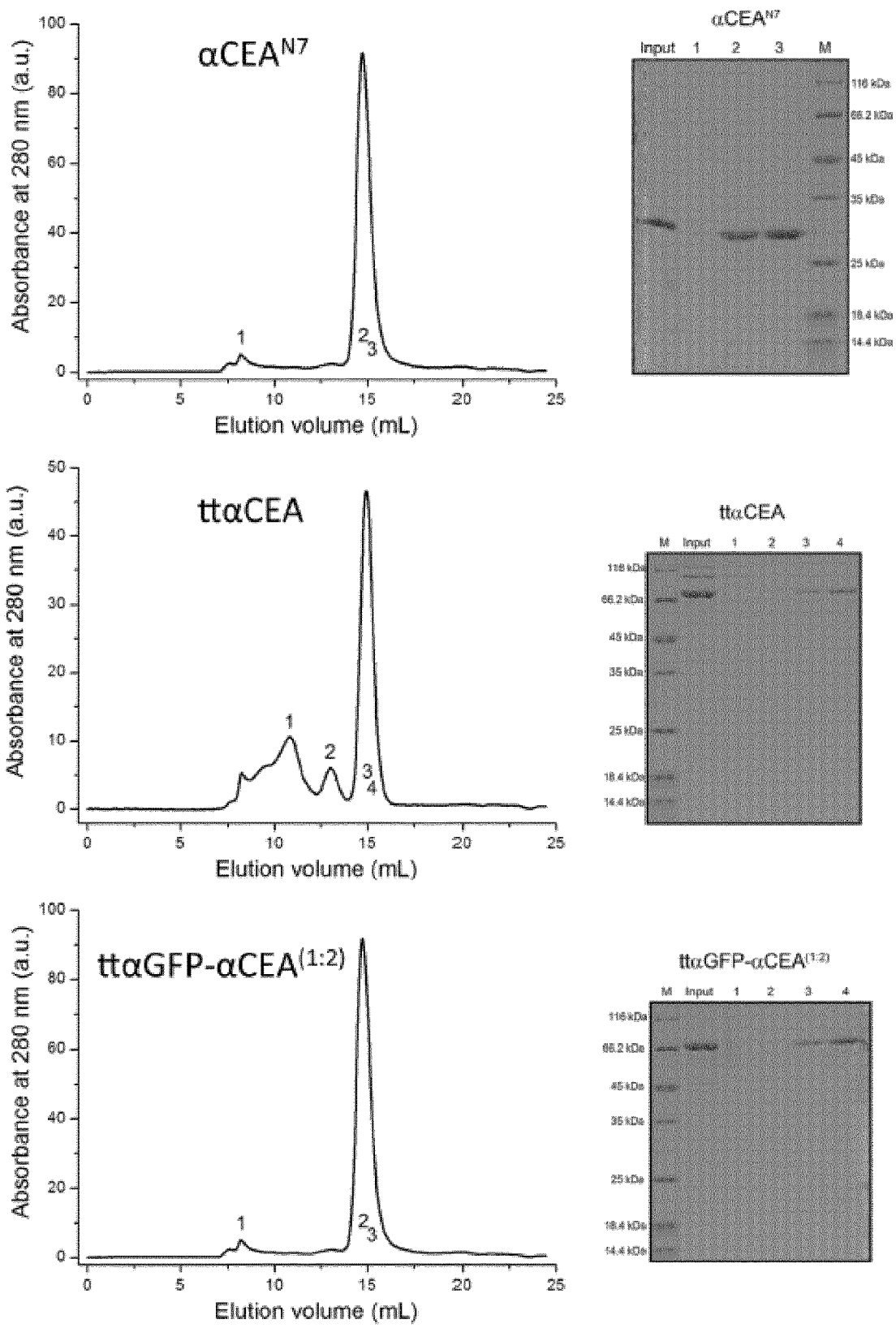
FIG. 9. Full scale chromatograms corresponding to FIG. 6 and SDS-PAGE analysis. The injected sample (Input), some of the collected fractions (lanes 1 to 4) and molecular weight markers (M) were run on a 12% acrylamide gel and stained with coomassie blue. The numbers on the chromatogram correspond to the position of the fractions that were loaded on the numbered SDS-PAGE lanes. The Exclusion Volume of the column (estimated by the elution volume of bromophenol blue) is 8.6 mL. The chromatograms show a major peat at 14.7-15 mL corresponding to the timerbody. There is also a very small peak at 8.3 mL in all three chromatograms that might contain very large aggregates. In the case of ttαCEA trimerbody there are additional minor peaks at 11 mL and 13 mL, the first one corresponding to large molecular weight contaminant proteins, as seen in lane 1 of the SDS-PAGE.

The trimeric nature of the molecules was confirmed by SEC-MALLS measurements. The sample of αCEA$^{N7}$ eluted from the size exclusion column as a major symmetric peak, and the mass calculated from the dispersed light at the center of the peak was 70.2 kDa (FIG. 6A). This value is smaller than the 77.3 kDa calculated for a trimer based on the amino acid sequence of this protein, but very close to the 69.2 kDa of a trimer calculated from the sequence excluding the N-terminal oncostatin M signal sequence. Mass spectrometry by matrix assisted laser desorption ionization confirmed the absence of the N-terminal 25 residues, suggesting that the signal sequence was cleaved during protein secretion. Purified tandem trimerbodies eluted from the size exclusion column as major symmetric peaks, with a very small portion of high molecular weight aggregates eluting at the exclusion volume of the column (FIG. 9). The masses calculated from the dispersed light at the center of the peaks were 65.7 kDa and 63.2 kDa for ttαCEA and ttαGFP-αCEA$^{(1:2)}$, respectively, close to the calculated values of 67.2 and 66.9 kDa, excluding the signal sequence (FIG. 6A).

The structure of the trimeric antibodies was investigated by circular dichroism. The spectra of the three proteins are very similar, with a minimum at around 218 nm (FIG. 6B), typical of proteins with predominantly β-sheet structure. The trimerbodies are globally folded into stable three-dimensional structures, as seen by their cooperative thermal denaturations (FIG. 6C). The proteins show a major denaturation event with similar mid-point temperatures: 56° C. for ttαCEA and 58° C. both for αCEA$^{N7}$ and ttαGFP-αCEA$^{(1:2)}$. For ttαGFP-αCEA$^{(1:2)}$, a second cooperative denaturation event of smaller amplitude occurs with a mid-point temperature of 73° C., possibly due to the unfolding of the αGFP moiety.

Serum Stability of $V_{HH}$-Based Trimerbodies.

Figure 7:
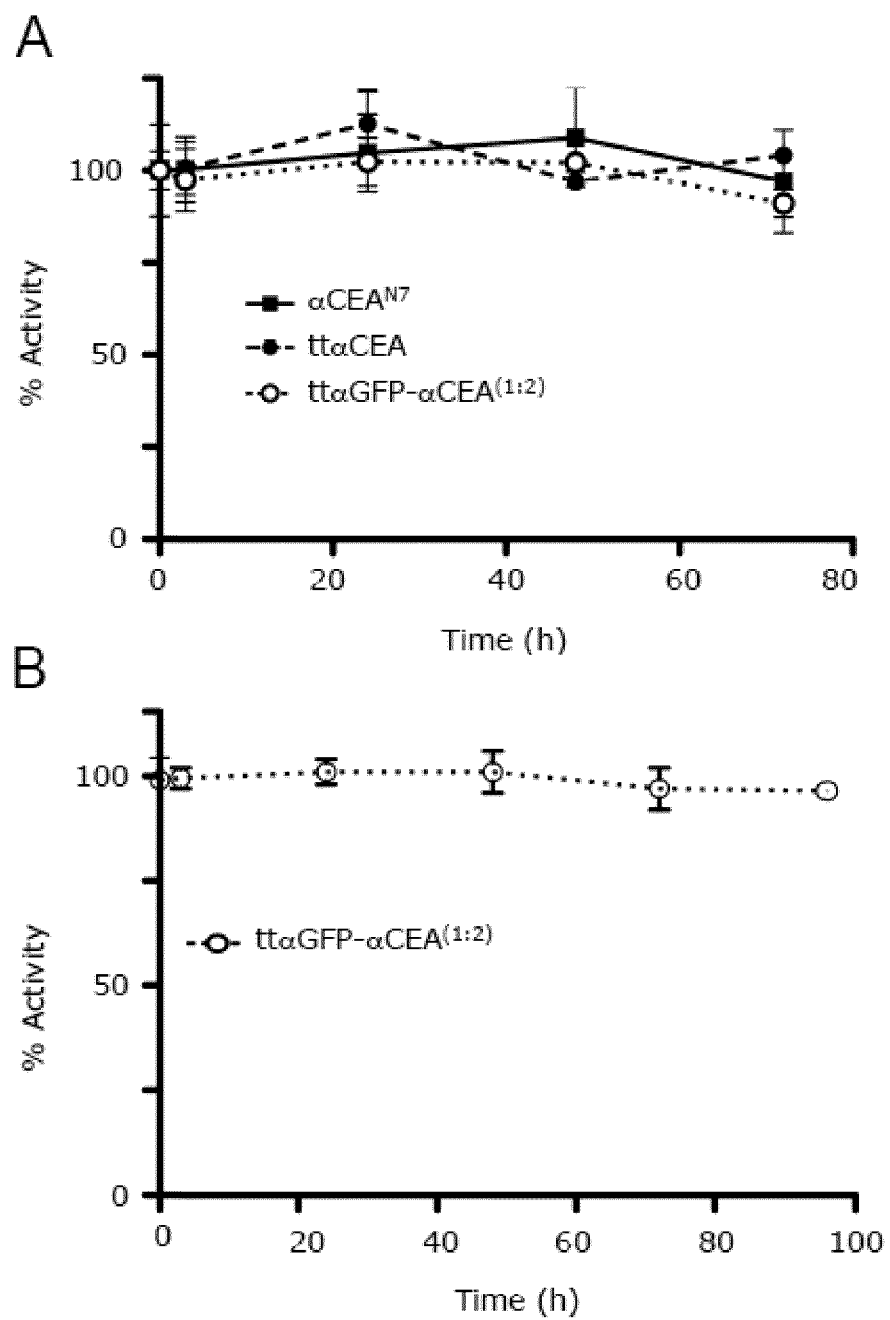
FIG. 7. Serum stability of purified αCEA$^{N7}$, ttαCEA and ttαGFP-αCEA$^{(1:2)}$ trimerbodies. ELISA against plastic immobilized human CEA (A) or GFP (B) was performed after incubation at 37° C. for different time periods in human serum, as explained in material and methods.

The serum stability was studied by incubating the purified multichain trimerbodies and tandem in human serum at 37° C., for prolonged periods of time. The binding activity of the sample at 0 hours was set as 100% in order to calculate the time corresponding to percentage decay in binding activity. As shown in FIG. 7, multichain αCEA$^{N7}$ and tandem ttαCEA and ttαGFP-αCEA$^{(1:2)}$ trimerbodies had similar stability, retaining more than 95% of the initial CEA-binding (FIG. 7A) and GFP-binding activity (FIG. 7B) after 96 hours of incubation.

Analysis of the Active Surface.

Figure 8:
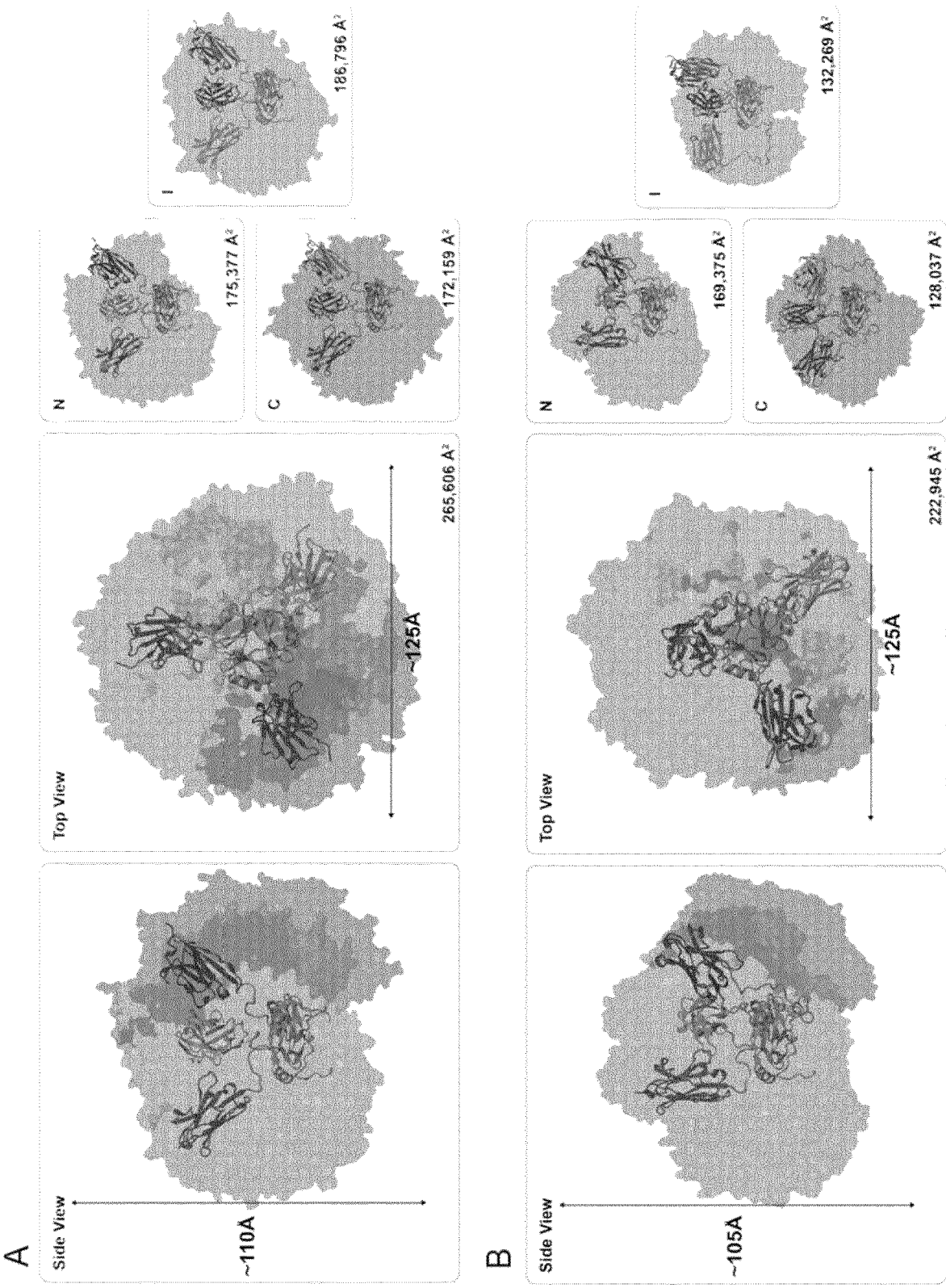
FIG. 8. Representation of the putative surfaces accessible to the $V_{HH}$ domains of the multichain trimerbody (A) and the tandem trimerbody (B). For all structures represented, trimerization domains and linkers are depicted in teal, N-terminal $V_{HH}$ (N) in red, internal $V_{HH}$ (I) in green and C-terminal $V_{HH}$ (C) in blue. The surface area represented in each image is stated in it corresponding bottom-right corner. Side (left) and top (middle) representation of the overlapped surface explored by the three $V_{HH}$ domains. A representation of the area explored for each $V_{HH}$ domain can be seen together with its total surface area in the right. Being three identical chains, labels of N, I and C are assigned just for comparison purposes. The final surface is calculated as the sum of all the volumes into one, thus the area is far smaller that the sum of the individual areas.

A comparative analysis of the positions that the $V_{HH}$ domains can putatively explore around the trimerization domain was performed for both the multichain and the tandem trimerbody. Regardless of the presence of the additional linkers, the sterically allowed spatial distribution of the $V_{HH}$ domains have an oblate shape, but slightly bigger for the multichain trimerbody with approximately 125 and 110 Å axes, than for the tandem trimerbody, with 125 and 105 Å axes (FIG. 8). The tandem $V_{HH}$-based trimerbody is, on average, more compact, likely due to the restrictions in movement imposed by the extra linkers on the internal and C-terminal $V_{HH}$ domains, but the difference is small (84% surface area as compared with the multichain trimerbody). However, the relative orientation of the $V_{HH}$ domains is severely restricted in both trimerbodies, with defined regions on the surface predominantly occupied by each of the three $V_{HH}$ domains (FIG. 8). As the multichain trimerbody contains three identical segments, each one of the $V_{HH}$ domains explores similar surface areas. In the tandem trimerbody, however, the internal and C-terminal $V_{HH}$ domains are linked to TIE trimerization domains by two linkers, but only one in the case of the N-terminal $V_{HH}$ domain. As a consequence, the surface area sampled by the N-terminal $V_{HH}$ domain is approximately 30% larger than that sampled by anyone of the other two (which sample approximately the same surface area).

III. Discussion

In this study, we used the trimerbody technology platform for the production of trivalent $V_{HH}$-based molecules. We fused $V_{HH}$ antibodies with different specificities to the N-terminus of a human TIE$^{XVIII}$ domain using linker sequences of different lengths. All the $V_{HH}$-based trimerbodies were expressed in functional active form from conditioned medium of transfected HEK-293 cells, and importantly their production levels were higher than those of scFv-based trimerbodies with the same configuration. The purified $V_{HH}$-based molecules were trimeric in solution and shown specific binding to their cognate antigens.

Furthermore, we demonstrated that multispecific molecules can be generated by co-transfecting HEK-293 cells with plasmids encoding several $V_{HH}$-based trimerbodies with different specificities. However, assuming that the rate of synthesis is the same for all the proteins and that trimerization happens randomly one would expect 10% of the total trimerbody to be trispecific. Therefore, this strategy would require, however, the isolation of the trimerbody with the desired $V_{HH}$ combination, for instance by means of three purification steps based on three orthogonal affinity tags. Such a process may be feasible but not productive.

Taking advantage of the small size and favorable biophysical properties of $V_{HH}$ antibodies (De Meyer T, et al., Trends Biotechnol 2014, 32:263-70; Muyldermans S., Annu Rev Biochem 2013, 82:775-97) and human TIE$^{XVIII}$ domain (Boudko S P, et al., J Mol Biol 2009, 392:787-802), we present an approach to rationally design multispecific $V_{HH}$-based N-trimerbodies with defined stoichiometry. We built tandem trimerbodies by connecting with additional glycine-serine-based linkers the C-terminus of the N-terminal and central TIE domain with the N-terminus of the central and C-terminal $V_{HH}$ antibodies. Recombinant monospecific and multispecific (bi and trispecific) tandem $V_{HH}$-based N-trimerbodies were efficiently secreted as soluble proteins by transfected human HEK-293 cells, and were easily purified using standard chromatographic methods. The purified tandem trimerbodies were highly homogeneous monomeric molecules in solution, as unambiguously shown by the light scattering measurements. The formation of monomers versus multimers during the folding of the chains in the cell could be favored by the design of the linkers connecting the trimerization and the $V_{HH}$ domains. Alternatively, multimers may be formed but are not secreted. The high level of protein production, however, suggests that intramolecular trimerization is favored.

The purified monospecific and multispecific tandem $V_{HH}$-based trimerbodies were very efficient at recognizing antigen. Biolayer interferometry analysis revealed that the trispecific ttαGFP-αEGFR-αCEA tandem trimerbody was capable of binding concurrently to three antigens, indicating that each domain independently binds to its cognate antigen. Importantly, this molecule recognized surface EGFR as efficiently as the anti-EGFR mAb panitumumab, and it was very efficient and specific at inducing cell adhesion of EGFR-expressing cells when pre-incubated on plastic-bound CEA or plastic-bound GFP, but not on plastic-bound BSA. One could speculate that for some applications where a strong cross-linking of cell surface receptors is necessary, the presence of two $V_{HH}$ domains with limited mobility could be favorable. The flexible linkers in the trimerbodies are long enough to allow the $V_{HH}$ domains to access a large surface area around the trimerization domain but short enough to restrict their relative orientations, and in the tandem trimerbody, the additional linkers reduced the surface accessible to the central and C-terminal domains. Therefore, this design allows for tuning the relative mobility and orientation of the individual $V_{HH}$ domains.

Monovalent $V_{HH}$ antibodies are not optimal for the in vivo therapeutic applications. They have an in vivo half-life of approximately 1.5 h in blood (Cortez-Retamozo V, et al., International J Cancer 2002, 98:456-62), and it has been demonstrated that in vivo non-equilibrium environments, even high-affinity monovalent interactions tend to have fast dissociation rates, providing modest retention times on the target antigen (Holliger P, Hudson P J., Nat Biotechnol 2005, 23:1126-36). For therapeutic applications, it is therefore, desirable to engineer monovalent $V_{HH}$ antibodies into multivalent molecules, with higher affinity, slower dissociation rates, and prolonged serum half-lives (Holliger P, Hudson P J., Nat Biotechnol 2005; 23:1126-36.). Furthermore, multimerization allows the generation of multispecific molecules, which can enhance their tissue specificity and provide antibodies with novel functionality. Although several methods have been devised for the generation of multivalent and multispecific single-domain antibodies, such as linear gene fusions (Els Conrath K, et al., J Biol Chem 2001, 276:7346-50; Coppieters K, et al., Arthritis Rheum 2006, 54:1856-66; Roovers R C, et al., Cancer Immunol Immunother 2007, 56:303-17), self-associating peptides (Plagmann I, et al., J Biotechnol 2009, 142:170-8; Zhu X, et al., Immunol Cell Biol 2010, 88:667-75) and protein domains (Aliprandi M, et al., J Biomed Biotechnol 2010, 2010:658954; Laventie B J, et al., Proc Natl Acad Sci USA 2011, 108:16404-9), the common strategy is based on the use of flexible peptide linkers. However, even bi- or trivalent tandem $V_{HH}$ antibodies are below the threshold for first-pass renal clearance (about 60 kDa) and will therefore have a very short in vivo half-life. For this reason bivalent or trivalent tandem molecules containing an anti-human serum albumin $V_{HH}$ antibody have been generated to extend the in vivo half-life of these molecules (Kontermann R E., Curr Opin Biotechnol 2011, 22:868-76).

Here we demonstrate for the first time that by inserting internal oligomerization domains in a tandem $V_{HH}$-based construct we can control the stoichiometry, the orientation, and the homogeneity of the species in solution. Tandem $V_{HH}$-based trimerbodies were also characterized by a good thermostability, and a high resistance to serum proteases. These favorable properties and the intermediate molecular weight (65-70 kDa), makes the tandem $V_{HH}$-based trimerbodies ideal candidates for in vivo cancer therapy. It is tempting to speculate that by modifying the length and amino acid composition of linkers connecting the trimerization domains we could fine-tune the geometry of tandem trimerbodies. Furthermore, by adding furin cleavage sites at both ends of the extra linker 1 and/or 2 we could restore the mobility of the internal and C-terminal $V_{HH}$ domains, given that cleavage at both furin sites would lead to the removal of the additional peptide connectors (Fang J, et al., Nat Biotechnol 2005, 23:584-90).

Multispecific tandem $V_{HH}$-based trimerbodies may have applications for the dual targeting of two receptors for cancer therapy, the development of immune cell recruitment strategies and the development of improved agonistic reagents for immunotherapy (Chames P, et al., Br J Pharmacol 2009, 157:220-33). Other possible applications of $V_{HH}$-based trimerbodies are the targeted delivery of a therapeutically active moiety, by fusing cytokines, toxins or enzymes to the C-terminus of the TIE$^{XVIII}$ domain (Blanco-Toribio A, et al., MAbs 2013, 5:70-9), and the development of more effective trapping agents for the simultaneous neutralization of different angiogenic factors or disease-modulating cytokines.

Example 2.—Potent Redirected Lysis of EGFR-Positive Tumor Cells by Asymmetric Anti-EGFR×Anti-CD3 Bispecific Tandem Trimerbodies (anti-EGFR×Anti-CD3ε Tandem $V_{HH}$-N/C-scFv Trimerbodies)

I. Materials & Methods
Reagents and Antibodies

The mAbs used included: mouse anti-c-myc clone 9E10 (Abcam, Cambridge, UK), mouse anti-human CD3E clone OKT3 (Ortho Biotech, Bridgewater, N.J.), and fully human anti-human epidermal growth factor receptor (EGFR) panitumumab (Amgen, Thousand Oaks, Calif., USA), fluorescein isothiocyanate (FITC)-conjugated anti-human CD3e (clone UCHT1, Abcam), and phycoerythrin (PE)-conjugated anti-human CD69 mAb (clone FN50, BD Biosciences, San Jose, Calif., USA). The polyclonal antibodies included: phycoerytrin (PE)-conjugated goat F(ab')$_2$ fragment anti-mouse IgG, Fc specific, (Jackson Immuno Research, Newmarket, UK); PE-conjugated goat F(ab')$_2$ fragment anti-human IgG (H&L) (Abcam), and IRDye800 conjugated donkey anti-mouse IgG (H&L) (Rockland Immunochemicals, Gilbertsville, Pa., USA).

Cells and Culture Conditions

HEK-293 (CRL-1573), HeLa cells (CCL-2) and NIH/3T3 (CRL-1568) were cultured in Dulbecco's modified Eagle's medium (DMEM) (Lonza, Walkersville, Md., USA) supplemented with 2 mM L-glutamine, 10% (vol/vol) heat inactivated Fetal Calf Serum (FCS), and antibiotics (Life Technologies, Carlsbad, Calif., USA) referred as to DMEM complete medium (DCM), unless otherwise stated. Jurkat clone E6-1 cells (TIB-152) were maintained in RPMI-1640 (Lonza) supplemented with 2 mM L-glutamine, heat-inactivated 10% FCS. All of these cell lines were obtained from the American Type Culture Collection (Rockville, Md., USA). All cell lines were routinely screened for the absence of mycoplasma contamination by PCR using the Mycoplasma Plus TM Primer Set (Stratagene, Cedar Creek, Tex., USA).

Construction of Expression Vectors

To construct the bispecific (anti-EGFR×anti-CD3E) $V_{HH}$-N/C-scFv trimerbody the BamHI/XbaI fragment from plasmid pCR3.1-hNC1$_{XVIII}$-OKT3 was ligated into the BamHI/XbaI digested backbone of plasmid pCR3.1-EGa.1-TIE$^7$ (see Example 1) to obtain the plasmid pCR3.1-EGa.1-TIE$^7$-OKT3. To generate the tandem anti-EGFR $V_{HH}$-based N-terminal trimerbody expression vector a synthetic gene containing two EGa.1 $V_{HH}$ antibodies fused at its 5'-end by a 17-mer linker to a human TIE$^{XVIII}$ domain, and at its 3'-end to a 7-mer linker to a human TIE$^{XVIII}$ domain ($^{17}$EGa.1$^7$TIE$^{17}$EGa.1$^7$TIE) was synthesized by Geneart AG (Regensburg, Germany). The NotI/BamHI cleaved fragment was ligated to into pCR3.1-EGa.1-TIE$^7$ to obtain the plasmid pCR3.1-scEGa.1-TIE. To generate the bispecific (anti-EGFR×anti-CD3E) tandem $V_{HH}$-N/C-scFv trimerbody the BamHI/XbaI fragment from plasmid pCR3.1-hNC1$_{XVIII}$-OKT3 (Blanco-Toribio A et al., MAbs (2013) 5:70-9) was ligated into the BamHI/XbaI digested backbone of plasmid pCR3.1-scEGa.1-TIE, to obtain the plasmid pCR3.1-scEGa.1-TIE-OKT3. To create the plasmid pCR3.1-EGa1-(G$_4$S)-OKT3 the DNA fragment encoding the anti-EGFR $V_{HH}$ (EGa1) was ClaI/NotI digested from pCR3.1-EGa.1-TIE$^7$ and ligated into the ClaI/NotI digested backbone of previously described plasmid pCR3.1-MFE23-(G$_4$S)-OKT3 (Compte M et al., Oncoimmunology (2014) 23; 3:e28810). The sequences were verified using primers FwCMV (SEQ ID NO: 31: 5'CGCAAATGGGCGGTAGGCGTG-3') and RvBGH (SEQ ID NO: 32: 5'TAGAAGGCACAGTCGAGG-3').

Antibody Fragment Sequences anti-EGFR V$_{HH}$ (SEQ ID NO: 18):
MAQVQLQESGGGLVQPGGSLRLSCAASGRTFSSYAMGWFRQAPGKEREFV

AAIRWSGGYTYYTDSVKGRFTISRDNAKTTVYLQMNSLKPEDTAVYYCAA

TYLSSDYSRYALPQRPLDYDYWGQGTQVTVSS anti-EGFR V$_{HH}$ encoding sequence (SEQ ID NO: 19):
ATGGCTCAGGTGCAGCTGCAGGAGTCTGGGGGAGGATTGGTGCAGCCAGG

GGGCTCGCTGAGACTCTCCTGTGCAGCCTCTGGACGCACCTTCAGTAGCT

ATGCCATGGGCTGGTTCCGCCAGGCTCCAGGGAAGGAGCGTGAGTTTGTA

GCAGCTATTAGGTGGAGTGGTGGTTACACATACTATACAGACTCCGTGAA

GGGCCGATTCACCATCTCCAGAGACAACGCCAAGACTACGGTGTATCTGC

AAATGAACAGCCTGAAACCTGAGGACACGGCCGTTTATTACTGTGCAGCA

ACATACCTGTCCTCGGACTATAGCCGCTATGCGTTGCCCCAAAGGCCCTT

GGACTATGACTACTGGGGCCAGGGGACCCAGGTCACCGTCTCCTCA anti-CD3ϵ scFv (SEQ ID NO: 20):
QVQLQQSGAELARPGASVKMSCKASGYTFTRYTMHWVKQRPGQGLEWIGY

INPSRGYTNYNQKFKDKATLTTDKSSSTAYMQLSSLTSEDSAVYYCARYY

DDHYCLDYWGQGTTLTVSSGGGGSGGGGSGGGGSDIDLTQSPAIMSASPG

EKVTMTCSASSSVSYMNWYQQKSGTSPKRWIYDTSKLASGVPAHFRGSGS

GTSYSLTISGMEAEDAATYYCQQWSSNPFTFGSGTKLEINR anti-CD3ϵ scFv encoding sequence (SEQ ID NO: 21):
CAGGTCCAGCTGCAGCAGTCTGGCGCCGAGCTGGCTAGACCTGGGGCCAG

CGTGAAGATGAGCTGCAAGGCCAGCGGCTACACCTTCACCCGGTACACCA

TGCACTGGGTCAAGCAGCGGCCTGGGCAGGGCCTGGAATGGATCGGCTAC

ATCAACCCCAGCCGGGGCTACACCAACTACAACCAGAAGTTCAAGGACAA

GGCCACCCTGACCACCGACAAGAGCAGCAGCACCGCCTACATGCAGCTGA

GCAGCCTGACCAGCGAGGACAGCGCCGTGTACTACTGCGCCCGGTACTAC

GACGACCACTACTGCCTGGACTACTGGGGCCAGGGCACCACCCTGACAGT

GTCTAGCGGCGGAGGCGGATCTGGCGGCGGAGGATCTGGGGGAGGCGGCT

CTGACATCGACCTGACACAGAGCCCCGCCATCATGAGCGCCAGCCCTGGC

GAGAAAGTGACCATGACCTGCAGCGCCAGCAGCAGCGTGTCCTACATGAA

CTGGTATCAGCAGAAGTCCGGCACCAGCCCCAAGCGGTGGATCTACGACA

CCAGCAAGCTGGCTAGCGGCGTGCCCGCCCACTTTAGAGGCAGCGGCAGC

GGTACAAGCTACTCCCTGACCATCAGCGGCATGGAAGCCGAGGACGCCGC

CACCTACTACTGCCAGCAGTGGTCCAGCAACCCCTTCACCTTCGGCTCCG

GCACCAAGCTGGAAATCAACAGA

Peptide Linker Sequences 7-mer linker:
(SEQ ID NO: 22)
GGGGSSG, 17-mer linker:
(SEQ ID NO: 23)
SGAGGSGGSSGSDGASG, 21-mer linker:
(SEQ ID NO: 24)
KNSGAGGSGGSSGSDGASGSR.

Expression and Purification of Recombinant Antibodies

HEK-293 cells were transfected with the appropriate expression vectors using calcium phosphate (Compte M et al. Cancer Gene Ther, 2007, 14:380-8) and selected in DCM with 500 mg/ml G-418 (Sigma-Aldrich, St. Louis, Mo., USA) to generate stable cell lines. Supernatants from transiently and stably transfected cell populations were analyzed by western blotting and FACS. Stably transfected cell lines were used to collect serum free conditioned medium that was dialyzed against PBS (pH 7.4) and loaded onto a HisTrap HP 1 ml column using and AKTA Prime plus system (GE Healthcare, Uppsala, Sweden). The purified proteins were dialyzed against PBS and stored at −80° C.

Western Blotting

Samples were separated under reducing conditions on 12% Tris-glycine gels and transferred to nitrocellulose membranes (Life Technologies) and probed with anti-c-myc mAb, followed by incubation with an IRDye800-conjugated donkey anti-mouse IgG. Visualization and quantitative analysis of protein bands were carried out with the Odyssey infrared imaging system (LI-COR Biosciences, Lincoln, Nebr., USA).

Flow Cytometry

Binding of anti-EGFR×anti-CD3 bispecific antibodies to HeLa and Jurkat cells, was analyzed by indirect flow cytometry staining. Briefly, cells were incubated for 30 min on ice with filtered cell-free conditioned media from stable transfected cells or purified antibodies [1 μg/mL], washed and incubated for 30 min with anti-c-myc mAb. Cells were washed and incubated with PE-conjugated goat F(ab')2 anti-mouse IgG or PE-conjugated goat F(ab')$_2$ fragment anti-human IgG. The mAbs panitumumab and OKT3 were used as positive controls. The samples were analyzed with a Beckman-Coulter FC-500 Analyzer (Coulter Electronics, Hialeah, Fla., USA).

T Cell Proliferation Assays

Human peripheral blood mononucleated cells (PBMCs) were isolated from the buffy coat fraction of healthy volunteers' peripheral blood by density-gradient centrifugation. Unstimulated human PBMCs in RPMI complete medium were plated in triplicate at $4 \times 10^5$ cells/well in a 96-well flat-bottom tissue culture plate. Antibodies at various concentrations were added, and the cells were incubated at 37° C. in a humidified atmosphere with 5% $CO_2$ for the specified time. As a positive control, human PBMCs were cultured with plastic immobilized anti-CD3 mAb [1 μg/mL]. After 48 hours 100 ml of substrate CellTiter-Glo (Promega, Madison, Wis.) were added per well, and the bioluminescence measured using a Tecan Infinite F200 plate-reading luminometer (Tecan Trading AG, Switzerland).

T Cell Activation Assay

HeLa or 3T3 cells were plated in triplicated in 96-well microtiter plates at $4 \times 10^4$/well one day before the assay. Human PBMCs cells were added in 4:1 E:T ratio on HeLa or 3T3 cells in the presence of the indicated bispecific antibodies. To determine the secretion of IL-2, aliquots of the culture supernatants were collected after 24 hours. Determination of CD69 expression was performed after 24 h incubation using PE-conjugated anti-CD69 and FITC-conjugated anti-CD3 mAbs by flow cytometry as described (Compte M et al., Oncoimmunology (2014) 23; 3:e28810).

Cytotoxicity Assay.

Gene-modified luciferase expressing HeLa (HeLa$^{Luc}$) and 3T3 cells (3T3$^{Luc}$) were plated in triplicate in 96-well microtiter plates at $4 \times 10^4$/well one day before the assay. Human PBMCs cells were added in 4:1 E:T ratio on HeLa$^{Luc}$ or 3T3$^{Luc}$ cells in the presence of the indicated bispecific antibodies. After 48 hours, cells were gently washed twice to remove PBMC and viability was measured adding D-luciferin (Promega) to a final concentration of 40 μg/ml. Percent tumor cell viability was calculated as the mean bioluminescence of each sample divided by the mean bioluminescence of the input number of control target cells times 100.

II. Results

Generation of Bispecific Anti-EGFR×Anti-CD3ε Antibodies

To generate a bispecific anti-EGFR×anti-CD3E $V_{HH}^{N/C}$scFv trimerbody ($\alpha EGFR^{N/C}\alpha CD3$) we fused the anti-EGFR EGa.1 $V_{HH}$ to the N-terminus and the scFv derived from the anti-CD3 OKT3 mAb to the C-terminus of a TIE$^{XVIII}$ domain (FIG. 11C). The anti-CD3 OKT3 scFv C-trimerbody ($^C\alpha CD3$) (Blanco-Toribio A et al., MAbs 2013, 5:70-9) (FIG. 11B), and the multichain and tandem anti-EGFR $V_{HH}$-based trimerbodies ($\alpha EGFR^N$ and tt$\alpha$EGFR) (see Example 1 and FIG. 11A) were used as controls. A conventional tandem $V_{HH}$-scFv antibody ($\alpha EGFR^-\alpha CD3$) was generated by fusing the anti-EGFR× anti-CD3 scFv via a five residues peptide linker ($G_4S$) (FIG. 11D). We generated a bispecific anti-EGFR×anti-CD3 tandem trimerbody consisting of three $\alpha EGFR^{NT}$ trimerbodies connected by two glycine-serine-based linkers on a single protein chain and the anti-CD3 scFv fused to the C-terminus of the C-terminal TIE$^{XVIII}$ domain (tt$\alpha$EGFR_$^C\alpha CD3$) (FIG. 11F).

Figure 12:
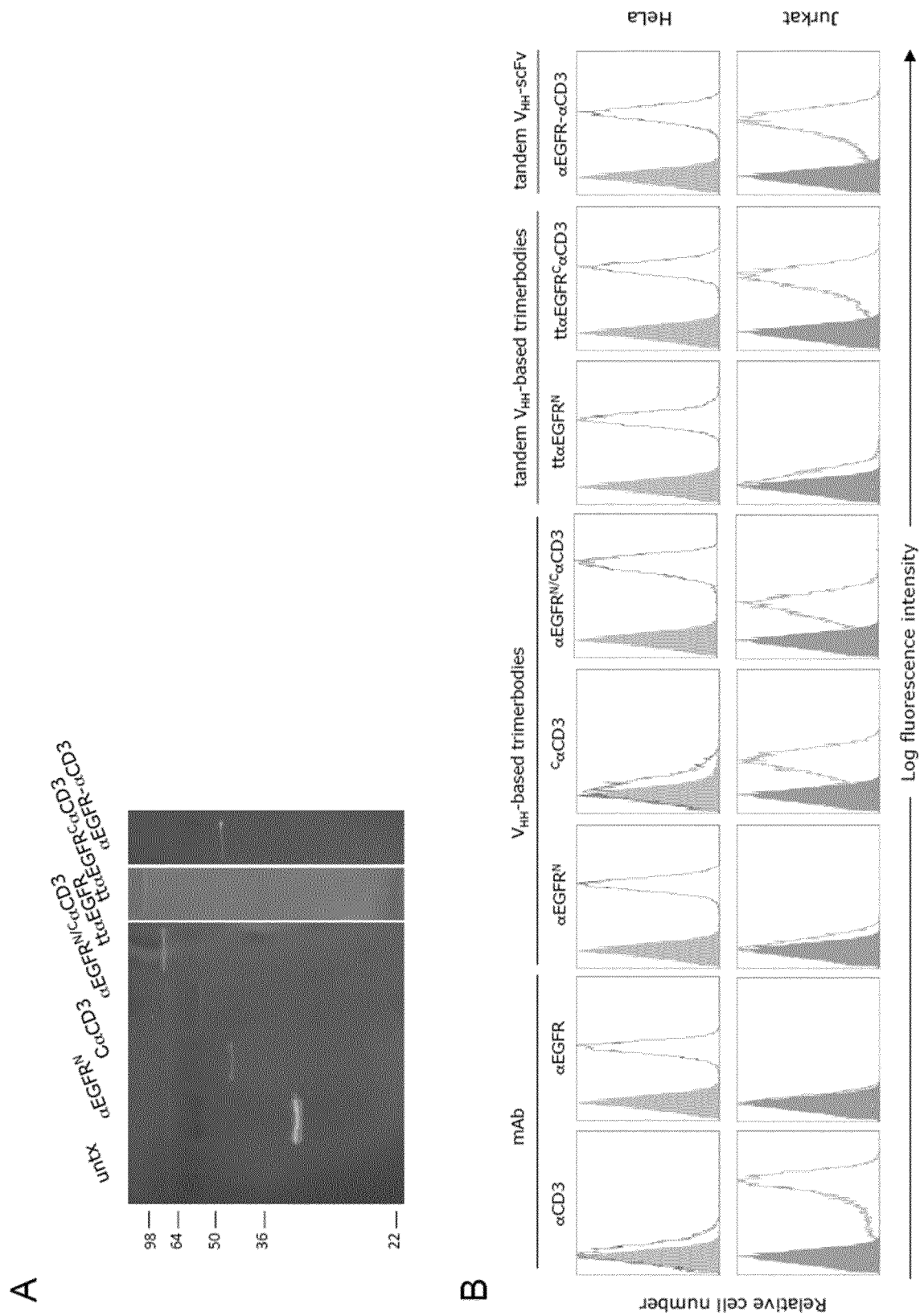
FIG. 12. Characterization of recombinant antibodies. The presence of secreted scFv-based and/or $V_{HH}$-based antibodies in the conditioned media from untrasnfected (untx) or transfected HEK-293 cells was demonstrated by western blot analysis (A). Migration distances of molecular mass markers are indicated (kDa). The blots were developed with anti-c-myc mAb. The functionality of secreted trimerbodies was demonstrated by FACS on EGFR-positive HeLa cells and EGFR-negative Jurkat cells. Anti-CD3 and anti-EGFR mAbs were used as controls.

All constructs were secreted by transfected HEK-293 cells as soluble and functional proteins. Western blot analysis under reducing conditions (FIG. 12A) showed a migration pattern of consistent with the molecular weights calculated from their amino acid sequences. The ability to detect antigen in a cellular context was studied by immunofluorescence labeling of human cells (HeLa and Jurkat). Fluorescence staining was observed after incubation of the EGFR-expressing human cervix adenocarcinoma cell line HeLa with antibodies containing the $\alpha EGFR\ V_{HH}$ domain while no binding was detected for $^C\alpha CD3$ (FIG. 12B). The EGFR-negative human T lymphoblastoid cell line Jurkat showed no binding of $\alpha EGFR^N$ and tt$\alpha$EGFR, but fluorescence staining was observed after incubation with secreted antibodies containing the $\alpha CD3$ scFv domain (FIG. 12B).

Purification of Bispecific Anti-EGFR×Anti-CD3ε Antibodies

Figure 13:
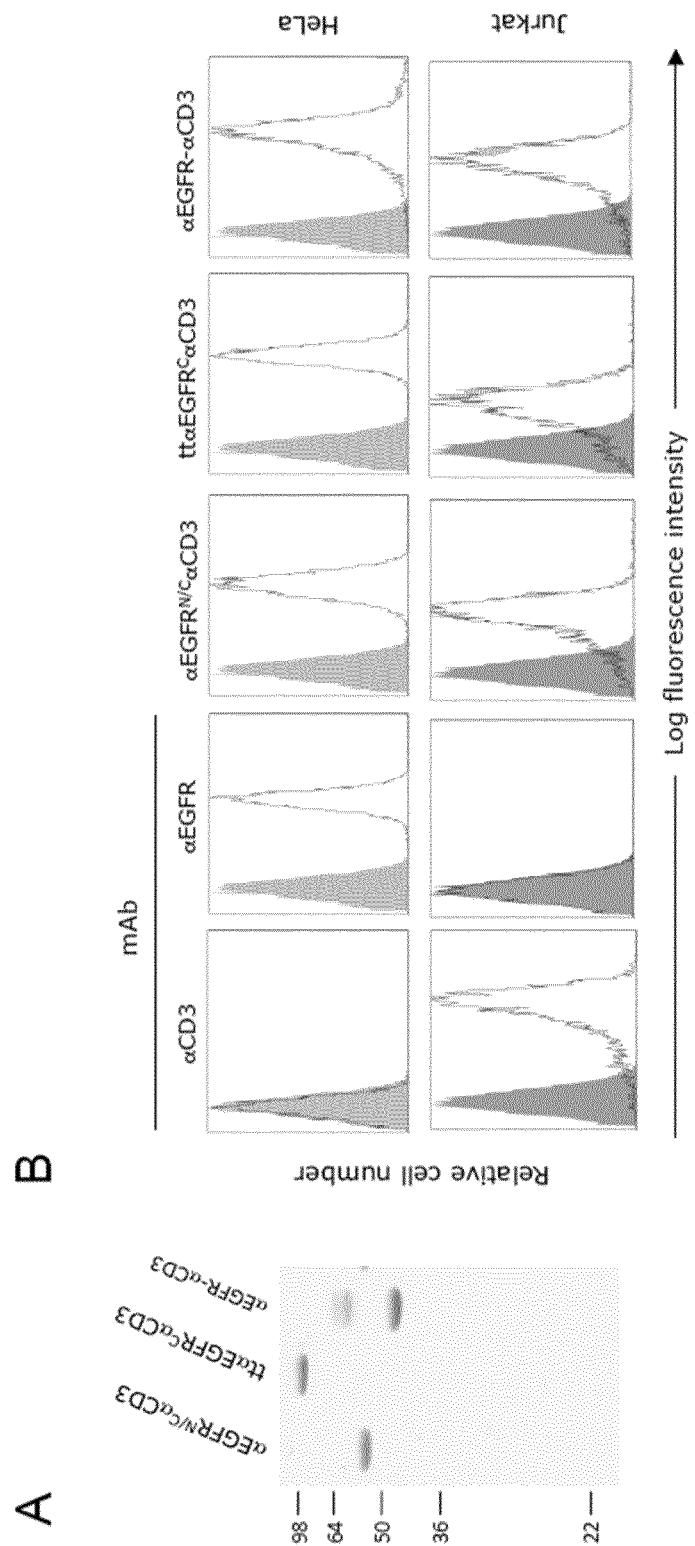
FIG. 13. Characterization of purified αEGFR_αCD3, αEGFR$^{N/C}$αCD3, and ttαEGFR_$^C$αCD3 antibodies. Reducing SDS-PAGE (A) and FACS (B) on EGFR-positive HeLa cells and EGFR-negative Jurkat cells. Anti-CD3 and anti-EGFR mAbs were used as controls.

The antibodies $\alpha EGFR\_\alpha CD3$, $\alpha EGFR^{N/C}\alpha CD3$, and tt$\alpha$EGFR_$^C\alpha CD3$ were purified from conditioned medium by immobilized metal affinity chromatography, which yielded proteins that were >90% pure by reducing SDS-PAGE (FIG. 13A). The functionality of the purified antibodies was demonstrated by flow cytometry. As shown in FIG. 13B, all of them produced robust and similar binding signals in FACS analysis with EGFR-expressing and CD3-expressing cell lines.

T Cell Activation by Bispecific Anti-EGFR×Anti-CD3ε Antibodies

Next, we compared the efficacy of the purified bispecific antibodies to induce primary human T cell proliferation. Unstimulated peripheral blood mononuclear cells (PBMCs) from healthy donors were cultured alone in the presence of different amounts of $\alpha EGFR\_\alpha CD3$, $\alpha EGFR^{N/C}\alpha CD3$, and tt$\alpha$EGFR_$^C\alpha CD3$ antibodies and nonspecific T cell activation was observed in response to the hexavalent $\alpha EGFR^{N/}$c$\alpha CD3$ trimerbody (data not shown). By contrast, the tt$\alpha$EGFR_$\alpha CD3$ and $\alpha EGFR\_^C\alpha CD3$ antibodies exerted almost no proliferative stimulus when primary T cells were cultured alone (data not shown).

Figure 14:
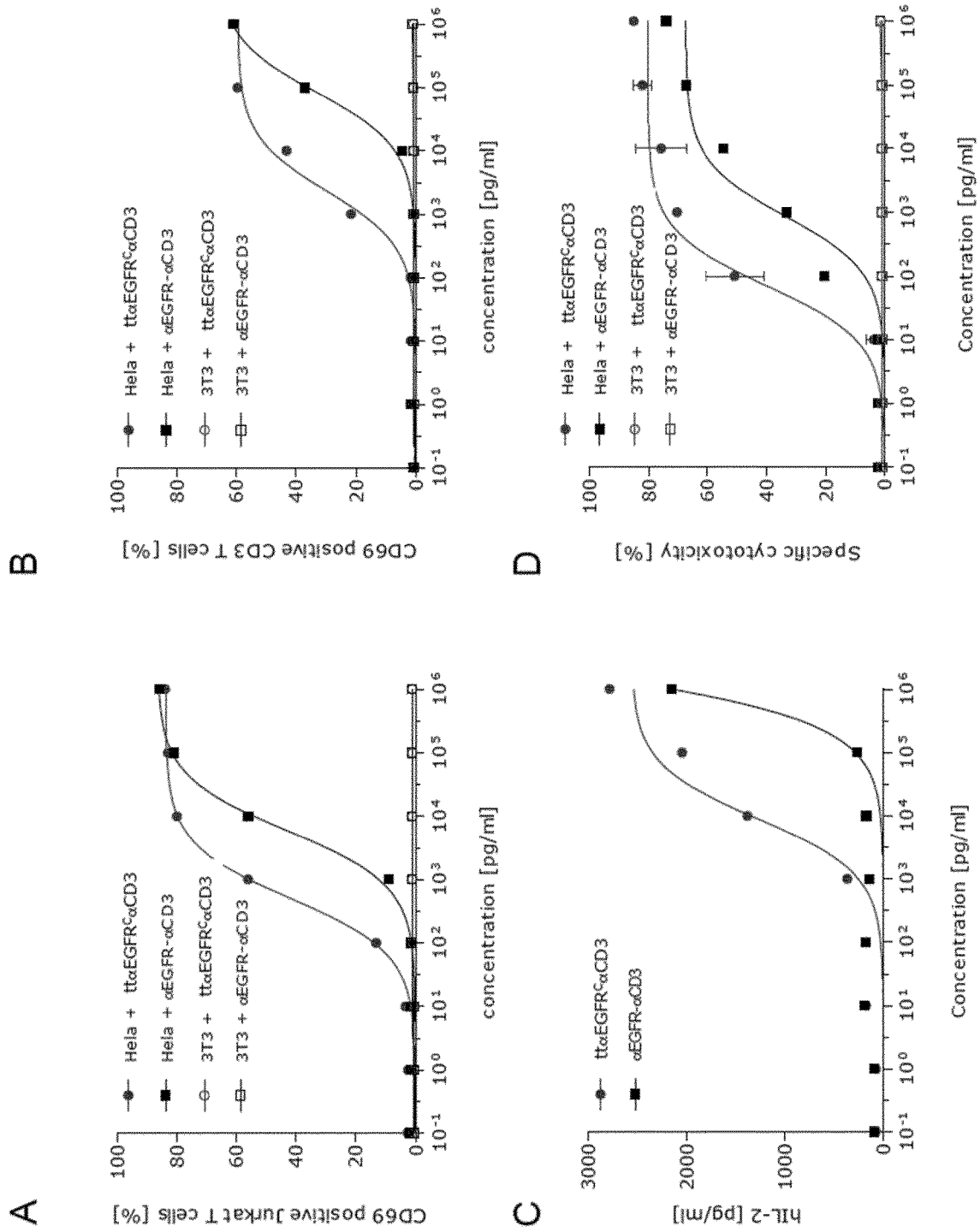
FIG. 14. Functional characterization of αEGFR_αCD3 and ttαEGFR_$^C$αCD3 antibodies. T cell activation in response to αEGFR_αCD3 and ttαEGFR_$^C$αCD3 antibodies was investigated by surface expression of immediate/early T cell activation surface marker CD69 on Jurkat cells (A) or on primary human T cells (B) using FACS analysis. Dose-dependent secretion of IL-2 by primary human T cells cultured on EGFR-positive HeLa cells and EGFR-negative 3T3 cells (C). Dose-dependent redirected lysis of human EGFR-positive HeLa cells by αEGFR_αCD3 and ttαEGFR_$^C$αCD3 antibodies (D).

In the presence of EGFR-positive target cells, both $\alpha EGFR\_\alpha CD3$ and tt$\alpha$EGFR_$^C\alpha CD3$ antibodies induced, in a dose-dependent fashion, de novo expression of the early T cell activation marker CD69 on Jurkat cells and on human T cells derived from PBMCs (FIGS. 14A and B). Importantly, the multivalent ttαEGFR_$^C$αCD3 trimerbody was 10-fold more effective than the divalent tandem αEGFR_αCD3 antibody. As shown in FIG. 14C, the ttαEGFR_$^C$αCD3 was 100-fold more effective at inducing IL-2 secretion by human peripheral T cells in the presence of EGFP-expressing cell lines than the EGFR_αCD3 antibody. The bispecific antibodies EGFR_αCD3 and ttαEGFR_$^C$αCD3 both induced a robust redirected lysis by human T cells of the EGFR+ cell line in a dose dependent manner (FIG. 14D). The mean concentrations for half-maximal lysis were 90 µg/mL for ttαEGFR_$^C$αCD3 trimerbody and 1000 µg/mL for αEGFR_αCD3 antibody (FIG. 14C). Additionally, EGFR-negative target cells (3T3) were not killed on incubation with cytotoxic T cells and αEGFR_αCD3 and αEGFR_$^C$αCD3 antibodies (FIG. 14D).

III. Conclusion

In this study, we used the trimerbody technology platform for the production of asymmetric bispecific tandem trimerbodies containing three anti-EGFR V$_{HH}$-TIE$^{XVIII}$ modules connected with two additional glycine-serine-based linkers on a single-polypeptide chain and one anti-CD3 scFv fused to the C-terminus of the third TIE$^{XVIII}$. Recombinant bispecific ttαEGFR_$^C$αCD3 trimerbodies were efficiently secreted as soluble proteins by transfected human HEK-293 cells, and were easily purified using standard chromatographic methods. The purified ttαEGFR._$^C$αCD3 trimerbodies were very efficient at recognizing antigen. Whereas conventional multichain bispecific anti-EGFR×anti-CD3 V$_{HH}^{N/C}$scFv trimerbody induced human T cell activation and proliferation in an antigen-independent manner, the asymmetric bispecific tandem trimerbody exerted almost no proliferative stimulus when human T cells were cultured alone or in co-cultures with EGFR negative cells. Importantly, asymmetric tandem trimerbody were 10 to 100-fold more effective that conventional tandem antibodies at inducing T cell activation and to effectively engage T cells for redirected lysis of EGFR-expressing cancer cells.

---

The invention claimed is:

1. A molecule according to formula (I) which comprises or consists of:

$(A)_w$-$(L1)_x$-C1-L2-B1-L3-C2-L4-B2-L5-C3-$(L6)_y$-$(D)_z$ wherein B1 and B2 are single-domain antibodies (sdAbs);
wherein C1, C2 and C3 are a collagen XV trimerizing structural element (TSE) or a collagen XVIII TSE;
wherein the collagen XV TSE is a polypeptide which comprises or consists of a polypeptide having the amino acid sequence shown in SEQ ID NO: 1;
wherein the collagen XVIII TSE is a polypeptide which comprises or consists of a polypeptide having the amino acid sequence shown in SEQ ID NO: 2;
wherein L1, L2, L3, L4, L5 and L6 are flexible peptide linkers, and wherein L2 and L4 have a length from 5 to 40 amino acids;
wherein C1-L2-B1-L3-C2-L4-B2-L5-C3 is a recombinant single-chain polypeptide, C1 being located at the N-terminus and C3 at the C-terminus of the recombinant single-chain polypeptide;
wherein w, x, y and z can be 1 or 0;
wherein when w is 1 and A is a moiety with binding, detection and/or effector properties, then A is directly or indirectly covalently linked to the N-terminus of said recombinant single-chain polypeptide; and
wherein when z is 1 and D is a moiety with binding, detection and/or effector properties then D is directly or indirectly covalently linked to the C-terminus of said recombinant single-chain polypeptide;
wherein the flexible peptide linker comprises 2 or more amino acids selected from the group consisting of Gly, Ser, Ala and Thr.

2. The molecule according to claim 1, wherein when w is 1 and A is a polypeptide then x is 1, and when z is 1 and D is a polypeptide then y is 1.

3. The molecule according to claim 1, wherein L2 and L4 have a length from 10 to 30 amino acids.

4. The molecule according to claim 1, wherein said TSE consists of the N-terminal trimerization region of collagen XV of SEQ ID NO: 1 or of collagen XVIII of SEQ ID NO: 2.

5. The molecule according to claim 1, wherein at least 80% of the amino acids in said peptide linkers are selected from the group consisting of Gly, Ser, Ala and Thr.

6. The molecule according to claim 1, wherein said peptide linkers contain repeats of amino acid residues.

7. The molecule according to claim 6, wherein said repeats of amino acid residues are Gly-Ser or Ser-Gly repeats.

8. The molecule according to claim 1, wherein said molecule is selected from the group consisting of:
i. a molecule wherein w and x are 1; A, B1 and B2 are sdAbs or AbMs; y is 0, and z is 0 or z is 1 when D is a moiety other than a polypeptide;
ii. a molecule wherein w and x are 1; A is a single-chain variable fragment (scFv), and B1 and B2 are sdAbs; y is 0, and z is 0 or z is 1 when D is a moiety other than a polypeptide;
iii. a molecule wherein z and y are 1; D, B1, and B2 are sdAbs; x is 0, and w is 0 or w is 1 when A is a moiety other than a polypeptide;
iv. a molecule wherein z and y are 1; D is a scFv, and B1 and B2 are sdAbs; x is 0, and w is 0 or w is 1 when A is a moiety other than a polypeptide;
v. a molecule wherein w, x, y and z are 1; and A, B1, B2 and D are sdAbs;
vi. a molecule wherein w, x, y and z are 1; and A, B1 and B2 are sdAbs, and D is a scFv;
vii. a molecule wherein w, x, y and z are 1; and D, B1 and B2 are sdAbs, and A is a scFv;
viii. a molecule wherein w, x, y and z are 1; and A and D are scFv and B1 and B2 are sdAbs;
ix. a molecule wherein w and x are 0; y and z are 1; B1 and B2 are sdAbs; and D is a polypeptide selected from the group consisting of a receptor molecule or the ligand-binding part of said receptor molecule, a cytokine, a toxin polypeptide, an enzyme, a peptide tag and the Fc region of an antibody;
x. a molecule wherein y and z are 0; w and x, are 1; B1 and B2 are sdAbs; and A is a polypeptide selected from the group consisting of a receptor molecule or the ligand-binding part of said receptor molecule, a cytokine, a toxin polypeptide, an enzyme, a peptide tag and the Fc region of an antibody;
xi. a molecule wherein w and z are 1; x and y are 0; B1 and B2 are sdAbs; and A and D are moieties other than a polypeptide;
xii. a molecule wherein w, x, y and z are 0; and B1 and B2 are sdAbs.

9. The molecule according to claim 1, wherein B1 and B2 are sdAbs.

10. The molecule according to claim 1, wherein w and x are 1; A, B1 and B2 are sdAbs; y is 0, and z is 0.

11. The molecule according to claim 1, wherein w, x, y and z are 1; A, B1 and B2 are sdAbs; and D is a scFv.

12. A composition comprising a molecule according to claim 1.

13. The composition according to claim 12, wherein said composition is a pharmaceutical composition further comprising a pharmaceutically acceptable excipient.

14. A method of treating cancer, comprising administering an effective amount of a molecule of claim 1 to a subject in need thereof, alone or as a combination therapy;
wherein said molecule is a molecule selected from the group consisting of:
a molecule wherein w, x, y and z are 1; and A, B1 and B2 are sdAbs, and D is a scFv;
a molecule wherein w, x, y and z are 1; and D, B1 and B2 are sdAbs, and A is a scFv;
a molecule wherein w, x, y and z are 1; and A and D are scFv, and B1 and B2 are sdAbs;
wherein B1 and B2 are directed against the same tumor-associated antigen, and A and/or D is directed against an immune function modulating antigen.

15. A method of treating autoimmune disease, comprising administering an effective amount of the molecule of claim 1 to a subject in need thereof, alone or as a combination therapy.

16. A process for the production of a molecule of formula (I) of claim 1, comprising the steps of:
   a. introducing a recombinant expression vector comprising a nucleic acid sequence encoding the molecule of formula (I) into an appropriate host cell;
   b. culturing the host cell in conditions which enable expression of the nucleic acid sequence,
   c. optionally, isolating and/or purifying the expressed polypeptide.

17. A method for the targeted delivery of a therapeutic and/or diagnostic moiety, wherein the method comprises administering a molecule according to claim 1.

18. The method according to claim 14, wherein said molecule is a molecule wherein w, x, y and z are 1; and A, B1 and B2 are sdAbs, and D is a scFv.

19. The method according to claim 14, wherein A and/or D are directed against a T cell surface antigen.

20. The method according to claim 18, wherein D is directed against a T cell surface antigen.

21. The method according to claim 18, wherein A, B1 and B2 are sdAbs against the same tumor-associated antigen and D is a scFv against a T-cell surface antigen.

22. The method according to claim 19, wherein said T-cell surface antigen is CD3.

23. The method according to claim 20, wherein said T-cell surface antigen is CD3.

\* \* \* \* \*